(12) United States Patent
Brookings et al.

(10) Patent No.: US 9,096,614 B2
(45) Date of Patent: Aug. 4, 2015

(54) THERAPEUTICALLY ACTIVE THIAZOLO-PYRIMIDINE DERIVATIVES

(71) Applicants: UCB Pharma S.A., Brussels (BE); Katholieke Universiteit Leuven, K.U.Leuven R&D, Leuven (BE)

(72) Inventors: Daniel Christopher Brookings, Slough (GB); Daniel James Ford, Slough (GB); Richard Jeremy Franklin, Slough (GB); Anant Ramrao Ghawalkar, Hyderabad (IN); Claire Louise Kulisa, Slough (GB); Judi Charlotte Neuss, Slough (GB); James Thomas Reuberson, Slough (GB)

( * ) Notice: Subject to any disclaimer, the term of this patent is extended or adjusted under 35 U.S.C. 154(b) by 0 days.

(21) Appl. No.: 14/357,340

(22) PCT Filed: Nov. 8, 2012

(86) PCT No.: PCT/EP2012/072130
§ 371 (c)(1),
(2) Date: May 9, 2014

(87) PCT Pub. No.: WO2013/068458
PCT Pub. Date: May 16, 2013

(65) Prior Publication Data
US 2014/0315885 A1    Oct. 23, 2014

(30) Foreign Application Priority Data

Nov. 10, 2011    (GB) .................................... 1119401.6

(51) Int. Cl.
*C07D 513/04*    (2006.01)
*C07D 519/00*    (2006.01)
(Continued)

(52) U.S. Cl.
CPC ............ *C07D 513/04* (2013.01); *A61K 31/519* (2013.01); *C07D 519/00* (2013.01)

(58) Field of Classification Search
CPC ... C07D 513/04; C07D 519/00; A61K 31/519
USPC ........................................ 544/255; 514/260.1
See application file for complete search history.

(56) References Cited

U.S. PATENT DOCUMENTS 7,557,112 B2 *    7/2009    Yonetoku et al. .......... 514/260.1
2003/0013721 A1 *    1/2003    Meghani et al. ......... 514/253.01

FOREIGN PATENT DOCUMENTS

DE    2 155 963 A1    5/1973
EP    1806347 A1    7/2007
(Continued)

OTHER PUBLICATIONS

Cantaert et al. J Immunol 2008, 181:785-794.*
(Continued)

*Primary Examiner* — Venkataraman Balasubramanian
(74) *Attorney, Agent, or Firm* — McDonnell Boehnen Hulbert & Berghoff LLP

(57) ABSTRACT

A series of thiazolo[5,4-d]pyrimidine derivatives of formula (I) or an N-oxide thereof, or a pharmaceutically acceptable salt or solvate thereof: (I) Q represents a group of formula (Qa), (Qb), (Qc), (Qd) or (Qe) are beneficial in the treatment and/or prevention of various human ailments, including inflammatory, autoimmune and oncological disorders; viral diseases; and organ and cell transplant rejection.

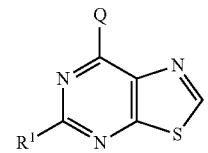

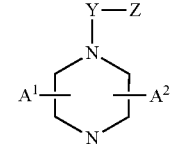

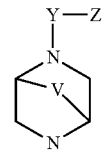

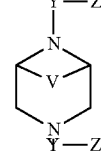

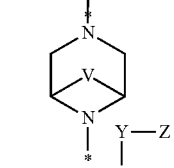

10 Claims, No Drawings

(51) Int. Cl.
*A61K 31/519* (2006.01)
*A61P 37/06* (2006.01)

(56) References Cited

FOREIGN PATENT DOCUMENTS

| GB | 1390658 | A | * | 9/1976 |
|---|---|---|---|---|
| WO | 01/46200 | A1 | | 6/2001 |
| WO | 2008/059368 | A2 | | 5/2008 |
| WO | 2008/152390 | A1 | | 12/2008 |
| WO | 2010/103130 | A2 | | 9/2010 |

OTHER PUBLICATIONS

Cecil Textbook of Medicine, edited by Bennet, J.C., and Plum F., 20th edition, vol. 1, 1004-101 O, 1996.*
Dermer et al., Bio/Technology, 1994, 12:320.*
Freshney et al., Culture of Animal Cells, A Manual of Basic Technique, Alan R. Liss, Inc., 1983, New York, p4.*
Golub et al., Science, 286, 531-537, 1999.*

* cited by examiner

THERAPEUTICALLY ACTIVE THIAZOLO-PYRIMIDINE DERIVATIVES

This application is a U.S. national phase of International Application No. PCT/EP2012/072130 filed on Nov. 8, 2012, which claims priority to Great Britain Patent Application No. 1119401.6 filed on Nov. 10, 2011.

The present invention relates to a class of fused pyrimidine derivatives, and to their use in therapy. More particularly, the present invention provides thiazolo[5,4-d]-pyrimidine derivatives that are unsubstituted at the 2-position, and substituted at the 7-position by a diaza monocyclic, bridged bicyclic or spirocyclic moiety. These compounds are of benefit as pharmaceutical agents, especially in the treatment of adverse inflammatory, autoimmune and oncological disorders, in the treatment of viral diseases, and in the management of organ and cell transplant rejection.

In addition, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2010/103130 describes a family of oxazolo[5,4-d] pyrimidine, thiazolo[5,4-d]-pyrimidine, thieno[2,3-d]pyrimidine and purine derivatives that are active in a range of assays, including the Mixed Lymphocyte Reaction (MLR) test, and are stated to be effective for the treatment of immune and auto-immune disorders, and organ and cell transplant rejection. Copending international patent application PCT/EP2011/058276, published on 1 Dec. 2011 as WO 2011/147753, discloses the same family of compounds as having significant antiviral activity. Furthermore, copending international patent application PCT/IB2011/002248, published on 22 Mar. 2012 as WO 2012/035423, discloses the same family of compounds as having significant anticancer activity.

None of the prior art available to date, however, discloses or suggests the precise structural class of thiazolo[5,4-d]pyrimidine derivatives as provided by the present invention, in which the 2-position is unsubstituted.

The compounds in accordance with the present invention are active as inhibitors when subjected to the Mixed Lymphocyte Reaction (MLR) test. The MLR test is predictive of immunosuppression or immunomodulation. Thus, when subjected to the MLR test, the compounds of the present invention display an $IC_{50}$ value of 10 µM or less, generally of 5 µM or less, usually of 2 µM or less, typically of 1 µM or less, suitably of 500 nM or less, ideally of 100 nM or less, and preferably of 20 nM or less (the skilled person will appreciate that a lower $IC_{50}$ figure denotes a more active compound).

The present invention provides a compound of formula (I) or an N-oxide thereof, or a pharmaceutically acceptable salt or solvate thereof:

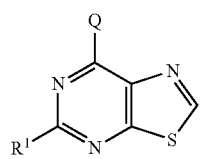

(I)

wherein

Q represents a group of formula (Qa), (Qb), (Qc), (Qd) or (Qe):

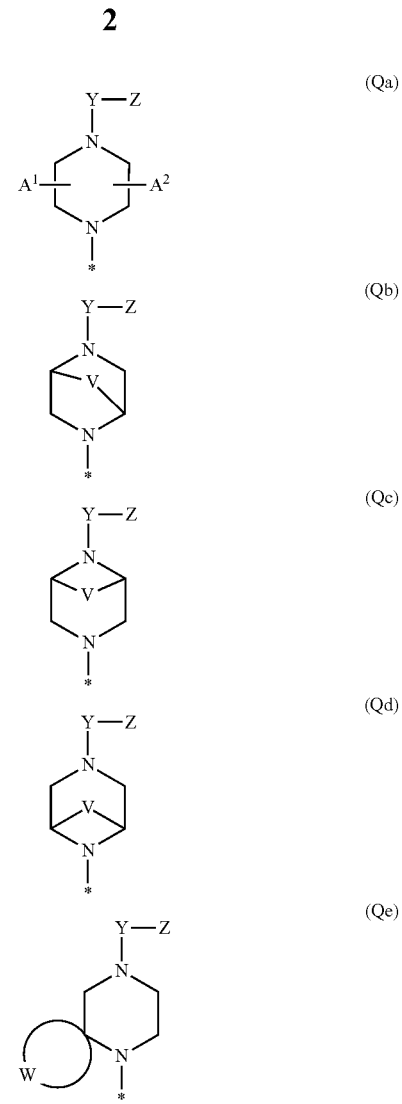

in which the asterisk (*) represents the point of attachment to the remainder of the molecule;

V represents —$CH_2$—, —$C(CH_3)_2$—, —$CH_2CH_2$— or —$CH_2CH_2CH_2$—;

W represents the residue of a $C_{3-7}$ cycloalkyl group;

Y represents a covalent bond, or a linker group selected from —C(O)—, —S(O)—, —S(O)$_2$—, —C(O)O—, —C(O)N(R$^2$)— and —S(O)$_2$N(R$^2$)—, or a linker group of formula (Ya):

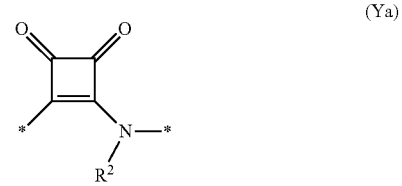

in which the asterisk (*) represents the point of attachment to the remainder of the molecule;

Z represents hydrogen; or $C_{1-6}$ alkyl, $C_{2-6}$ alkenyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents;

$A^1$ represents hydrogen, cyano or trifluoromethyl; or $A^1$ represents $C_{1-6}$ alkyl, optionally substituted by one or more substituents independently selected from $-OR^a$, $-NR^bR^c$, $-CO_2R^d$ and $-CONR^bR^c$; or $A^1$ represents $C_{3-7}$ cycloalkyl;

$A^2$ represents hydrogen or $C_{1-6}$ alkyl;

$R^1$ represents hydrogen, halogen, cyano, nitro, hydroxy, trifluoromethyl, trifluoromethoxy, $-OR^a$, $-SR^a$, $-SOR^a$, $-SO_2R^a$, $-NR^bR^c$, $-CH_2NR^bR^c$, $-NR^cCOR^d$, $-CH_2NR^cCOR^d$, $-NR^cCO_2R^d$, $-NHCONR^bR^c$, $-NR^cSO_2R^e$, $-N(SO_2R^e)_2$, $-NHSO_2NR^bR^c$, $-COR^d$, $-CO_2R^d$, $-CONR^bR^c$, $-CON(OR^a)R^b$ or $-SO_2NR^bR^c$; or $C_{1-6}$ alkyl, aryl, aryl($C_{1-6}$)alkyl, heteroaryl or heteroaryl($C_{1-6}$)alkyl, any of which groups may be optionally substituted by one or more substituents;

$R^2$ represents hydrogen; or $C_{1-6}$ alkyl, optionally substituted by one or more substituents independently selected from $-OR^a$ and $-NR^bR^c$;

$R^a$ represents hydrogen; or $R^a$ represents $C_{1-6}$ alkyl, aryl, aryl($C_{1-6}$)alkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

$R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

The present invention also provides a compound of formula (I) as depicted above or an N-oxide thereof, or a pharmaceutically acceptable salt or solvate thereof, wherein:

Q represents a group of formula (Qa);

Y represents a covalent bond, or a linker group selected from $-C(O)-$, $-S(O)-$, $-S(O)_2-$, $-C(O)O-$, $-C(O)N(R^2)-$ and $-S(O)_2N(R^2)-$;

Z represents hydrogen; or $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents;

$A^1$ represents hydrogen or trifluoromethyl; or $C_{1-6}$ alkyl, optionally substituted by one or more substituents independently selected from $-OR^a$ and $-NR^bR^c$;

$A^2$ represents hydrogen;

$R^a$ represents $C_{1-6}$ alkyl, aryl, aryl($C_{1-6}$)alkyl, heteroaryl or heteroaryl($C_{1-6}$)alkyl, any of which groups may be optionally substituted by one or more substituents; and $R^1$, $R^2$, $R^b$, $R^c$, $R^d$ and $R^e$ are as defined above.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl, pentyl and hexyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable $C_{2-6}$ alkenyl groups include vinyl, allyl and prop-1-en-2-yl.

Suitable $C_{3-7}$ cycloalkyl groups, which may comprise benzo-fused analogues thereof, include cyclopropyl, cyclobutyl, cyclopentyl, indanyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include oxetanyl, azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-c]pyridinyl, pyrazolo[3,4-d]pyrimidinyl, indazolyl, oxazolyl, benzoxazolyl, isoxazolyl, thiazolyl, benzothiazolyl, isothiazolyl, imidazolyl, imidazo[2,1-b]thiazolyl, benzimidazolyl, imidazo[1,2-c]pyridinyl, imidazo[4,5-b]pyridinyl, purinyl, imidazo[1,2-c]pyrimidinyl, imidazo[1,2-c]pyrazinyl, oxadiazolyl, thiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto $(CH_2C=O) \leftrightarrows$ enol $(CH=CHOH)$ tautomers or amide $(NHC=O) \leftrightarrows$ hydroxyimine $(N=COH)$ tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In a particular embodiment, Q represents a group of formula (Qa) as defined above. In a second embodiment, Q represents a group of formula (Qb) as defined above. In a third embodiment, Q represents a group of formula (Qc) as defined above. In a fourth embodiment, Q represents a group of formula (Qd) as defined above. In a fifth embodiment, Q represents a group of formula (Qe) as defined above.

Where Q represents a group of formula (Qa) as defined above, this may be a group of formula (Qa-1), (Qa-2), (Qa-3), (Qa-4), (Qa-5) or (Qa-6):

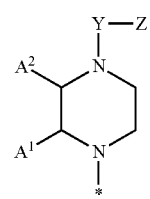
(Qa-1)

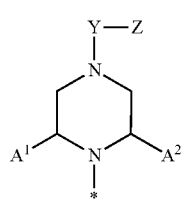
(Qa-2)

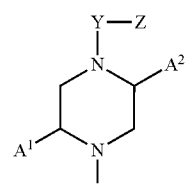
(Qa-3)

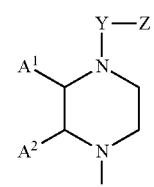
(Qa-4)

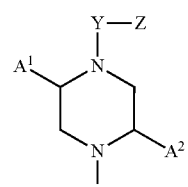
(Qa-5)

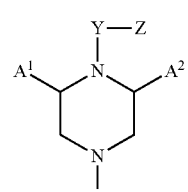
(Qa-6)

in which the asterisk (*) represents the point of attachment to the remainder of the molecule; and Y, Z, $A^1$ and $A^2$ are as defined above.

In a first embodiment, Q represents a group of formula (Qa-1) as defined above.

In a second embodiment, Q represents a group of formula (Qa-2) as defined above.

In a third embodiment, Q represents a group of formula (Qa-3) as defined above.

In a fourth embodiment, Q represents a group of formula (Qa-4) as defined above.

In a fifth embodiment, Q represents a group of formula (Qa-5) as defined above.

In a sixth embodiment, Q represents a group of formula (Qa-6) as defined above.

In one embodiment, V represents —$CH_2$— or —$C(CH_3)_2$—. In a first aspect of that embodiment, V represents —$CH_2$—. In a second aspect of that embodiment, V represents —$C(CH_3)_2$—. Where Q represents a group of formula (Qb) and V represents —$CH_2$— or —$C(CH_3)_2$—, the bicyclic moiety containing the integer V is a 2,5-diazabicyclo[2.2.1]-heptane ring system. Where Q represents a group of formula (Qc) or (Qd) and V represents —$CH_2$— or —$C(CH_3)_2$—, the bicyclic moiety containing the integer V is a 3,6-diazabicyclo[3.1.1]heptane ring system.

In another embodiment, V represents —$CH_2CH_2$—. Where Q represents a group of formula (Qb) and V represents —$CH_2CH_2$—, the bicyclic moiety containing the integer V is a 2,5-diazabicyclo[2.2.2]octane ring system. Where Q represents a group of formula (Qc) or (Qd) and V represents —$CH_2CH_2$—, the bicyclic moiety containing the integer V is a 3,8-diazabicyclo[3.2.1]octane ring system.

In a further embodiment, V represents —CH$_2$CH$_2$CH$_2$—. Where Q represents a group of formula (Qb) and V represents —CH$_2$CH$_2$CH$_2$—, the bicyclic moiety containing the integer V is a 6,8-diazabicyclo[3.2.2]nonane ring system. Where Q represents a group of formula (Qc) or (Qd) and V represents —CH$_2$CH$_2$CH$_2$—, the bicyclic moiety containing the integer V is a 7,9-diazabicyclo[3.3.1]nonane ring system.

Where Q represents a group of formula (Qe), the C$_{3-7}$ cycloalkyl group of which W is the residue is spiro-fused to the adjacent six-membered ring containing two nitrogen atoms. The cyclic group of which W is the residue is selected from cyclopropyl, cyclobutyl, cyclopentyl, cyclohexyl and cycloheptyl. Suitably, the cyclic group of which W is the residue is a C$_{4-6}$ cycloalkyl group. In a particular embodiment, the cyclic group of which W is the residue is cyclobutyl.

Typically, Y represents a covalent bond, or a linker group selected from —C(O)—, —C(O)O— and —C(O)N(R$^2$)—, or a linker group of formula (Ya) as defined above.

Suitably, Y represents a covalent bond, or a linker group selected from —C(O)— and —C(O)N(R$^2$)—.

Appositely, Y represents a covalent bond, or a linker group selected from —C(O)—, —S(O)—, —S(O)$_2$—, —C(O)O—, —C(O)N(R$^2$)— and —S(O)$_2$N(R$^2$)—.

Suitable values of Y include —C(O)—, —S(O)—, —S(O)$_2$—, —C(O)O—, —C(O)N(R$^2$)— and —S(O)$_2$N(R$^2$)—.

Selected values of Y include —C(O)— and —C(O)N(R$^2$)—.

In a first embodiment, Y represents a covalent bond. In a second embodiment, Y represents —C(O)—. In a third embodiment, Y represents —S(O)—. In a fourth embodiment, Y represents —S(O)$_2$—. In a fifth embodiment, Y represents —C(O)O—. In a sixth embodiment, Y represents —C(O)N(R$^2$)—. In a seventh embodiment, Y represents —S(O)$_2$N(R$^2$)—. In an eighth embodiment, Y represents a group of formula (Ya) as defined above.

Generally, Z represents hydrogen; or C$_{1-6}$ alkyl, C$_{3-7}$ cycloalkyl, C$_{3-7}$ cycloalkyl(C$_{1-6}$)alkyl, C$_{3-7}$ heterocycloalkyl, C$_{3-7}$ heterocycloalkyl(C$_{1-6}$)alkyl, aryl, aryl(C$_{1-6}$)alkyl, heteroaryl or heteroaryl(C$_{1-6}$)alkyl, any of which groups may be optionally substituted by one or more substituents.

Appositely, Z represents C$_{1-6}$ alkyl, C$_{2-6}$ alkenyl, C$_{3-7}$ cycloalkyl, C$_{3-7}$ cycloalkyl(C$_{1-6}$)alkyl, C$_{3-7}$ heterocycloalkyl, C$_{3-7}$ heterocycloalkyl(C$_{1-6}$)alkyl, aryl, aryl(C$_{1-6}$)alkyl, heteroaryl or heteroaryl(C$_{1-6}$)alkyl, any of which groups may be optionally substituted by one or more substituents.

Typically, Z represents C$_{1-6}$ alkyl, C$_{3-7}$ cycloalkyl, C$_{3-7}$ cycloalkyl(C$_{1-6}$)alkyl, C$_{3-7}$ heterocycloalkyl, C$_{3-7}$ heterocycloalkyl(C$_{1-6}$)alkyl, aryl, aryl(C$_{1-6}$)alkyl, heteroaryl or heteroaryl(C$_{1-6}$)alkyl, any of which groups may be optionally substituted by one or more substituents.

Suitably, Z represents C$_{1-6}$ alkyl, C$_{3-7}$ cycloalkyl(C$_{1-6}$) alkyl, C$_{3-7}$ heterocycloalkyl-(C$_{1-6}$)alkyl, aryl, aryl(C$_{1-6}$) alkyl, heteroaryl or heteroaryl(C$_{1-6}$)alkyl, any of which groups may be optionally substituted by one or more substituents.

In a first embodiment, Z represents hydrogen. In a second embodiment, Z represents optionally substituted C$_{1-6}$ alkyl. In a third embodiment, Z represents optionally substituted C$_{2-6}$ alkenyl. In a fourth embodiment, Z represents optionally substituted C$_{3-7}$ cycloalkyl. In a fifth embodiment, Z represents optionally substituted C$_{3-7}$ cycloalkyl(C$_{1-6}$)alkyl. In a sixth embodiment, Z represents optionally substituted C$_{3-7}$ heterocycloalkyl. In a seventh embodiment, Z represents optionally substituted C$_{3-7}$ heterocycloalkyl(C$_{1-6}$)alkyl. In an eighth embodiment, Z represents optionally substituted aryl. In a ninth embodiment, Z represents optionally substituted aryl(C$_{1-6}$)alkyl. In a tenth embodiment, Z represents optionally substituted heteroaryl. In an eleventh embodiment, Z represents optionally substituted heteroaryl(C$_{1-6}$)alkyl.

Suitable values of Z include methyl, cyclopentylethyl, morpholinylmethyl, phenyl, benzyl, phenylethyl, pyrazolyl, indazolyl, isoxazolyl, imidazolyl, benzimidazolyl, imidazo[1,2-a]pyridinyl, pyridinyl, quinolinyl, isoquinolinyl, pyrazinyl, quinoxalinyl, pyridinylmethyl, furylethyl, benzimidazolylethyl and pyridinylethyl, any of which groups may be optionally substituted by one or more substituents. Additional values include ethyl, isopropenyl, cyclopropyl, indanyl, cyclopropylmethyl, pyrrolidinyl, dihydrobenzofuranyl, indolinyl, dihydrobenzofuranylmethyl, morpholinylethyl, furyl, thienyl, indolyl, thiazolyl, benzothiazolyl, pyridazinyl, pyrimidinyl, indolylmethyl, thiazolylmethyl and imidazo[2,1-b]thiazolylmethyl, any of which groups may be optionally substituted by one or more substituents.

In a particular embodiment, Z is other than hydrogen.

In one embodiment, Z is unsubstituted. In another embodiment, Z is substituted by one or more substituents, typically by one, two or three substituents, suitably by one or two substituents. In one aspect of that embodiment, Z is monosubstituted. In another aspect of that embodiment, Z is disubstituted. In a further aspect of that embodiment, Z is trisubstituted.

Typical examples of optional substituents on Z include one or more substituents independently selected from halogen, cyano, nitro, C$_{1-6}$ alkyl, trifluoromethyl, hydroxy, oxo, C$_{1-6}$ alkoxy, difluoromethoxy, trifluoromethoxy, aryloxy, haloaryloxy, (C$_{1-6}$)alkoxyaryloxy, C$_{1-3}$ alkylenedioxy, C$_{1-6}$ alkylthio, C$_{1-6}$ alkylsulfonyl, C$_{1-6}$ alkylsulfonyl, amino, C$_{1-6}$ alkylamino, di(C$_{1-6}$)alkylamino, arylamino, C$_{2-6}$ alkylcarbonylamino, C$_{2-6}$ alkoxycarbonylamino, C$_{1-6}$ alkylsulfonylamino, formyl, C$_{2-6}$ alkylcarbonyl, C$_{3-6}$ cycloalkyl-carbonyl, C$_{3-6}$ heterocycloalkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulfonyl, C$_{1-6}$ alkylaminosulfonyl and di(C$_{1-6}$)alkylaminosulfonyl. Additional examples include cyano(C$_{1-6}$)alkyl, (C$_{3-7}$)heterocycloalkyl, halo(C$_{3-7}$)heterocycloalkyl, (C$_{1-6}$)alkyl(C$_{3-7}$)heterocycloalkyl, (C$_{2-6}$)alkoxycarbonyl(C$_{3-7}$)heterocycloalkyl, dihalo(C$_{3-7}$)heterocycloalkyl, (C$_{3-7}$)heterocycloalkyl(C$_{1-6}$)alkyl, (C$_{1-6}$)alkyl(C$_{3-7}$)heterocycloalkyl(C$_{1-6}$)alkyl, heteroaryl, (C$_{3-7}$)heterocycloalkoxy, (C$_{2-6}$)alkoxycarbonyl(C$_{3-7}$)heterocycloalkoxy, (C$_{3-7}$)heterocycloalkyl(C$_{1-6}$)alkoxy, dihalo(C$_{1-3}$)alkylenedioxy, arylcarbonyloxy, di(C$_{1-6}$)alkylamino(C$_{1-6}$)alkyl and aryloxycarbonyl.

Selected examples of optional substituents on Z include one or more substituents independently selected from halogen, cyano, nitro, C$_{1-6}$ alkyl, trifluoromethyl, cyano-(C$_{1-6}$) alkyl, (C$_{3-7}$)heterocycloalkyl, halo(C$_{3-7}$)heterocycloalkyl, (C$_{1-6}$)alkyl(C$_{3-7}$)-heterocycloalkyl, (C$_{2-6}$)alkoxycarbonyl (C$_{3-7}$)heterocycloalkyl, dihalo(C$_{3-7}$)-heterocycloalkyl, (C$_{3-7}$)heterocycloalkyl(C$_{1-6}$)alkyl, (C$_{1-6}$)alkyl(C$_{3-7}$)heterocycloalkyl-(C$_{1-6}$)alkyl, heteroaryl, hydroxy, oxo, C$_{1-6}$ alkoxy, difluoromethoxy, trifluoromethoxy, (C$_{3-7}$)heterocycloalkoxy, (C$_{2-6}$)alkoxycarbonyl(C$_{3-7}$)heterocycloalkoxy, (C$_{3-7}$)-heterocycloalkyl(C$_{1-6}$)alkoxy, aryloxy, haloaryloxy, (C$_{1-6}$)alkoxyaryloxy, C$_{1-3}$ alkylenedioxy, dihalo(C$_{1-3}$)alkylenedioxy, arylcarbonyloxy, di(C$_{1-6}$)alkylamino, di(C$_{1-6}$)-alkylamino(C$_{1-6}$)alkyl, C$_{2-6}$ alkylcarbonylamino, C$_{2-6}$ alkoxycarbonyl, aryloxycarbonyl and aminocarbonyl.

Suitable examples of optional substituents on Z include one or more substituents independently selected from halogen, C$_{1-6}$ alkyl, hydroxy, C$_{1-6}$ alkoxy, difluoromethoxy, trifluoromethoxy, aryloxy, (C$_{1-6}$)alkoxyaryloxy, C$_{1-3}$ alkylenedioxy and di(C$_{1-6}$)alkylamino.

Typical examples of specific substituents on Z include fluoro, chloro, bromo, cyano, nitro, methyl, isopropyl, trifluoromethyl, hydroxy, oxo, methoxy, difluoromethoxy, trifluoromethoxy, phenoxy, chlorophenoxy, methoxyphenoxy, methylenedioxy, ethylenedioxy, methylthio, methylsulfinyl, methylsulfonyl, amino, methylamino, tert-butylamino, dimethylamino, phenylamino, acetylamino, methoxycarbonylamino, methylsulfonylamino, formyl, acetyl, cyclopropylcarbonyl, azetidinylcarbonyl, pyrrolidinylcarbonyl, piperidinylcarbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylamino-sulfonyl. Additional examples include ethyl, tert-butyl, cyanomethyl, azetidinyl, pyrrolidinyl, piperazinyl, morpholinyl, fluoroazetidinyl, fluoropyrrolidinyl, methylpiperazinyl, tert-butoxycarbonylpiperazinyl, difluoroazetidinyl, difluoropyrrolidinyl, difluoropiperidinyl, pyrrolidinylmethyl, piperidinylmethyl, morpholinylmethyl, methylpiperazinylmethyl, pyrazolyl, imidazolyl, oxetanyloxy, azetidinyloxy, tetrahydrofuranyloxy, pyrrolidinyloxy, tert-butoxycarbonylazetidinyloxy, tert-butoxycarbonylpyrrolidinyloxy, tetrahydrofuranylmethoxy, morpholinylethoxy, difluoromethylenedioxy, benzoyloxy, dimethylaminomethyl, ethoxycarbonyl, tert-butoxycarbonyl and benzyloxycarbonyl.

Selected examples of specific substituents on Z include fluoro, chloro, cyano, nitro, methyl, ethyl, tert-butyl, trifluoromethyl, cyanomethyl, azetidinyl, pyrrolidinyl, piperazinyl, morpholinyl, fluoroazetidinyl, fluoropyrrolidinyl, methylpiperazinyl, tert-butoxycarbonylpiperazinyl, difluoroazetidinyl, difluoropyrrolidinyl, difluoropiperidinyl, pyrrolidinylmethyl, piperidinylmethyl, morpholinylmethyl, methylpiperazinylmethyl, pyrazolyl, imidazolyl, hydroxy, oxo, methoxy, difluoromethoxy, trifluoromethoxy, oxetanyloxy, azetidinyloxy, tetrahydrofuranyloxy, pyrrolidinyloxy, tert-butoxycarbonylazetidinyloxy, tert-butoxycarbonylpyrrolidinyloxy, tetrahydrofuranylmethoxy, morpholinylethoxy, phenoxy, chlorophenoxy, methoxyphenoxy, methylenedioxy, ethylenedioxy, difluoromethylenedioxy, benzoyloxy, dimethylamino, dimethylaminomethyl, acetylamino, ethoxycarbonyl, tert-butoxycarbonyl, benzyloxycarbonyl and aminocarbonyl.

Suitable examples of specific substituents on Z include fluoro, methyl, hydroxy, methoxy, difluoromethoxy, trifluoromethoxy, phenoxy, methoxyphenoxy, ethylenedioxy and dimethylamino.

Selected values of Z include phenoxymethyl, chlorophenoxymethyl, methoxyphenoxymethyl, tert-butoxycarbonylmethyl, benzyloxycarbonylmethyl, phenoxyethyl, isopropenyl, cyclopropyl, indanyl, cyclopropylmethyl, cyclopentylethyl, (methyl)(oxo)pyrrolidinyl, dihydrobenzofuranyl, methylindolinyl, dihydrobenzofuranylmethyl, morpholinylmethyl, morpholinylethyl, phenyl, nitrophenyl, methylphenyl, ethylphenyl, cyanomethylphenyl, morpholinylphenyl, pyrazolylphenyl, imidazolylphenyl, methoxyphenyl, difluoromethoxyphenyl, trifluoromethoxyphenyl, morpholinylethoxy-phenyl, ethylenedioxyphenyl, difluoromethylenedioxyphenyl, benzoyloxyphenyl, dimethylaminophenyl, acetylaminophenyl, aminocarbonylphenyl, (chloro)(methyl)-phenyl, dimethylphenyl, (methyl)(trifluoromethyl)phenyl, bis(trifluoromethyl)phenyl, (fluoropyrrolidinyl)(methyl)phenyl, (methyl)(pyrrolidinylmethyl)phenyl, (methyl)-(morpholinylmethyl)phenyl, (methyl)(methylpiperazinylmethyl)phenyl, (fluoro)-(methoxy) phenyl, (chloro)(methoxy)phenyl, (cyano)(methoxy)phenyl, (methoxy)-(methyl)phenyl, (methoxy)(trifluoromethyl)phenyl, dimethoxyphenyl, (difluoromethoxy)-(methyl)phenyl, (methyl)(oxetanyloxy)phenyl, (azetidinyloxy)(methyl)phenyl, (tert-butoxycarbonylazetidinyloxy)(methyl)phenyl, (methyl)(tetrahydrofuranylmethoxy)-phenyl, (methyl)(morpholinylethoxy)phenyl, (dimethylaminomethyl)(methyl) phenyl, trimethoxyphenyl, benzyl, cyanobenzyl, methylbenzyl, methoxybenzyl, methylenedioxy-benzyl, dimethylaminobenzyl, dimethoxybenzyl, phenylethyl, fluorophenylethyl, methylphenylethyl, (hydroxy)(phenyl)ethyl, methoxyphenylethyl, methylfuryl, thienyl, methylindolyl, pyrazolyl, methylpyrazolyl, dimethylpyrazolyl, indazolyl, dimethylisoxazolyl, thiazolyl, methylthiazolyl, tert-butylthiazolyl, ethoxycarbonylthiazolyl, benzothiazolyl, methoxybenzothiazolyl, methylimidazolyl, benzimidazolyl, methylbenzimidazolyl, trifluoromethylbenzimidazolyl, piperidinylmethylbenzimidazolyl, morpholinylmethylbenzimidazolyl, imidazo[1,2-a]pyridinyl, pyridinyl, chloropyridinyl, methylpiperazinylpyridinyl, methoxypyridinyl, dimethylpyridinyl, (methyl)-(trifluoromethyl)pyridinyl, (azetidinyl)(methyl)pyridinyl, (methyl)(pyrrolidinyl)pyridinyl, (methyl)(piperazinyl)pyridinyl, (fluoroazetidinyl)(methyl)pyridinyl, (fluoropyrrolidinyl)-(methyl)pyridinyl, (methyl)(methylpiperazinyl)pyridinyl, (tert-butoxycarbonyl-piperazinyl)(methyl)pyridinyl, (difluoroazetidinyl)(methyl)pyridinyl, (difluoro-pyrrolidinyl)(methyl)pyridinyl, (difluoropiperidinyl)(methyl)pyridinyl, (methyl)-(pyrrolidinylmethyl)pyridinyl, (methyl)(morpholinylmethyl)pyridinyl, (methyl)-(methylpiperazinylmethyl)pyridinyl, (chloro)(methoxy)pyridinyl, (methoxy)(methyl)-pyridinyl, (methoxy)(trifluoromethyl) pyridinyl, dimethoxypyridinyl, (difluoromethoxy)-(methyl) pyridinyl, (methyl)(tetrahydrofuranyloxy)pyridinyl, (methyl)(pyrrolidinyloxy)-pyridinyl, (tert-butoxycarbonylazetidinyloxy)(methyl)pyridinyl, (tert-butoxycarbonyl-pyrrolidinyloxy)(methyl)pyridinyl, (dimethylamino)(methyl)pyridinyl, quinolinyl, isoquinolinyl, methoxypyridazinyl, pyrimidinyl, methoxypyrimidinyl, (methoxy)-(methyl)pyrimidinyl, pyrazinyl, methoxypyrazinyl, (methoxy)(methyl)pyrazinyl, quinoxalinyl, indolylmethyl, thiazolylmethyl, methylthiazolylmethyl, imidazo[2,1-b]-thiazolylmethyl, pyridinylmethyl, furylethyl, benzimidazolylethyl and pyridinylethyl.

Specific values of Z include phenoxymethyl, methoxyphenoxymethyl, cyclopentylethyl, morpholinylmethyl, phenyl, methylphenyl, methoxyphenyl, difluoromethoxyphenyl, trifluoromethoxyphenyl, ethylenedioxyphenyl, dimethylaminophenyl, (methoxy)(methyl)phenyl, dimethoxyphenyl, trimethoxyphenyl, benzyl, methoxybenzyl, phenylethyl, fluorophenylethyl, methylphenylethyl, (hydroxy)(phenyl) ethyl, methoxyphenylethyl, pyrazolyl, methylpyrazolyl, indazolyl, dimethylisoxazolyl, methylimidazolyl, benzimidazolyl, imidazo[1,2-a]pyridinyl, pyridinyl, quinolinyl, isoquinolinyl, pyrazinyl, quinoxalinyl, pyridinylmethyl, furylethyl, benzimidazolylethyl and pyridinylethyl.

One particular value of Z is methoxyphenyl, especially 4-methoxyphenyl.

Another particular value of Z is (methoxy)(methyl)phenyl, especially 4-methoxy-2-methylphenyl.

Another particular value of Z is (difluoroazetidinyl)(methyl)pyridinyl, especially 6-(3,3-difluoroazetidin-1-yl)-2-methylpyridin-3-yl.

Typically, $A^1$ represents hydrogen or cyano; or $A^1$ represents $C_{1-6}$ alkyl, optionally substituted by one or more substituents independently selected from —$OR^a$, —$CO_2R^d$ and —$CONR^bR^c$; or $A^1$ represents $C_{3-7}$ cycloalkyl.

Suitable values of $A^1$ include hydrogen, methyl and trifluoromethyl.

In a particular embodiment, $A^1$ represents hydrogen. In another embodiment, $A^1$ represents cyano. In another embodiment, $A^1$ represents trifluoromethyl. In a further embodiment, $A^1$ represents $C_{1-6}$ alkyl, optionally substituted by one or more substituents independently selected from —$OR^a$, —$NR^bR^c$, —$CO_2R^d$ and —$CONR^bR^c$. In one aspect of that embodiment, $A^1$ represents $C_{1-6}$ alkyl, optionally substituted by one or more substituents independently selected from —$OR^a$, —$CO_2R^d$ and —$CONR^bR^c$. In another aspect of that embodiment, $A^1$ represents $C_{1-6}$ alkyl, optionally substituted by one or more substituents independently selected from —$OR^a$ and —$NR^bR^c$. In another aspect of that embodiment, $A^1$ represents unsubstituted $C_{1-6}$ alkyl, typically methyl, ethyl, isopropyl or isobutyl, especially methyl. In another aspect of that embodiment, $A^1$ represents $C_{1-6}$ alkyl monosubstituted by —$OR^a$, —$CO_2R^d$ or —$CONR^bR^c$. In another aspect of that embodiment, $A^1$ represents $C_{1-6}$ alkyl monosubstituted by —$OR^a$ or —$NR^bR^c$. In a further aspect of that embodiment, $A^1$ represents $C_{1-6}$ alkyl disubstituted by two substituents independently selected from —$OR^a$ and —$NR^bR^c$. In an additional embodiment, $A^1$ represents $C_{3-7}$ cycloalkyl, especially cyclopropyl.

Selected values of $A^1$ include hydrogen, cyano, methyl, ethyl, isopropyl, isobutyl, —$CH_2OR^a$, —$CH_2CH_2OR^a$, —$CH_2CO_2R^d$, —$CH_2CONR^bR^c$ and cyclopropyl.

Particular values of $A^1$ include hydrogen, methyl and hydroxymethyl.

In a particular embodiment, $A^2$ represents hydrogen. In another embodiment, $A^2$ represents $C_{1-6}$ alkyl, especially methyl.

Selected values of $A^2$ include hydrogen and methyl.

Suitably, $R^1$ represents hydrogen, halogen, cyano, nitro, hydroxy, trifluoromethyl, trifluoromethoxy, —$OR^a$, —$SO_2R^a$, —$NR^bR^c$, —$CH_2NR^bR^c$, —$NR^cCOR^d$, —$CH_2NR^cCOR^d$, —$NR^cCO_2R^d$, —$NHCONR^bR^c$, —$NR^cSO_2R^e$, —$NHSO_2NR^bR^c$, —$COR^d$, —$CO_2R^d$, —$CONR^bR^c$, —$CON(OR^a)R^b$ or —$SO_2NR^bR^c$; or $C_{1-6}$ alkyl, aryl or heteroaryl, any of which groups may be optionally substituted by one or more substituents.

Typically, $R^1$ represents hydrogen, —$NR^bR^c$ or —$NR^cCOR^d$; or $C_{1-6}$ alkyl, which group may be optionally substituted by one or more substituents.

Suitable values of $R^1$ include hydrogen and —$NR^bR^c$, especially —$NR^bR^c$.

In one embodiment, $R^1$ represents hydrogen. In another embodiment, $R^1$ represents —$NR^bR^c$. In a further embodiment, $R^1$ represents —$NR^cCOR^d$. In an additional embodiment, $R^1$ represents optionally substituted $C_{1-6}$ alkyl. In one aspect of that embodiment, $R^1$ represents optionally substituted methyl.

Examples of typical substituents on $R^1$ include one or more substituents independently selected from halogen, cyano, nitro, $C_{1-6}$ alkyl, trifluoromethyl, aryl($C_{1-6}$)alkyl, hydroxy, $C_{1-6}$ alkoxy, difluoromethoxy, trifluoromethoxy, aryloxy, $C_{1-4}$ alkylenedioxy, $C_{1-6}$ alkoxy($C_{1-6}$)alkyl, $C_{1-6}$ alkylthio, $C_{1-6}$ alkylsulphonyl, oxo, amino, $C_{1-6}$ alkylamino, di($C_{1-6}$)alkylamino, $C_{2-6}$ alkylcarbonylamino, $C_{2-6}$ alkoxycarbonylamino, aryl($C_{1-6}$)alkoxycarbonylamino, $C_{1-6}$ alkylaminocarbonylamino, arylaminocarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylamino sulphonyl and di($C_{1-6}$)alkylaminosulphonyl.

Specific examples of typical substituents on $R^1$ include one or more substituents independently selected from fluoro, chloro, bromo, cyano, nitro, methyl, ethyl, tert-butyl, trifluoromethyl, benzyl, hydroxy, methoxy, difluoromethoxy, trifluoromethoxy, phenoxy, methylenedioxy, ethylenedioxy, methoxymethyl, methylthio, methylsulphonyl, oxo, amino, methylamino, dimethylamino, acetylamino, methoxycarbonylamino, ethoxycarbonylamino, benzyloxycarbonylamino, ethylaminocarbonylamino, butylaminocarbonylamino, phenylaminocarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl.

Suitably, $R^2$ represents hydrogen or $C_{1-6}$ alkyl.

Suitable values of $R^2$ include hydrogen and methyl.

In one embodiment, $R^2$ represents hydrogen. In another embodiment, $R^2$ represents $C_{1-6}$ alkyl, optionally substituted by one or more substituents independently selected from —$OR^a$ and —$NR^bR^c$. In one aspect of that embodiment, $R^2$ represents unsubstituted $C_{1-6}$ alkyl, especially methyl. In another aspect of that embodiment, $R^2$ represents $C_{1-6}$ alkyl monosubstituted by —$OR^a$ or —$NR^bR^c$. In a further aspect of that embodiment, $R^2$ represents $C_{1-6}$ alkyl disubstituted by two substituents independently selected from —$OR^a$ and —$NR^bR^c$.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, acetylaminomethyl, tert-butoxycarbonylamino, methylsulphonylamino, aminocarbonyl, methylaminocarbonyl and dimethylaminocarbonyl.

Typically, $R^a$ represents hydrogen; or $R^a$ represents $C_{1-6}$ alkyl, aryl($C_{1-6}$)alkyl or heteroaryl($C_{1-6}$)alkyl, any of which groups may be optionally substituted by one or more substituents.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Apposite values of $R^a$ include hydrogen; and methyl, ethyl, benzyl or isoindolylpropyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents hydrogen. In another embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

Appositely, $R^a$ represents hydrogen or $C_{1-6}$ alkyl.

Individual values of $R^a$ include hydrogen and methyl.

In a particular aspect, $R^b$ represents hydrogen or trifluoromethyl; or $C_{1-6}$ alkyl, $C_{3-7}$ cycloalkyl, $C_{3-7}$ cycloalkyl ($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl ($C_{1-6}$)alkyl, $C_{3-7}$ heterocycloalkyl or $C_{3-7}$ heterocycloalkyl ($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino ($C_{1-6}$)alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, amino azetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl or ethyl, particularly methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, ethyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Appositely, $R^d$ represents hydrogen or $C_{1-6}$ alkyl.

Individual values of $R^d$ include hydrogen and methyl.

A particular value of $R^d$ is ethyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

In a particular aspect, the present invention provides a compound of formula (IA), or a pharmaceutically acceptable salt or solvate thereof:

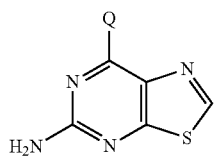
(IA)

wherein Q is as defined above.

One sub-class of compounds according to the invention is represented by the compounds of formula (IIA), and pharmaceutically acceptable salts and solvates thereof:

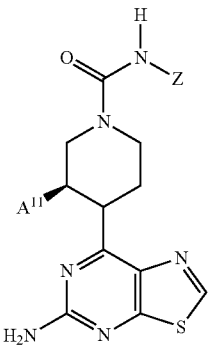
(IIA)

wherein $A^{11}$ represents hydrogen, cyano, $C_{1-6}$ alkyl, $-CH_2OR^a$, $-CH_2CH_2OR^a$, $-CH_2CO_2R^d$, $-CH_2CONR^bR^c$ or $C_{3-7}$ cycloalkyl; and Z, $R^a$, $R^b$, $R^c$ and $R^d$ are as defined above.

In a first embodiment, $A^{11}$ represents hydrogen. In a second embodiment, $A^{11}$ represents cyano. In a third embodiment, $A^{11}$ represents $C_{1-6}$ alkyl, typically methyl, ethyl, isopropyl or isobutyl, especially methyl. In a fourth embodiment, $A^{11}$ represents $-CH_2OR^a$. In a fifth embodiment, $A^1$ represents $-CH_2CH_2OR^a$. In a sixth embodiment, $A^{11}$ represents $-CH_2CO_2R^d$. In a seventh embodiment, $A^{11}$ represents $-CH_2CONR^bR^c$. In an eighth embodiment, $A^{11}$ represents $C_{3-7}$ cycloalkyl, especially cyclopropyl.

Selected values of $A^{11}$ include hydrogen, cyano, methyl, ethyl, isopropyl, isobutyl, $-CH_2OR^a$, $-CH_2CH_2OR^a$, $-CH_2CO_2R^d$, $-CH_2CONR^bR^c$ and cyclopropyl.

Particular values of $A^{11}$ include hydrogen, methyl and hydroxymethyl.

Another sub-class of compounds according to the invention is represented by the compounds of formula (IIB), and pharmaceutically acceptable salts and solvates thereof:

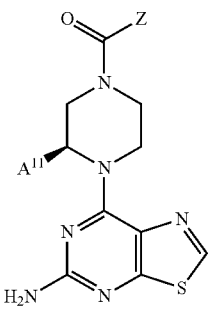
(IIB)

wherein Z and $A^{11}$ are as defined above.

A further sub-class of compounds according to the invention is represented by the compounds of formula (IIC), and pharmaceutically acceptable salts and solvates thereof:

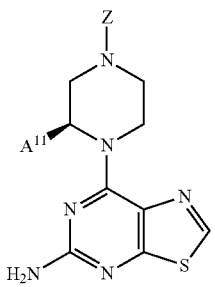

(IIC)

wherein Z and A$^{11}$ are as defined above.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments. These include inflammatory, autoimmune and oncological disorders; viral diseases; and organ and cell transplant rejection.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis and spontaneous infertility.

Oncological disorders, which may be acute or chronic, include proliferative disorders, especially cancer, in animals, including mammals, especially humans. Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle.

Viral diseases include infections caused by various families of virus, including the Retroviridae, Flaviviridae, Picornaviridae. Various genera within the Retroviridae family include Alpharetrovirus, Betaretrovirus, Gammaretrovirus, Deltaretrovirus, Epsilonretrovirus, Lentivirus and Spumavirus. Members of the Lentivirus genus include human immunodeficiency virus 1 (HIV-1) and human immunodeficiency virus 2 (HIV-2). Various genera within the Flaviviridae family include Flavivirus, Pestivirus, Hepacivirus and Hepatitis G Virus. Members of the Flavivirus genus include Dengue fever virus, yellow fever virus, West Nile encephalitis virus and Japanese encephalitis virus. Members of the Pestivirus genus include bovine viral diarrhoea virus (BVDV), classical swine fever virus and border disease virus 2 (BDV-2). Members of the Hepacivirus genus include hepatitis C virus (HCV). Members of the Hepatitis G Virus genus include hepatitis G virus. Various genera within the Picornaviridae family include Aphthovirus, Avihepatovirus, Cardiovirus, Enterovirus, Erbovirus, Hepatovirus, Kobuvirus, Parechovirus, Sapelovirus, Senecavirus, Teschovirus and Tremovirus. Members of the Enterovirus genus include poliovirus, coxsackie A virus, coxsackie B virus and rhinovirus.

Organ transplant rejection includes the rejection of transplanted or grafted organs or cells (both allografts and xenografts), including graft-versus-host reaction disease. The term "organ" as used herein means all organs or parts of organs in mammals, particularly humans, including kidney, lung, bone marrow, hair, cornea, eye (vitreous), heart, heart valve, liver, pancreas, blood vessel, skin, muscle, bone, intestine and stomach. The term "rejection" as used herein means all reactions of the recipient body or the transplanted organ which ultimately lead to cell or tissue death in the transplanted organ, or adversely affect the functional ability and viability of the transplanted organ or the recipient. In particular, this means acute and chronic rejection reactions.

Cell transplant rejection includes the rejection of cell transplants and xenotransplantation. The major hurdle for xenotransplantation is that even before the T lymphocytes (responsible for the rejection of allografts) are activated, the innate immune system (especially T-independent B lymphocytes and macrophages) is activated. This provokes two types of severe and early acute rejection, referred to as hyperacute rejection and vascular rejection respectively. Conventional immunosuppressant drugs, including cyclosporine A, are ineffective in xenotransplantation. The compounds in accordance with the present invention are not liable to this drawback. The ability of the compounds of this invention to suppress T-independent xeno-antibody production as well as macrophage activation may be demonstrated by their ability to prevent xenograft rejection in athymic, T-deficient mice receiving xenogenic hamster-heart grafts.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III):

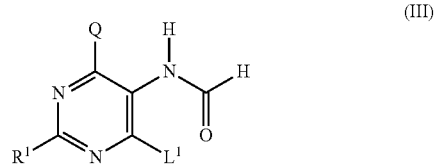

(III)

wherein Q and $R^1$ are as defined above, and $L^1$ represents a suitable leaving group; with Lawesson's reagent, i.e. 2,4-bis(4-methoxyphenyl)-1,3-dithia-2,4-diphosphetane-2,4-disulfide.

The leaving group $L^1$ is typically a halogen atom, e.g. chloro.

The reaction is conveniently effected at an elevated temperature in a suitable solvent, e.g. a cyclic ether solvent such as tetrahydrofuran.

The intermediates of formula (III) above may be prepared by a process which comprises reacting a compound of formula (IV) with a compound of formula (V):

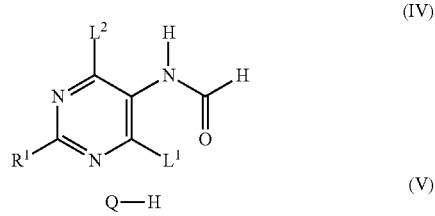

(IV)

(V)

wherein Q, $R^1$ and $L^1$ are as defined above, and $L^2$ represents a suitable leaving group.

The leaving group $L^2$ is typically a halogen atom, e.g. chloro.

The reaction will generally be carried out in the presence of a base, typically an organic amine such as N,N-diisopropylethylamine. The reaction is conveniently effected at an elevated temperature in a suitable solvent, e.g. a cyclic ether solvent such as 1,4-dioxane, or a dipolar aprotic solvent such as N,N-dimethylformamide.

In an alternative procedure, the compounds of formula (I) above may be prepared by a process which comprises reacting a compound of formula (V) as defined above with a compound of formula (VI):

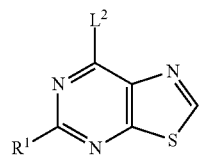

(VI)

wherein $R^1$ and $L^2$ are as defined above; under conditions analogous to those described above for the reaction between compounds (IV) and (V). Alternatively, the reaction may be effected at an elevated temperature in a suitable solvent, e.g. a chlorinated solvent such as chloroform, in the presence of a catalytic quantity of p-toluenesulfonic acid.

In a further procedure, the compounds of formula (I) above wherein Y represents —C(O)—, —S(O)$_2$— or —C(O)O— may be prepared by a process which comprises reacting a compound of formula $L^3$-C(O)—Z, $L^3$-S(O)$_2$—Z or $L^3$-C(O) O—Z respectively with a compound of formula (VIIA), (VIIB), (VIIC), (VIID) or (VIIE):

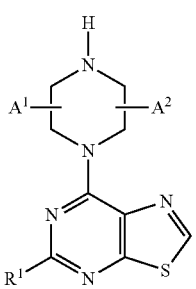

(VIIA)

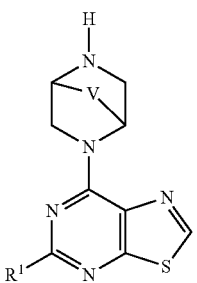

(VIIB)

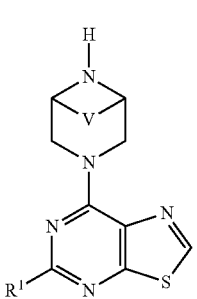

(VIIC)

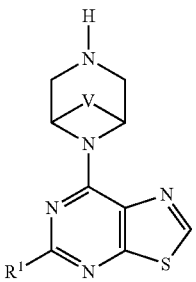

(VIID)

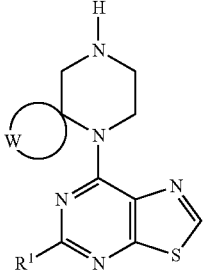

(VIIE)

wherein V, W, Z, $A^1$, $A^2$ and $R^1$ are as defined above, and $L^3$ represents a suitable leaving group.

The leaving group $L^3$ is typically a halogen atom, e.g. chloro.

The reaction is conveniently effected at ambient temperature in a suitable solvent, e.g. an ethereal solvent such as 1,4-dioxane, or a chlorinated solvent such as dichloromethane, typically in the presence of a base. A suitable base for use in the reaction may be an organic base such as N,N-diisopropylethylamine, or an inorganic base such as potassium carbonate.

Alternatively, the leaving group $L^3$ may be 2-methyl-3-(trifluoromethylsulfonyl)-1H-imidazol-3-ium-1-yl, in which case the reaction may conveniently be effected at ambient temperature in an organic solvent such as acetonitrile.

In a variant procedure, the compounds of formula (I) above wherein Y represents —C(O)— may be prepared by a process which comprises reacting a compound of formula (VIIA), (VIIB), (VIIC), (VIID) or (VIIE) as defined above with a compound of formula Z—CO$_2$H.

The reaction is conveniently effected at ambient temperature in a suitable solvent, e.g. a dipolar aprotic solvent such as N,N-dimethylformamide, typically in the presence of a coupling reagent and a base. A suitable coupling reagent for use in the reaction may be O-(7-azabenzotriazol-1-yl)-N,N,N', N'-tetramethyluronium hexafluorophosphate (HATU). A suitable base for use in the reaction may be an organic base such as N,N-diisopropylethylamine.

In another procedure, the compounds of formula (I) above wherein Y represents —C(O)NH— may be prepared by a process which comprises reacting a compound of formula (VIIA), (VIIB), (VIIC), (VIID) or (VIIE) as defined above with an isocyanate derivative of formula Z—N=C=O, wherein Z is as defined above.

The reaction is conveniently effected at ambient temperature in a suitable solvent or mixture of solvents. Such solvent or solvents may typically be selected as appropriate from an ethereal solvent such as 1,4-dioxane or tetrahydrofuran, a chlorinated solvent such as dichloromethane, a nitrile-containing solvent such as acetonitrile, and a dipolar aprotic solvent such as N,N-dimethylformamide. The reaction may optionally be performed in the presence of a base, e.g. an organic base such as diisopropylamine, N,N-diisopropylethylamine or triethylamine.

Alternatively, the compounds of formula (I) above wherein Y represents —C(O)NH— may be prepared by a process which comprises reacting a compound of formula (VIIA), (VIIB), (VIIC), (VIID) or (VIIE) as defined above with a compound of formula Z—NH$_2$, wherein Z is as defined above, in the presence of triphosgene or 1,1'-carbonyldiimidazole.

The reaction is conveniently effected at ambient temperature in a suitable solvent, e.g. a chlorinated solvent such as dichloromethane, or a dipolar aprotic solvent such as N,N-dimethylformamide, typically in the presence of a base, e.g. an organic base such as N,N-diisopropylethylamine.

Alternatively, the compounds of formula (I) above wherein Y represents —C(O)NH— may be prepared by a two-step process which comprises: (i) reacting a compound of formula Z—NH$_2$, wherein Z is as defined above, with phenyl chloroformate; and (ii) reacting the material thereby obtained with a compound of formula (VIIA), (VIIB), (VIIC), (VIID) or (VIIE) as defined above.

Step (i) of the above process is conveniently effected at a temperature in the region of 0° C. in a suitable solvent, e.g. a cyclic ether solvent such as tetrahydrofuran, typically in the presence of pyridine. Step (ii) is conveniently effected at an elevated temperature in a suitable solvent, e.g. a sulfoxide solvent such as dimethyl sulfoxide, typically in the presence of a base, e.g. an organic base such as N,N-diisopropylethylamine.

In a further procedure, the compounds of formula (I) above wherein Y represents —S(O$_2$)NH— may be prepared by a two-step process which comprises: (i) reacting a compound of formula (VIIA), (VIIB), (VIIC), (VIID) or (VIIE) as defined above with methyl trifluoromethanesulfonate; and (ii) reacting the material thereby obtained with a compound of formula Z—NH$_2$, wherein Z is as defined above.

Step (i) of the above process is conveniently effected at a temperature in the region of 0° C. in a suitable solvent, typically a chlorinated solvent such as dichloromethane. Step (ii) is conveniently effected at an elevated temperature in a suitable solvent, e.g. a nitrile-containing solvent such as acetonitrile.

In a further procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted $C_{3-7}$ heterocycloalkyl($C_{1-6}$)alkyl, optionally substituted aryl($C_{1-6}$)alkyl or optionally substituted heteroaryl($C_{1-6}$)alkyl, may be prepared by a process which comprises reacting a compound of formula (VIIA), (VIIB), (VIIC), (VIID) or (VIIE) as defined above with a compound of formula $Z^1$-$L^4$ wherein $Z^1$ represents $C_{1-6}$ alkyl, $C_{3-7}$ cycloalkyl($C_{1-6}$)alkyl, aryl($C_{1-6}$)alkyl, $C_{3-7}$ heterocycloalkyl($C_{1-6}$)alkyl or heteroaryl($C_{1-6}$)alkyl, any of which groups may be optionally substituted by one or more substituents, and $L^4$ represents a suitable leaving group.

The leaving group $L^4$ is typically a halogen atom.

The reaction is conveniently effected at ambient temperature in a suitable solvent, e.g. a dipolar aprotic solvent such as N,N-dimethylformamide, or a chlorinated solvent such as dichloromethane, typically in the presence of a base. A suitable base for use in the reaction may be an organic base such as triethylamine, or an inorganic base such as caesium carbonate.

In a variant procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted $C_{3-7}$ heterocycloalkyl($C_{1-6}$)alkyl, optionally substituted aryl($C_{1-6}$)alkyl or optionally substituted heteroaryl($C_{1-6}$)alkyl, may be prepared by a two-step process which comprises: (i) reacting a compound of formula (VIIA), (VIIB), (VIIC), (VIID) or (VIIE) as defined above with a compound of formula $Z^2$—CHO, wherein $Z^2$—CH$_2$— corresponds to a group of formula $Z^1$— as defined above; and (ii) reacting the material thereby obtained with a reducing agent.

Steps (i) and (ii) of the above process are conveniently effected at ambient temperature in a suitable solvent, e.g. a $C_{1-4}$ alkanol such as methanol. Step (i) is typically performed in the presence of a base, e.g. an organic base such as triethylamine. The reducing agent for use in step (ii) may suitably be an alkali metal borohydride such as sodium borohydride.

The compounds of formula (I) above wherein Y represents a linker group of formula (Ya) as defined above may be prepared by a process which comprises reacting a compound of formula (VIIA), (VIIB), (VIIC), (VIID) or (VIIE) as defined above with a compound of formula (VIII):

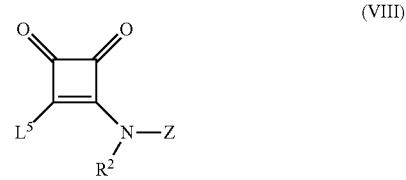

(VIII)

wherein Z and $R^2$ are as defined above, and $L^5$ represents a suitable leaving group.

The leaving group $L^5$ is typically a $C_{1-4}$ alkoxy group, e.g. ethoxy.

The reaction is conveniently effected at ambient temperature in a suitable solvent, e.g. a lower alkanol such as ethanol, typically in the presence of a base, e.g. an organic base such as triethylamine.

The intermediates of formula (VIIA), (VIIB), (VIIC), (VIID) or (VIIE) above may be prepared by reacting a compound of formula (VI) as defined above with a compound of formula (IXA), (IXB), (IXC), (IXD) or (IXE):

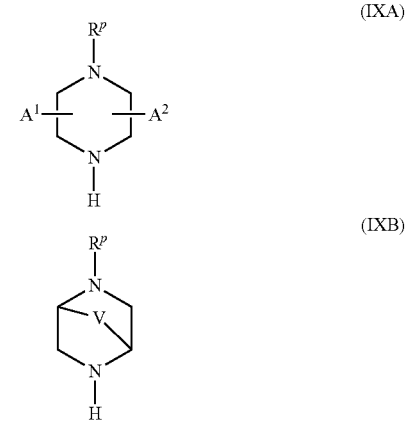

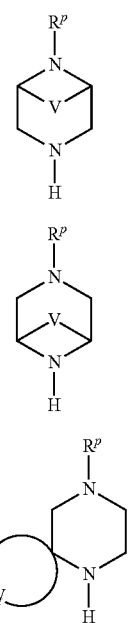

wherein V, W, $A^1$ and $A^2$ are as defined above, and $R^p$ represents hydrogen or an N-protecting group; followed, as necessary, by removal of the N-protecting group $R^p$.

The N-protecting group $R^p$ is typically tert-butoxycarbonyl (BOC).

The reaction between compound (VI) and compound (IXA), (IXB), (IXC), (IXD) or (IXE) is conveniently accomplished under conditions analogous to those described above for the reaction between compounds (V) and (VI).

Alternatively, the reaction between compound (VI) and compound (IXA), (IXB), (IXC), (IXD) or (IXE) may be accomplished at a suitable temperature (ambient or elevated) in a solvent such as acetonitrile or N,N-dimethylformamide, ideally in the presence of a coupling agent such as benzotriazol-1-yloxytris(dimethylamino)-phosphonium hexafluorophosphate (BOP) or (benzotriazol-1-yloxy)tripyrrolidinophosphonium hexafluorophosphate (PyBOP), and a base, e.g. an organic base such as 1,8-diazabicyclo[5.4.0]undec-7-ene (DBU).

Where the N-protecting group $R^p$ is BOC, subsequent removal of the BOC group may typically be accomplished by treatment with an acid, e.g. a mineral acid such as hydrochloric acid, or an organic acid such as trifluoroacetic acid. Alternatively, the BOC group may be removed by treatment with trimethylsilyl trifluoromethanesulfonate and 2,6-lutidine, typically at ambient temperature in a suitable solvent, e.g. a chlorinated solvent such as dichloromethane.

As will be appreciated, the intermediates of formula (VIIA), (VIIB), (VIIC), (VIID) and (VIIE) correspond to compounds in accordance with the present invention wherein Y represents a covalent bond and Z is hydrogen. Similarly, the intermediates of formula (IXA), (IXB), (IXC), (IXD) or (IXE) wherein $R^p$ is hydrogen correspond to intermediates of formula (V) wherein Y represents a covalent bond and Z is hydrogen. Likewise, the intermediates of formula (IXA), (IXB), (IXC), (IXD) or (IXE) wherein $R^p$ is BOC correspond to intermediates of formula (V) wherein Y represents —C(O) O— and Z is tert-butyl.

Where they are not commercially available, the starting materials of formula (IV), (V), (VI), (VIII), (IXA), (IXB), (IXC), (IXD) and (IXE) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) comprising a N—BOC moiety may be converted into the corresponding compound comprising a N—H moiety by treatment with an acid, e.g. a mineral acid such as hydrochloric acid, or an organic acid such as trifluoroacetic acid.

A compound of formula (I) comprising a —$CO_2H$ moiety may be converted into the corresponding compound comprising a —$CONH_2$ moiety by treatment with ammonium chloride, typically in the presence of a coupling agent such as 1-(3-dimethylaminopropyl)-3-ethylcarbodiimide hydrochloride (EDC) and an additive such as 1-hydroxybenzotriazole hydrate (HOBT), suitably in the presence of a base, e.g. an organic base such as diisopropylamine or N,N-diisopropylethylamine. Likewise, a compound of formula (I) comprising a —$CO_2H$ moiety may be converted into the corresponding compound comprising a —$CONR^bR^c$ moiety by treatment with an amine of formula H—$NR^bR^c$, typically in the presence of a coupling agent such as EDC and an additive such as HOBT, suitably in the presence of a base, e.g. an organic base such as diisopropylamine or N,N-diisopropylethylamine.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention are potent inhibitors when measured in the MLR test described below.

The Mixed Lymphocyte Reaction (MLR) Test

Human peripheral blood mononuclear cells (PBMCs) were isolated from buffy coats, obtained from healthy blood donors by Ficoll (Lymphoprep, Axis-Shield PoC AS, Oslo, Norway) density-gradient centrifugation. The cells at the Ficoll-plasma interface were washed three times and used as "Responder" cells. RPMI 1788 (ATCC, N° CCL-156) cells were treated with mitomycin C (Kyowa, Nycomed, Brussels, Belgium) and used as "Stimulator" cells. Responder cells (0.12×106), Stimulator cells (0.045×106) and compounds (in different concentrations) were cocultured for 6 days in RPMI 1640 medium (BioWhittaker, Lonza, Belgium) supplemented with 10% fetal calf serum, 100 U/ml Geneticin (Gibco, LifeTechnologies, UK). Cells were cultured in triplicate in flat-bottomed 96-well microtiter tissue culture plates (TTP, Switzerland). After 5 days, cells were pulsed with 1 µCi of methyl-$^3$H thymidine (MP Biomedicals, USA), harvested 18 h later on glass filter paper and counted. Proliferation values were expressed as counts per minute (cpm), and converted to % inhibition with respect to a blank MLR test (identical but without added compound). The IC$_{50}$ was determined from a graph with at least four points, each derived from the mean of 2 experiments. The IC$_{50}$ value represents the lowest concentration of test compound (expressed in µM) that resulted in a 50% inhibition of the MLR.

The compounds of the accompanying Examples were all found to generate IC$_{50}$ values in the MLR test of 10 µM or better.

EXAMPLES

| Abbreviations | |
|---|---|
| THF: tetrahydrofuran | MeOH: methanol |
| EtOH: ethanol | EtOAc: ethyl acetate |
| DMF: N,N-dimethylformamide | DMA: N,N-dimethylacetamide |
| DMSO: dimethylsulfoxide | DCM: dichloromethane |
| DIPEA: N,N-diisopropylethylamine | TFA: trifluoroacetic acid |
| HOBT: 1-hydroxybenzotriazole | CDI: 1,1'-carbonyldiimidazole |
| HATU: O-(7-azabenzotriazol-1-yl)-N,N,N',N'-tetramethyluronium hexafluorophosphate | |
| EDC: 1-[3-(dimethylamino)propyl]-3-ethylcarbodiimide | |
| TMSOTf: trimethylsilyl trifluoromethanesulfonate | |
| Lawesson's reagent: 2,4-bis(4-methoxyphenyl)-1,3-dithia-2,4-diphosphetane 2,4-disulfide | |
| h: hour | |
| MS: Mass Spectrometry | M: mass |
| LCMS: Liquid Chromatography Mass Spectrometry | |
| ES+: Electrospray Positive Ionisation | RT: retention time |

Analytical Methods
Method 1 (5 minutes)
Column: Waters X Bridge, 20×2.1 mm, 2.5 µm.
Column ID: E-AC-3/11/COL/035

Mobile Phase A: 10 mM ammonium formate in water+0.1% ammonia
Mobile Phase B: acetonitrile+5% solvent A+0.1% ammonia
Injection Volume: 5.0 µL; Flow Rate: 1.00 mL/minute
Gradient Program: 5% B to 95% B in 3.0 minutes; hold until 4.00 minutes; at 4.01 minutes B conc. is 5%; hold until 5 minutes.

Method 2

| High pH Solvent A2: | (approximately pH 9.5) 10 mM ammonium formate in water + 0.1% ammonia solution | | |
|---|---|---|---|
| Solvent B2: | acetonitrile + 5% solvent A2 + 0.1% ammonia solution | | |
| | Time | A % | B % |
| Gradient Program: | 0.00 | 95.0 | 5.0 |
| | 4.00 | 5.0 | 95.0 |
| | 5.00 | 5.0 | 95.0 |
| | 5.10 | 95.0 | 5.0 |

Method 3

| High pH Solvent A2: | (approximately pH 9.5) 10 mM ammonium formate in water + 0.1% ammonia solution | | |
|---|---|---|---|
| Solvent B2: | acetonitrile + 5% solvent A2 + 0.1% ammonia solution | | |
| | Time | A % | B % |
| Gradient Program: | 0.00 | 95.0 | 5.0 |
| | 1.50 | 5.0 | 95.0 |
| | 2.50 | 5.0 | 95.0 |
| | 3.00 | 95.0 | 5.0 |

Method 4

| Machine: | Waters 2795 | | |
|---|---|---|---|
| Column: | Waters X Bridge C18, 2.1 × 20 mm, 2.5 µm | | |
| | Time | A % | B % |
| Gradient Program: | 0 | 0 | 100 |
| | 0.18 | 5 | 95 |
| | 1.80 | 95 | 5 |
| | 2.04 | 95 | 5 |
| | 2.47 | 0 | 100 |
| | 3.10 | 0 | 100 |
| Mobile Phase: | Eluent B-acetonitrile | | |
| Eluent B: | pH 10 buffer, ammonium hydrogen carbonate | | |
| Run Time: | 3.1 minutes | | |
| Flow Rate: | 1 mL/minute | | |
| Temperature: | 25° C. | | |
| Injection Volume: | 5 µL | | |

Intermediate 1

4-[2-Amino-6-chloro-5-(formylamino)pyrimidin-4-yl]piperazine-1-carboxylic acid tert-butyl ester To a suspension of N-(2-amino-4,6-dichloropyrimidin-5-yl)formamide (10.0 g, 48.3 mmol) in 1,4-dioxane (400 mL) were added N,N-diisopropylethylamine (12.7 mL, 72.5 mmol) and piperazine-1-carboxylic acid tert-butyl ester (9.8 g, 53.1 mmol). The mixture was stirred at 55° C. for 1 h. The solvent was removed in vacuo and the residue was partitioned between DCM and water. The aqueous phase was extracted with further DCM and the combined organic fractions were washed with brine, then dried (Na$_2$SO$_4$) and evaporated in vacuo to give the title compound (17.1 g, 100%) as a white solid. LCMS (ES+) 357.4 (M+H)+, RT 1.08 minutes (method 3).

Intermediate 2

4-(5-Aminothiazolo[5,4-d]pyrimidin-7-yl)piperazine-1-carboxylic acid tert-butyl ester To a solution of Intermediate 1 (17.1 g, 48.0 mmol) in THF (400 mL) was added Lawesson's reagent (14.57 g, 36.0 mmol). The mixture was stirred at 70° C. for 1.5 h. The mixture was allowed to cool to room temperature and the resulting precipitate was filtered off, washing with EtOAc (×3) and diethyl ether (×3), to give the title compound (14.4 g, 89%) as a white solid. LCMS (ES+) 337.4 (M+H)+, RT 1.29 minutes (method 3).

Intermediate 3

7-(piperazin-1-yl)thiazolo[5,4-d]pyrimidin-5-ylamine hydrochloride

Intermediate 2 (12.4 g, 36.8 mmol) in THF (400 mL) was taken up in 4N HCl/1,4-dioxane. The mixture was stirred at room temperature for 1 h. The solvent was removed in vacuo to give the title compound (10.8 g, quant.) as an off-white solid. LCMS (ES+) 237.0 (M+H)+, RT 0.734 minutes (method 2).

Intermediate 4

7-Chlorothiazolo[5,4-d]pyrimidin-5-amine

To a solution of N-(2-amino-4,6-dichloropyrimidin-5-yl) formamide (12 g, 57 mmol) in THF (250 mL) was added Lawesson's reagent (17.5 g, 43 mmol). The reaction mixture was stirred at 65° C. for 30 minutes. The reaction mixture was then filtered, and the filtrate was concentrated. The crude yellow solid obtained was triturated using diethyl ether to afford the title compound (10 g, 93.4%) as a pale yellow solid. LCMS (ES+) 186.95 (M+H)+, RT 1.31 minutes (method 1).

Intermediate 5 tert-Butyl (3S)-4-(5-aminothiazolo[5,4-d]pyrimidin-7-yl)-3-methylpiperazine-1-carboxylate To a solution of Intermediate 4 (5 g, 26 mmol) in 1,4-dioxane (50 mL) was added DIPEA (7 mL, 40 mmol), followed by tert-butyl (3S)-3-methylpiperazine-1-carboxylate (5.9 g, 29 mmol). The reaction mixture was heated under microwave irradiation at 120° C. for 45 minutes. The reaction mixture was then concentrated, and diluted with DCM. The organic layer was washed with water and 5% aqueous acetic acid solution, then concentrated. The crude material obtained was purified by column chromatography (silica: 100-200 mesh, MeOH:DCM 1%) to afford the title compound (6.5 g, 69%) as a solid. LCMS (ES+) 350.95 (M+H)+, RT 1.89 minutes (method 1).

Intermediate 6

7-[(2S)-2-Methylpiperazin-1-yl]thiazolo[5,4-d]pyrimidin-5-amine hydrochloride

To a solution of Intermediate 5 (2 g, 5.7 mmol) in 1,4-dioxane (5 mL) was added 4N HCl in 1,4-dioxane (20 mL) and the reaction mixture was stirred at room temperature for 12 h. The reaction mixture was then concentrated, and the crude material obtained was triturated with diethyl ether, to afford the title compound (1.2 g, 85%). LCMS (ES+) 250.95 (M+H)+, RT 0.53 minutes (method 1).

Intermediate 7 tert-Butyl (3S)-4-(5-aminothiazolo[5,4-d]pyrimidin-7-yl)-3-ethylpiperazine-1-carboxylate Intermediate 4 (2.33 mmol) and tert-butyl (3S)-3-ethylpiperazine-1-carboxylate (0.5 g, 2.33 mmol) in DMF (10 mL) were heated at 80° C. with DIPEA (3.5 mmol) for 6 h. After cooling, the reaction mixture was stirred at room temperature for 2 days, then concentrated in vacuo. The residue was partitioned between EtOAc and brine, then the organic layers were dried over sodium sulfate and concentrated in vacuo. The resulting crude material was purified by column chromatography (silica gel: 100-200 mesh, 100% EtOAc) to give the title compound (200 mg, 23.5%) as a white foam. LCMS (ES+) 365 (M+H)+, RT 1.02 minutes (method 3).

Intermediate 8

7-[(2S)-2-Isopropylpiperazin-1-yl]thiazolo[5,4-d]pyrimidin-5-amine hydrochloride Intermediate 4 (2.2 mmol) and tert-butyl (3S)-3-isopropylpiperazine-1-carboxylate (0.5 g, 2.2 mmol) in DMF (10 mL) and DIPEA (0.34 g, 2.63 mmol) were heated at 110° C. for 6 h. The reaction mixture was allowed to cool, then stirred overnight at room temperature. The reaction mixture was concentrated in vacuo, then partitioned between EtOAc and water. The organic layers were dried over sodium sulfate and concentrated in vacuo, then the crude material was purified by column chromatography (silica gel: 100-200 mesh, isohexanes:EtOAc, gradient 50% to 100% EtOAc) to give an off-white foam. This was taken up in 4N HCl in 1,4-dioxane (5 mL) and methanol (1 mL), and stirred for 1 h. The reaction mixture was concentrated in vacuo and triturated with diethyl ether to give the title compound (0.08 g, 12%). LCMS (ES+) 279 (M+H)+, RT 0.91 minutes (method 3).

Intermediate 9 tert-Butyl (3S)-4-(5-aminothiazolo[5,4-d]pyrimidin-7-yl)-3-cyclopropylpiperazine-1-carboxylate Intermediate 4 (2 mmol), tert-butyl (3S)-3-cyclopropylpiperazine-1-carboxylate (0.5 g, 2 mmol) and DIPEA (4 mmol) in DMF (10 mL) were heated at 90° C. for 6 h. The reaction mixture was cooled and stirred at room temperature for 2 days, then reheated at 90° C. for a further 6 h. The reaction was allowed to cool again, stirred at room temperature for 3 days, then concentrated in vacuo and partitioned between EtOAc and water. The organic layers were dried over sodium sulphate, concentrated in vacuo onto silica, then purified by column chromatography (silica gel: 100-200 mesh, isohexanes: EtOAc, gradient 50% to 100% EtOAc), to give the title compound (0.18 g, 30%) as a gum. LCMS (ES+) 377 (M+H)+, RT 1.074 minutes (method 3).

Intermediate 10 tert-Butyl (3S)-4-(5-aminothiazolo[5,4-d]pyrimidin-7-yl)-3-isobutylpiperazine-1-carboxylate Intermediate 4 (2.06 mmol) and tert-butyl (3S)-3-isobutylpiperazine-1-carboxylate (0.5 g, 2.06 mmol) in DMF (10 mL) and DIPEA (3.09 mmol) were heated at 90° C. for 8 h, then allowed to cool. The reaction mixture was partitioned between EtOAc and brine. The organic layers were dried over sodium sulfate and concentrated onto silica, then purified by column chromatography (silica gel: 100-200 mesh, isohexanes:EtOAc, gradient 50% to 100% EtOAc), to give the title compound (0.24 g, 29.6%) as a pale yellow foam. LCMS (ES+) 393 (M+H)+, RT 1.16 minutes (method 3).

Intermediate 11

2-[1-(5-Aminothiazolo[5,4-d]pyrimidin-7-yl)piperazin-2-yl]ethanol trifluoracetate salt To a solution of Intermediate 4 (0.38 g, 2.06 mmol) in DMF (20 mL) were added tert-butyl 3-(2-hydroxyethyl)piperazine-1-carboxylate (1 g, 4.12 mmol) and DIPEA (0.4 g, 3.0 mmol). The reaction mixture was heated at 100° C. for 5 h, allowed to cool, then stirred at room temperature for 2 days. The reaction mixture was concentrated in vacuo, then partitioned between water and DCM. The organic phase was separated and concentrated in vacuo. The resulting crude material was purified by column chromatography (silica gel: 100-200 mesh, MeOH:DCM gradient 0% to 20%) to give a pale yellow foam. The foam was dissolved in DCM (1 mL) and TFA (2 mL) and stirred for 1 h. The reaction mixture was concentrated in vacuo, then triturated with diethyl ether, to give the title compound (0.6 g) as a sticky yellow solid. LCMS (ES+) 281 (M+H)+, RT 0.361 minutes (method 3).

Intermediate 12 tert-Butyl 6,9-diazaspiro[3.5]nonane-6-carboxylate

Di-tert-butyl dicarbonate (1.0 g, 4.54 mmol) was added to a mixture of 6,9-diazaspiro[3.5]nonane dihydrochloride (1.0 g, 5.0 mmol) and DIPEA (2.2 mL, 13.0 mmol) in DCM (20 mL), and the reaction mixture was stirred for 20 h. The reaction mixture was concentrated in vacuo, and the residue was purified by column chromatography on silica gel, with a gradient of 2% increasing to 10% [10% (25% NH4OH in water) in MeOH] in DCM over 20 column volumes, to give a mixture of the title compound and DIPEA (2.50 g) as an orange oil. The resulting material was utilised without further purification. LCMS (ES+) 171.0 (M+H)+, RT 1.69 minutes (method 3).

Intermediate 13 tert-Butyl 9-(2-amino-6-chloro-5-formamidopyrimidin-4-yl)-6,9-diazaspiro[3.5]-nonane-6-carboxylate A mixture of Intermediate 12 (1.13 g, 5.02 mmol) and N-(2-amino-4,6-dichloropyrimidin-5-yl)formamide (1.04 g, 5.02 mmol) in 1,4-dioxane (40 mL) was treated with DIPEA (1.30 mL, 7.53 mmol) and heated at 100° C. for 7 days, then cooled to room temperature and concentrated in vacuo. The residue was dissolved in DCM (20 mL), washed with water (20 mL) and brine (20 mL), then dried over MgSO4 and concentrated in vacuo. The residue was purified by column chromatography on silica gel, with a gradient of 20% increasing to 70% EtOAc in isohexane over 20 column volumes, to give the title compound (0.44 g, 22%) as an off-white solid. LCMS (ES+) 397.2 (M+H)+, RT 1.24 minutes (method 3).

Intermediate 14 tert-Butyl 9-(5-aminothiazolo[5,4-d]pyrimidin-7-yl)-6,9-diazaspiro[3.5]nonane-6-carboxylate Intermediate 13 (0.44 g, 1.11 mmol) was dissolved in THF (20 mL) and treated with Lawesson's reagent. The reaction mixture was heated to 70° C. and stirred for 3 h, then cooled to room temperature and concentrated in vacuo. The residue was dissolved in DCM (20 mL) and washed with brine (2×20 mL), then passed through a phase separator cartridge and evaporated. The residue was purified by column chromatography on silica gel, with a gradient of 20% increasing to 70% EtOAc in isohexane over 20 column volumes, to give the title compound (0.44 g, >99%) as a yellow oil. LCMS (ES+) 377.4 (M+H)+, RT 1.44 minutes (method 3).

Intermediate 15

7-(6,9-Diazaspiro[3.5]nonan-9-yl)thiazolo[5,4-d]pyrimidin-5-amine hydrochloride

Intermediate 14 (0.41 g, 1.11 mmol) was dissolved/suspended in 4M HCl in 1,4-dioxane (10 mL) and stirred for 2 h, then concentrated in vacuo. The title compound (0.47 g, >99%) was obtained as a cream-coloured powder, and this material was utilised without purification. LCMS (ES+) 277.4 (M+H)+, RT 1.01 minutes (method 3).

Intermediate 16 tert-Butyl (3R,5S)-4-(2-amino-6-chloro-5-formamidopyrimidin-4-yl)-3,5-dimethylpiperazine-1-carboxylate Prepared from tert-butyl (3R,5S)-3,5-dimethylpiperazine-1-carboxylate (1.10 g, 5.13 mmol) following the method used to prepare Intermediate 13. LCMS (ES+) 385.8 (M+H)+, RT 1.64 minutes (method 3).

Intermediate 17 tert-Butyl (3R,5S)-4-(5-aminothiazolo[5,4-d]pyrimidin-7-yl)-3,5-dimethylpiperazine-1-carboxylate Prepared from Intermediate 16 following the method used to prepare Intermediate 14. LCMS (ES+) 365.8 (M+H)+, RT 2.24 minutes (method 3).

Intermediate 18

7-[(2R,6S)-2,6-Dimethylpiperazin-1-yl]thiazolo[5,4-d]pyrimidin-5-amine hydrochloride Prepared from Intermediate 17 following the method used to prepare Intermediate 15. LCMS (ES+) 265.2 (M+H)+, RT 0.53 minutes (method 3).

Intermediate 19

7-[(2R)-2-Methylpiperazin-1-yl]thiazolo[5,4-d]pyrimidin-5-amine trifluoroacetate salt To a solution of Intermediate 4 (0.5 g, 2.68 mmol) in 1,4-dioxane (10 mL) were added tert-butyl (3R)-3-methylpiperazine-1-carboxylate (2.14 mmol) and DIPEA (0.86 mL). The reaction mixture was heated at 100° C. for 8 h, after which time the reaction was filtered hot and the solid discarded. The filtrate was concentrated in vacuo, and partitioned between DCM and water. The organic layers were dried and further concentrated in vacuo. The residue was purified by column chromatography on silica gel, with a gradient of 20% increasing to 100% EtOAc in isohexane, to yield a foam. The material was taken up in DCM (2 mL) and TFA (2 mL), then stirred at room temperature overnight. The reaction mixture was concentrated in vacuo, then triturated with diethyl ether, to yield the title compound (470 mg, 52%). LCMS (ES+) 251.2 (M+H)$^+$, RT 0.58 minutes (method 3).

Intermediate 20

3-(Cyclopropylamino)-4-ethoxycyclobut-3-ene-1,2-dione

To a solution of 3,4-diethoxycyclobut-3-ene-1,2-dione (0.596 g, 3.5 mmol) in EtOH (5 mL) was added cyclopropylamine (0.2 g, 3.5 mmol), followed by triethylamine (0.49 mL, 3.5 mmol). The reaction mixture was stirred at room temperature for 30 minutes. The title compound (0.13 g, 20%) formed as a white precipitate that was collected by filtration and washed with diethyl ether. LCMS (ES+) 182 (M+H)$^+$, RT 1.42 minutes (method 1).

Intermediate 21

3-Anilino-4-ethoxycyclobut-3-ene-1,2-dione

Prepared from aniline following the method used to prepare Intermediate 20. LCMS (ES+) 218 (M+H)$^+$, RT 2.01 minutes (method 1).

Intermediate 22

5-Methoxypyrazin-2-amine

To a solution of 5-chloropyrazin-2-amine (0.2 g, 1.54 mmol) in MeOH (3 mL) was added Cu powder (0.13 g, 2.07 mmol), followed by a solution of sodium methoxide in MeOH (0.38 mL, 1.75 mmol). The reaction mixture was stirred at 150° C. in a sealed tube for 24 h. The reaction mixture was then filtered through Celite, and the filtrate was concentrated in vacuo. The crude product obtained was purified by column chromatography (silica: 100-200 mesh, MeOH:DCM 2-3%) to afford the title compound (0.13 g, 67%). LCMS (ES+) 126 (M+H)$^+$, RT 1.06 minutes (method 1).

Intermediate 23

5-Methoxy-3-methylpyrazin-2-amine

Prepared from 5-chloro-3-methylpyrazin-2-amine following the method used to prepare Intermediate 22. LCMS (ES+) 140 (M+H)$^+$, RT 1.25 minutes (method 1).

Intermediate 24

2-Methoxy-4-methylpyrimidin-5-amine

Prepared from 2-chloro-4-methylpyrimidin-5-amine following the method used to prepare Intermediate 22. LCMS (ES+) 140 (M+H)$^+$, RT 1.25 minutes (method 1).

Intermediate 25

2-Methoxypyrimidin-5-amine

Prepared from 2-chloropyrimidin-5-amine following the method used to prepare Intermediate 22. LCMS (ES+) 125.95 (M+H)$^+$, RT 0.748 minutes (method 1).

Intermediate 26

6-Methoxypyridazin-3-amine

Prepared from 6-chloropyridazin-3-amine following the method used to prepare Intermediate 22. LCMS (ES+) 126 (M+H)$^+$, RT 0.735 minutes (method 1).

Intermediate 27

(3-Methyl-4-nitrophenyl)(pyrrolidin-1-yl)methanone

To a solution of 3-methyl-4-nitrobenzoic acid (0.5 g, 2.76 mmol) in DMF (4 mL) was added DIPEA (0.9 mL, 5.79 mmol), followed by HOBT (0.39 g, 2.89 mmol), EDC (0.44 g, 2.89 mmol) and pyrrolidine (0.196 g, 2.76 mmol). The reaction mixture was stirred at room temperature for 12 h. The reaction mixture was then diluted with water and extracted with EtOAc. The organic layer was washed with brine, then concentrated to provide crude material which was further purified by column chromatography (silica:100-200 mesh, MeOH:DCM 8-10%), to afford the title compound (0.31 g, 48.1%). LCMS (ES+) 235.05 (M+H)$^+$, RT 2.04 minutes (method 1).

Intermediate 28

(3-Methyl-4-nitrophenyl)(4-methylpiperazin-1-yl)methanone

Prepared from 3-methyl-4-nitrobenzoic acid and 1-methylpiperazine following the method used to prepare Intermediate 27. $\delta_H$ (DMSO-d$_6$) 8.03 (d, J=8.3 Hz, 1H), 7.52 (d, J=1.9 Hz, 1H), 7.44 (dd, J8.4, 1.9 Hz, 1H), 3.66 (m, 2H), 3.26 (s, 2H), 2.53 (s, 3H), 2.37 (s, 2H), 2.25 (s, 2H), 2.19 (s, 3H).

Intermediate 29

N,N,3-Trimethyl-4-nitrobenzamide

To a solution of 3-methyl-4-nitrobenzoic acid (0.5 g, 2.76 mmol) in DMF (5 mL) was added DIPEA (1.06 g, 8.28 mmol), followed by HATU (1.57 g, 4.14 mmol) and dimethylamine (0.24 g, 5.52 mmol). The reaction mixture was stirred at room temperature for 12 h. The reaction mixture was then diluted with water and extracted with EtOAc. The organic layer was washed with brine, then concentrated to provide crude material which was further purified by column chromatography (silica:100-200 mesh, MeOH:DCM 8-10%), to afford the title compound (0.42 g, 73.17%). LCMS (ES+) 209 (M+H)$^+$, RT 1.92 minutes (method 3).

Intermediate 30

(3-Methyl-4-nitrophenyl)(morpholin-4-yl)methanone

Prepared from 3-methyl-4-nitrobenzoic acid and morpholine following the method used to prepare Intermediate 29. $\delta_H$ (DMSO-d$_6$) 8.03 (d, J=8.3 Hz, 1H), 7.60-7.52 (m, 1H), 7.47 (dd, J8.4, 1.9 Hz, 1H), 3.50-3.70 (m, 6H), 3.28 (m, 2H), 2.53 (s, 3H).

Intermediate 31

1-[(3-Methyl-4-nitrophenyl)methyl]pyrrolidine

To a solution of Intermediate 27 (0.3 g, 1.28 mmol) in THF (10 mL) was added borane dimethyl sulphide complex (2M solution in THF, 3.8 mL) at room temperature. The reaction mixture was heated at reflux for 15 minutes. To the reaction mixture was added 6M HCl dropwise and the reaction mixture was heated under reflux for a further 2 h. The reaction mixture was then cooled to room temperature and 4N NaOH solution was added. The reaction mixture was extracted with EtOAc and the organic layer was concentrated, to provide crude material which was further purified by column chromatography (silica:100-200 mesh, MeOH:DCM 5-7%), to afford the title compound (0.25 g, 88.6%). LCMS (ES+) 221 (M+H)$^+$, RT 2.83 minutes (method 1).

Intermediate 32

1-Methyl-4-[(3-methyl-4-nitrophenyl)methyl]piperazine

Prepared from Intermediate 28 following the method used to prepare Intermediate 31. LCMS (ES+) 250.05 (M+H)$^+$, RT 2.34 minutes (method 1).

Intermediate 33

N,N-Dimethyl-1-(3-methyl-4-nitrophenyl)methanamine

Prepared from Intermediate 29 following the method used to prepare Intermediate 31. LCMS (ES+) 195 (M+H)$^+$, RT 2.75 minutes (method 1).

Intermediate 34

4-[(3-Methyl-4-nitrophenyl)methyl]morpholine

Prepared from Intermediate 30 following the method used to prepare Intermediate 31. LCMS (ES+) 237 (M+H)$^+$, RT 2.39 minutes (method 1).

Intermediate 35

2-Methyl-4-(pyrrolidin-1-ylmethyl)aniline

To a solution of Intermediate 31 (0.25 g, 1.13 mmol) in MeOH (5 mL) was added Pd/C (0.04 g). The reaction mixture was stirred under a hydrogen atmosphere for 4 h at room temperature. The reaction mixture was then filtered through Celite and the organic layer was concentrated, to provide the title compound (0.2 g, 93.0%). LCMS (ES+) 191 (M+H)$^+$, RT 2.09 minutes (method 1).

Intermediate 36

2-Methyl-4-[(4-methylpiperazin-1-yl)methyl]aniline

Prepared from Intermediate 32 following the method used to prepare Intermediate 35. LCMS (ES+) 220.05 (M+H)$^+$, RT 1.21 minutes (method 1).

Intermediate 37

4-(Dimethylaminomethyl)-2-methylaniline

Prepared from Intermediate 33 following the method used to prepare Intermediate 35. LCMS (ES+) 165.10 (M+H)$^+$, RT 2.15 minutes (method 1).

Intermediate 38

2-Methyl-4-(morpholin-4-ylmethyl)aniline

Prepared from Intermediate 34 following the method used to prepare Intermediate 35. LCMS (ES+) 207.05 (M+H)$^+$, RT 1.23 minutes (method 1).

Intermediate 39

6-Methyl-5-nitropyridine-2-carbaldehyde

A solution of 2,6-dimethyl-3-nitropyridine (1.5 g, 9.85 mmol) and SeO$_2$ (1.4 g, 12.81 mmol) in 1,4-dioxane (15 mL) was heated at reflux for 16 h. The reaction mixture was then filtered through Celite and the solvent was evaporated. The crude material obtained was purified by column chromatography (silica: 100-200 mesh, EtOAc:hexane 20-25%) to afford the title compound (0.61 g, 37.4%). δ$_H$ (CDCl$_3$) 10.09 (s, 1H), 8.39 (d, J=8.3 Hz, 1H), 7.97 (d, J=8.3 Hz, 1H), 2.94 (s, 3H).

Intermediate 40

2-Methyl-3-nitro-6-(pyrrolidin-1-ylmethyl)pyridine

To a solution of Intermediate 39 (0.35 g, 2.1 mmol) in 1,2-dichloroethane (5 mL) were added pyrrolidine (0.2 g, 3.1 mmol) and a catalytic amount of glacial acetic acid. The reaction mixture was stirred for 30 minutes at room temperature. The reaction mixture was then cooled to 0° C., sodium cyanoborohydride (0.15 g, 2.5 mmol) was added, and the reaction mixture was stirred for a further 1 h. The reaction mixture was then quenched with water and the aqueous layer was extracted with DCM. The organic layer was concentrated and the crude material obtained was purified by column chromatography (silica: 100-200 mesh, MeOH:DCM 4-5%), to afford the title compound (0.16 g, 34.4%). LCMS (ES+) 222.05 (M+H)$^+$, RT 2.33 minutes (method 1).

Intermediate 41

1-Methyl-4-[(6-methyl-5-nitropyridin-2-yl)methyl]piperazine

Prepared from Intermediate 39 and 1-methylpiperazine following the method used to prepare Intermediate 40. LCMS (ES+) 251.10 (M+H)$^+$, RT 1.69 minutes (method 1).

Intermediate 42

4-[(6-Methyl-5-nitropyridin-2-yl)methyl]morpholine

Prepared from Intermediate 39 and morpholine following the method used to prepare Intermediate 40. LCMS (ES+) 238.05 (M+H)$^+$, RT 1.79 minutes (method 1).

Intermediate 43

2-Methyl-6-(pyrrolidin-1-ylmethyl)pyridin-3-amine

To a solution of Intermediate 40 (0.15 g, 0.67 mmol) in MeOH (5 mL) was added Pd/C (0.02 g). The reaction mixture was stirred under a hydrogen atmosphere for 6 h at room temperature. The reaction mixture was filtered through Celite and the organic layer was concentrated to obtain the title compound (0.1 g, 77.5%). LCMS (ES+) 192.1 (M+H)$^+$, RT 1.24 minutes (method 1).

Intermediate 44

2-Methyl-6-[(4-methylpiperazin-1-yl)methyl]pyridin-3-amine

Prepared from Intermediate 41 following the method used to prepare Intermediate 43. LCMS (ES+) 221.1 (M+H)$^+$, RT 0.78 minutes (method 1).

Intermediate 45

2-Methyl-6-(morpholin-4-ylmethyl)pyridin-3-amine

Prepared from Intermediate 42 following the method used to prepare Intermediate 43. LCMS (ES+) 208.05 (M+H)$^+$, RT 0.66 minutes (method 1).

Intermediate 46

N,N,6-Trimethyl-5-nitropyridin-2-amine

To a solution of 6-chloro-2-methyl-3-nitropyridine (0.5 g, 2.9 mmol) in MeOH (5 mL) was added dimethylamine in water (1.2 mL, 11.6 mmol) and the reaction mixture was heated at 60° C. for 4 h. The reaction mixture was then diluted with EtOAc, extracted with water and washed with brine. The organic layer was dried over sodium sulphate and concentrated to yield the title compound (0.5 g, 95%). LCMS (ES+) 182 (M+H)$^+$, RT 2.74 minutes (method 1).

Intermediate 47

6-(Azetidin-1-yl)-2-methyl-3-nitropyridine

Prepared from 6-chloro-2-methyl-3-nitropyridine and azetidine following the method used to prepare Intermediate 46. LCMS (ES+) 194 (M+H)$^+$, RT 2.55 minutes (method 1).

Intermediate 48

2-Methyl-3-nitro-6-(pyrrolidin-1-yl)pyridine

To a solution of 6-chloro-2-methyl-3-nitropyridine (0.5 g, 2.9 mmol) in pyrrolidine (0.7 mL, 8.7 mmol) was added K$_2$CO$_3$ (0.8 g, 5.8 mmol). The reaction mixture was heated at 110° C. for 2 h. Water (2 mL) was then added and the title compound (0.6 g, 99%) was collected by filtration. LCMS (ES+) 208 (M+H)$^+$, RT 3.019 minutes (method 1).

Intermediate 49

6-(3-Fluoroazetidin-1-yl)-2-methyl-3-nitropyridine

To a solution of 6-chloro-2-methyl-3-nitropyridine (0.5 g, 2.9 mmol) in DMF (5 mL) was added Cs$_2$CO$_3$ (1.9 g, 5.8 mmol) followed 3-fluoroazetidine (0.64 g, 5.8 mmol) and the reaction mixture was heated for 2 h at 80° C. The reaction mixture was then diluted with EtOAc and the organic layer was washed with saturated aqueous sodium bicarbonate solution. The organic layer was then dried over sodium sulphate and concentrated. The crude material obtained was purified by column chromatography (silica: 100-200 mesh, MeOH:DCM 2-3%) to afford the title compound (0.6 g, 92%). LCMS (ES+) 211.95 (M+H)$^+$, RT 2.33 minutes (method 1).

Intermediate 50

6-(3,3-Difluoroazetidin-1-yl)-2-methyl-3-nitropyridine

Prepared from 6-chloro-2-methyl-3-nitropyridine and 3,3-difluoroazetidine following the method used to prepare Intermediate 49. LCMS (ES+) 230 (M+H)$^+$, RT 2.57 minutes (method 1).

Intermediate 51

6-(3,3-Difluoropyrrolidin-1-yl)-2-methyl-3-nitropyridine

To a solution of 6-chloro-2-methyl-3-nitropyridine (0.3 g, 1.74 mmol) in DMF (2 mL) was added K$_2$CO$_3$ (0.72 g, 5.23 mmol) followed by 3,3-difluoropyrrolidine hydrochloride (0.74 g, 5.23 mmol) and the reaction mixture was heated for 4 h at 80° C. The reaction mixture was then diluted with ethyl acetate and the organic layer was washed with saturated aqueous sodium bicarbonate solution. The organic layer was then dried over sodium sulphate and concentrated. The crude material obtained was purified by column chromatography (silica: 100-200 mesh, MeOH:DCM 2-3%) to afford the title compound (0.2 g, 47%). LCMS (ES+) 244.05 (M+H)$^+$, RT 3.028 minutes (method 1).

Intermediate 52

6-(3,3-Difluoropiperidin-1-yl)-2-methyl-3-nitropyridine

Prepared from 6-chloro-2-methyl-3-nitropyridine and 3,3-difluoropiperidine following the method used to prepare Intermediate 51. LCMS (ES+) 258.05 (M+H)$^+$, RT 3.069 minutes (method 1).

Intermediate 53

6-(3-Fluoropyrrolidin-1-yl)-2-methyl-3-nitropyridine

The title compound was prepared from 6-chloro-2-methyl-3-nitropyridine and 3-fluoropyrrolidine following the method used to prepare Intermediate 51. LCMS (ES+) 226 (M+H)$^+$, RT 2.847 minutes (method 1).

Intermediate 54

3-Fluoro-1-(3-methyl-4-nitrophenyl)pyrrolidine

Prepared from 4-chloro-2-methyl-1-nitrobenzene and 3-fluoropyrrolidine following the method used to prepare Intermediate 49. LCMS (ES+) 224.90 (M+H)$^+$, RT 2.90 minutes (method 1).

Intermediate 55

N²,N²,6-Trimethylpyridine-2,5-diamine

To a stirred solution of Intermediate 46 (0.5 g, 2.8 mmol) in MeOH (10 mL) was added Pd/C (0.05 g) and reaction mixture was stirred under a hydrogen atmosphere for 4 h. The reaction mixture was then filtered through Celite and concentrated to yield the title compound (0.38 g, 91%). LCMS (ES+) 152 (M+H)⁺, RT 1.338 minutes (method 1).

Intermediate 56

6-(Azetidin-1-yl)-2-methylpyridin-3-amine

Prepared from Intermediate 47 following the method used to prepare Intermediate 55. LCMS (ES+) 164 (M+H)⁺, RT 1.026 minutes (method 1).

Intermediate 57

2-Methyl-6-(pyrrolidin-1-yl)pyridin-3-amine

Prepared from Intermediate 48 following the method used to prepare Intermediate 55. LCMS (ES+) 178 (M+H)⁺, RT 1.7 minutes (method 1).

Intermediate 58

6-(3-Fluoroazetidin-1-yl)-2-methylpyridin-3-amine

Prepared from Intermediate 49 following the method used to prepare Intermediate 55. LCMS (ES+) 182.05 (M+H)⁺, RT 1.09 minutes (method 1).

Intermediate 59

6-(3,3-Difluoroazetidin-1-yl)-2-methylpyridin-3-amine

Prepared from Intermediate 50 following the method used to prepare Intermediate 55. LCMS (ES+) 200 (M+H)⁺, RT 1.55 minutes (method 1).

Intermediate 60

6-(3,3-Difluoropyrrolidin-1-yl)-2-methylpyridin-3-amine

Prepared from Intermediate 51 following the method used to prepare Intermediate 55. LCMS (ES+) 214 (M+H)⁺, RT 2.07 minutes (method 1).

Intermediate 61

6-(3,3-Difluoropiperidin-1-yl)-2-methylpyridin-3-amine

Prepared from Intermediate 52 following the method used to prepare Intermediate 55. LCMS (ES+) 228.05 (M+H)⁺, RT 2.19 minutes (method 1).

Intermediate 62

6-(3-Fluoropyrrolidin-1-yl)-2-methylpyridin-3-amine

Prepared from Intermediate 53 following the method used to prepare Intermediate 55. LCMS (ES+) 196 (M+H)⁺, RT 1.799 minutes (method 1).

Intermediate 63

4-(3-Fluoropyrrolidin-1-yl)-2-methylaniline

Prepared from Intermediate 54 following the method used to prepare Intermediate 55. LCMS (ES+) 195.05 (M+H)⁺, RT 2.28 minutes (method 1).

Intermediate 64

6-(Difluoromethoxy)-2-methyl-3-nitropyridine

To a solution of 6-methyl-5-nitropyridin-2-ol (0.5 g, 3.2 mmol) in acetonitrile (10 mL) was added NaH (0.35 g, 8.64 mmol) and the reaction mixture was stirred for 15 minutes at room temperature. To the reaction mixture was added 2,2-difluoro-2-(fluoro-sulfonyl)acetic acid (1.1 mL, 5.5 mmol) dropwise. The reaction mixture was stirred for a further 15 minutes. The reaction mixture was then quenched by the addition of water, and diluted with EtOAc. The organic layer was washed with water and brine, dried over sodium sulphate and concentrated. The crude material obtained was purified by column chromatography (silica: 100-200 mesh, MeOH: DCM 2-4%) to afford the title compound (0.5 g, 75%) as a white solid. LCMS (ES−) 202.85 (M−H)⁻, RT 2.75 minutes (method 1).

Intermediate 65

6-(Difluoromethoxy)-2-methylpyridin-3-amine

Prepared from Intermediate 64 following the method used to prepare Intermediate 55. $\delta_H$ (CDCl₃) 7.32-7.18 (t, J=74.2 Hz, 1H), 7.00 (d, J=8.4 Hz, 1H), 6.61 (d, J=8.4 Hz, 1H), 3.45 (br s, 2H), 2.32 (s, 3H).

Intermediate 66

Tetrahydrofuran-3-yl methanesulfonate

To a solution of 3-tetrahydrofuranol (1 g, 6.5 mmol) in DCM (10 mL) was added triethylamine (1.9 mL, 13.6 mmol). The reaction mixture was stirred for 15 minutes at room temperature. To the reaction mixture was added methanesulfonyl chloride (1.08 mL, 13.6 mmol) at 0° C. The reaction mixture was stirred for a further 18 h. The reaction mixture was then quenched by addition of water, and diluted with EtOAc. The organic layer was washed with water and brine, dried over sodium sulphate and concentrated to yield the title compound (1.9 g, 88%). $\delta_H$ (CDCl₃) 5.32 (m, 1H), 4.10-3.80 (m, 4H), 3.70 (s, 3H), 2.30-2.20 (m, 2H).

Intermediate 67

2-Methyl-3-nitro-6-(tetrahydrofuran-3-yloxy)pyridine

To a solution of 6-methyl-5-nitropyridin-2-ol (1 g, 6.5 mmol) in DMA (5 mL) was added Cs₂CO₃ (4 g, 13.1 mmol)

and the reaction mixture was stirred for 10 minutes. To the reaction mixture was added Intermediate 66 (1.2 g, 7.2 mmol) and the reaction mixture was heated at 90° C. for a further 18 h. The reaction mixture was then filtered through Celite using ethyl acetate. The organic layer was washed with water and brine, dried over sodium sulphate and concentrated. The crude material obtained was purified by column chromatography (silica: 100-200 mesh, MeOH:DCM 2-4%) to afford the title compound (1.2 g, 82%) as a yellow solid. $\delta_H$ (CDCl$_3$) 5.32 (m, 1H), 4.10-3.80 (m, 4H), 3.70 (s, 3H), 2.30-2.20 (m, 2H).

Intermediate 68

2-Methyl-6-(tetrahydrofuran-3-yloxy)pyridin-3-amine

Prepared from Intermediate 67 following the method used to prepare Intermediate 55. LCMS (ES+) 194.10 (M+H)$^+$, RT 1.24 minutes (method 1).

Intermediate 69

6-Methoxy-3-nitro-2-(trifluoromethyl)pyridine

To a solution of 2-chloro-6-methoxy-3-nitropyridine (0.6 g, 3.2 mmol) in DMF (1.2 mL) were added CuI (0.73 g, 3.8 mmol) and KF (0.37 g, 6.4 mmol), followed by methyl chlorodifluoroacetate (1.15 g, 7.97 mmol). The reaction mixture was heated for 13 h at 120° C. The reaction mixture was then cooled to room temperature and poured onto a mixture of NH$_4$OH and saturated aqueous NH$_4$Cl solution (1:1). The resulting solution was stirred for 1.5 h at room temperature. The organic layer was washed with water and brine, dried over sodium sulphate and concentrated. The crude material obtained was purified by column chromatography (silica: 100-200 mesh, DCM:hexane 3-4%) to afford the title compound (0.5 g, 71%) as a colourless oil. $\delta_H$ (CDCl$_3$) 8.17 (d, J=8.9 Hz, 1H), 7.03 (d, J=8.9 Hz, 1H), 4.09 (s, 3H).

Intermediate 70

6-Methyl-3-nitro-2-(trifluoromethyl)pyridine

Prepared from 2-chloro-6-methyl-3-nitropyridine following the method used to prepare Intermediate 69. $\delta_H$ (CDCl$_3$) 8.11 (d, J=8.3 Hz, 1H), 7.53 (d, J=8.3 Hz, 1H), 2.74 (s, 3H).

Intermediate 71

6-Methoxy-2-(trifluoromethyl)pyridin-3-amine

Prepared from Intermediate 69 following the method used to prepare Intermediate 55. LCMS (ES+) 193 (M+H)$^+$, RT 2.37 minutes (method 1).

Intermediate 72

6-Methyl-2-(trifluoromethyl)pyridin-3-amine

Prepared from Intermediate 70 following the method used to prepare Intermediate 55. LCMS (ES+) 177 (M+H)$^+$, RT 1.47 minutes (method 1).

Intermediate 73

N,N,6-Trimethyl-3-nitropyridin-2-amine

Prepared from 2-chloro-6-methyl-3-nitropyridine following the method used to prepare Intermediate 46. LCMS (ES+) 182 (M+H)$^+$, RT 2.83 minutes (method 1).

Intermediate 74

N$^2$,N$^2$,6-Trimethylpyridin-2,3-diamine

Prepared from Intermediate 73 following the method used to prepare Intermediate 55. LCMS (ES+) 152 (M+H)$^+$, RT 1.63 minutes (method 1).

Intermediate 75 tert-Butyl 4-(5-aminothiazolo[5,4-d]pyrimidin-7-yl)-3-(2-methoxy-2-oxoethyl)-piperazine-1-carboxylate DIPEA (1.35 mL, 7.78 mmol) was added to a solution of Intermediate 4 (0.97 g, 5.18 mmol) and 4-(tert-butoxycarbonyl)piperazin-2-ylacetic acid methyl ester (1.34 g, 5.18 mmol) in 1,4-dioxane (40 mL). The reaction mixture was heated at 100° C. for 4 days, then cooled to room temperature and concentrated in vacuo. The residue was partitioned between DCM (20 mL) and water (20 mL), then separated. The organic phase was washed with brine (20 mL), then dried over MgSO$_4$ and evaporated. The residue was purified by column chromatography on silica gel, with a gradient of 20% increasing to 70% EtOAc in isohexane over 20 column volumes, to give the title compound (0.91 g, 43%) as a yellow oil. LCMS (ES+) 409.4 (M+H)$^+$, RT 0.32 minutes (method 3).

Intermediate 76

2-[1-(5-Aminothiazolo[5,4-d]pyrimidin-7-yl)piperazin-2-yl]acetic acid hydrochloride and Methyl 2-[1-(5-aminothiazolo[5,4-d]pyrimidin-7-yl)piperazin-2-yl]acetate hydrochloride Intermediate 75 (0.91 g, 2.23 mmol) was dissolved/suspended in 4M HCl in 1,4-dioxane (20 mL) and stirred for 6 h, then concentrated in vacuo. A mixture of the two title compounds (0.81 g) was obtained as a brown foaming gum, which was utilised without further purification. LCMS (ES+) 295.2 (M+H)$^+$, RT 0.23 minutes; and 309.2 (M+H)$^+$, RT 0.90 minutes (method 3).

Intermediate 77 tert-Butyl (3S)-4-(5-aminothiazolo[5,4-d]pyrimidin-7-yl)-3-(hydroxymethyl)-piperazine-1-carboxylate Prepared from (S)-3-(hydroxymethyl)piperazine-1-carboxylic acid tert-butyl ester and Intermediate 4 following the method used to prepare Intermediate 75. LCMS (ES+) 367.8 (M+H)$^+$, RT 1.65 minutes (method 3).

Intermediate 78 tert-Butyl (3R)-4-(5-aminothiazolo[5,4-d]pyrimidin-7-yl)-3-(hydroxymethyl)-piperazine-1-carboxylate To a solution of Intermediate 4 (4.63 mmol) and (R)-3-(hydroxymethyl)-piperazine-1-carboxylic acid tert-butyl ester (1 g, 4.62 mmol) in DMF (20 mL) was added DIPEA (6.94 mmol). The reaction mixture was heated at 100° C. for 7 h, then cooled and stirred at room temperature for 2 days. The reaction mixture was concentrated in vacuo and partitioned between EtOAc and water. The organic layers were dried over sodium sulfate and concentrated again. The resulting orange oil was purified by column chromatography on silica gel, with a gradient of 1% increasing to 20% MeOH in DCM, to yield the title compound (0.42 g, 24.8%) as a yellow gummy solid. LCMS (ES+) 367.8 (M+H)$^+$, RT 0.8 minutes (method 3).

Intermediate 79

[(2S)-1-(5-Aminothiazolo[5,4-d]pyrimidin-7-yl)piperazin-2-yl]methanol hydrochloride Prepared from Intermediate 77 following the method used to prepare Intermediate 15. LCMS (ES+) 267.2 (M+H)$^+$, RT 0.34 minutes (method 3).

Intermediate 80

[(2R)-1-(5-Aminothiazolo[5,4-d]pyrimidin-7-yl)piperazin-2-yl]methanol hydrochloride Prepared from Intermediate 78 following the method used to prepare Intermediate 15. LCMS (ES+) 267.2 (M+H)$^+$, RT 0.35 minutes (method 3).

Intermediate 81 tert-Butyl (1S,5R)-3-[(4-methoxyphenyl)carbamoyl]-3,8-diazabicyclo[3.2.1]octane-8-carboxylate DIPEA (0.53 mL, 3.0 mmol) was added to a suspension of tert-butyl (1S,5R)-3,8-diazabicyclo[3.2.1]octane-8-carboxylate hydrochloride (0.50 g, 2.00 mmol) in DCM (20 mL). To the mixture was added 4-methoxyphenyl isocyanate (0.26 mL, 2.0 mmol) dropwise, and the reaction mixture was stirred for 20 h. The reaction mixture was washed with brine (2×20 mL), then passed through a phase separator and evaporated. The crude material was purified by flash chromatography on silica, with a gradient of 25% increasing to 75% EtOAc/isohexane over 20 column volumes. The title compound (0.74 g, >99%) was obtained as a white solid. LCMS (ES+) 362.8 (M+H)$^+$, RT 2.02 minutes (method 3).

Intermediate 82

(1S,5R)—N-(4-Methoxyphenyl)-3,8-diazabicyclo[3.2.1]octane-3-carboxamide hydrochloride Prepared from Intermediate 81 following the method used to prepare Intermediate 15. LCMS (ES+) 260.2 (M+H)$^+$, RT 0.47 minutes (method 3).

Intermediate 83

3-(3-Methyl-4-nitrophenoxy)oxetane

Sodium hydride (0.084 g, 2.11 mmol) was added to a solution of oxetan-3-ol (0.12 g, 1.62 mmol) in THF (10 mL) at 0° C. The mixture was stirred at 0° C. for 20 minutes, after which time a solution of 5-fluoro-2-nitrotoluene (0.26 g, 1.62 mmol) in THF (10 mL) was added. The mixture was allowed to warm to room temperature, and stirring was continued for 16 h. The reaction mixture was diluted with water and extracted with DCM. The organic layer was washed with brine. The organic layer was concentrated under vacuum and the resulting crude material was purified by column chromatography (silica gel: 100-200 mesh, 8-30% EtOAc/hexane) to give the title compound (0.18 g, 54%) as a yellow gum. LCMS (ES+) no mass ion observed, RT 1.71 minutes (method 2).

Intermediate 84

2-Methyl-4-(oxetan-3-yloxy)aniline

Intermediate 83 (0.18 g, 0.875 mmol) was dissolved in MeOH (30 mL). 10% Palladium on carbon (0.02 g, 0.188 mmol) was added and the mixture was stirred under an atmosphere of hydrogen for 16 h. The reaction mixture was filtered through a pad of Celite and the solvent was removed in vacuo, to give the title compound (0.14 g, 89%) as an off-white solid. LCMS (ES+) 180.8 (M+H)$^+$, RT 0.80 minutes (method 2).

Intermediate 85 tert-Butyl 4-(4-methyl-5-nitropyridin-2-yl)piperazine-1-carboxylate

2-Fluoro-4-methyl-5-nitropyridine (0.8 g, 5.12 mmol), tert-butyl piperazine-1-carboxylate (1.05 g, 5.64 mmol) and potassium carbonate (0.85 g, 6.15 mmol) were taken up in acetonitrile (15 mL) and heated at 60° C. for 1.5 h. After this time, the reaction was quenched with water (20 mL) and extracted with EtOAc (2×30 mL). The organic layers were combined and dried over sodium sulphate, then concentrated in vacuo. The crude material was purified by column chromatography (silica gel: 100-200 mesh, 1:1 EtOAc/heptane) to give the title compound (1.57 g, 97%). LCMS (ES+) 323.1 (M+H)$^+$, RT 1.71 minutes (method 4).

Intermediate 86

1-Methyl-4-(4-methyl-5-nitropyridin-2-yl)piperazine

Prepared from 1-methylpiperazine following the method used to prepare Intermediate 85. LCMS (ES+) 237.17 (M+H)$^+$, RT 1.30 minutes (method 4).

Intermediate 87 tert-Butyl 3-[(4-methyl-5-nitropyridin-2-yl)oxy]azetidine-1-carboxylate

Prepared from tert-butyl 3-hydroxyazetidine-1-carboxylate following the method used to prepare Intermediate 85. LCMS (ES+) 310.3 (M+H)$^+$, RT 1.67 minutes (method 4).

Intermediate 88 tert-Butyl 3-[(4-methyl-5-nitropyridin-2-yl)oxy]pyrrolidine-1-carboxylate

A suspension of sodium hydride (60% in oil, 11.54 mmol) in THF (2 mL) was added to tert-butyl 3-hydroxypyrrolidine-1-carboxylate (1.59 g, 8.46 mmol) in THF (15 mL) at 0° C. Once the bubbling had subsided, a solution of 2-fluoro-4-methyl-5-nitropyridine (1.2 g, 7.69 mmol) in THF (3 mL) was added over 5 minutes. After 1 h, more sodium hydride (60% in oil, 0.15 g) was added. After a further 1 h, the reaction was quenched with aqueous ammonium chloride solution and extracted with EtOAc (3×20 mL). The combined organic extracts were dried over sodium sulfate and concentrated to give a yellow solid. Purification by column chromatography (silica gel: 100-200 mesh, 1:4 EtOAc:heptane) yielded the title compound (1.62 g, 65%) as a yellow solid. LCMS (ES+) 323.3 (M+H)$^+$, RT 1.71 minutes (method 4).

Intermediate 89

4-Methyl-6-(4-methylpiperazin-1-yl)pyridin-3-amine

To a solution of Intermediate 86 (1.15 g, 4.87 mmol) in methanol (150 mL) was added Pd/C (0.17 g) as a slurry in toluene (0.2 mL). The mixture was stirred under an atmosphere of hydrogen until no starting material remained by TLC. After this time, the reaction mixture was filtered through Celite and concentrated. The crude material was purified by column chromatography (silica gel: 100-200 mesh, 15% MeOH in DCM) to give the title compound (0.58 g, 58%) as a red powder. LCMS (ES+) 207.14 (M+H)$^+$, RT 0.45 minutes (method 4).

Intermediate 90 tert-Butyl 4-(5-amino-4-methylpyridin-2-yl)piperazine-1-carboxylate

Prepared from Intermediate 85 following the method used to prepare Intermediate 89. LCMS (ES+) 293.15 (M+H)$^+$, RT 0.67 minutes (method 4).

Intermediate 91 tert-Butyl 3-[(5-amino-4-methylpyridin-2-yl)oxy]azetidine-1-carboxylate

Prepared from Intermediate 87 following the method used to prepare Intermediate 89. LCMS (ES+) 294.2 (M+H)$^+$, RT 1.38 minutes (method 4).

Intermediate 92 tert-Butyl 3-[(5-amino-4-methylpyridin-2-yl)oxy]pyrrolidine-1-carboxylate

Prepared from Intermediate 88 following the method used to prepare Intermediate 89. LCMS (ES+) 294.2 (M+H)$^+$, RT 1.38 minutes (method 4).

Intermediate 93 tert-Butyl (3R)-4-(5-aminothiazolo[5,4-d]pyrimidin-7-yl)-3-cyanopiperazine-1-carboxylate Intermediate 4 (0.45 g, 2.40 mmol) and tert-butyl (3R)-3-cyanopiperazine-1-carboxylate (0.51 g, 2.40 mmol) were taken up in chloroform (20 mL). p-Toluenesulfonic acid monohydrate (0.046 g, 0.24 mmol) was added and the mixture was stirred under nitrogen at 65° C. for 10 days. The reaction mixture was allowed to cool to room temperature, diluted with DCM and washed with water. The organic layer was washed with brine, and dried over sodium sulphate. The organic layer was concentrated under vacuum and the resulting crude material was purified by column chromatography (silica gel: 100-200 mesh, 40-100% EtOAc/isohexane) to give the title compound (0.165 g, 19%) as a colourless gum. LCMS (ES+) 362.8 (M+H)$^+$, RT 1.95 minutes (method 3).

Intermediate 94

(2R)-1-(5-Aminothiazolo[5,4-d]pyrimidin-7-yl)piperazine-2-carbonitrile hydrochloride Intermediate 93 (0.165 g, 0.457 mmol) was taken up in 4N HCl/1,4-dioxane (5 mL). The mixture was stirred at room temperature for 2 h. The solvent was removed in vacuo to give the title compound (0.15 g, quant.) as a yellow solid. LCMS (ES+) 262.2 (M+H)$^+$, RT 0.64 minutes (method 3).

Intermediate 95 tert-Butyl 5-(5-aminothiazolo[5,4-d]pyrimidin-7-yl)-2,5-diazabicyclo[2.2.1]heptane-2-carboxylate To a solution of Intermediate 4 (1 g, 5.37 mmol) in 1,4-dioxane (7 mL) was added DIPEA (1.32 mL, 8.046 mmol), followed by tert-butyl 2,5-diazabicyclo[2.2.1]heptane-2-carboxylate (1.17 g, 5.90 mmol). The reaction mixture was heated at 55° C. for 3 h. The reaction mixture was then concentrated, and diluted with DCM. The organic layer was washed with water and 5% aqueous acetic acid solution, then concentrated. The crude material obtained was purified by column chromatography (silica: 100-200 mesh, MeOH:DCM 2%) to afford the title compound (1 g, 55.5%). LCMS (ES+) 349.1 (M+H)$^+$, RT 1.70 minutes (method 1).

Intermediate 96 tert-Butyl 4-(5-aminothiazolo[5,4-d]pyrimidin-7-yl)-3-(hydroxymethyl)piperazine-1-carboxylate Prepared from Intermediate 4 and tert-butyl 3-(hydroxymethyl)piperazine-1-carboxylate following the method used to prepare Intermediate 95. LCMS (ES+) 367.1 (M+H)$^+$, RT 1.63 minutes (method 1).

Intermediate 97 tert-Butyl 4-(5-aminothiazolo[5,4-d]pyrimidin-7-yl)-2-methylpiperazine-1-carboxylate Prepared from Intermediate 4 and tert-butyl 2-methylpiperazine-1-carboxylate following the method used to prepare Intermediate 95. LCMS (ES+) 351.05 (M+H)$^+$, RT 1.87 minutes (method 1).

Intermediate 98 tert-Butyl (2R)-4-(5-aminothiazolo[5,4-d]pyrimidin-7-yl)-2-(hydroxymethyl)-piperazine-1-carboxylate Prepared from Intermediate 4 and tert-butyl (2R)-2-(hydroxymethyl)piperazine-1-carboxylate following the method used to prepare Intermediate 95. LCMS (ES+) 367.1 (M+H)$^+$, RT 1.64 minutes (method 1).

Intermediate 99 tert-Butyl (2S)-4-(5-aminothiazolo[5,4-d]pyrimidin-7-yl)-2-(hydroxymethyl)-piperazine-1-carboxylate Prepared from Intermediate 4 and tert-butyl (2S)-2-(hydroxymethyl)piperazine-1-carboxylate following the method used to prepare Intermediate 95. LCMS (ES+) 367.1 (M+H)$^+$, RT 1.55 minutes (method 1).

Intermediate 100 tert-Butyl 4-(5-aminothiazolo[5,4-d]pyrimidin-7-yl)-3-methylpiperazine-1-carboxylate Prepared from Intermediate 4 and tert-butyl 3-methylpiperazine-1-carboxylate following the method used to prepare Intermediate 95. LCMS (ES+) 351.15 (M+H)$^+$, RT 1.91 minutes (method 1).

Intermediate 101 tert-Butyl 4-(5-aminothiazolo[5,4-d]pyrimidin-7-yl)-2,3-dimethylpiperazine-1-carboxylate Prepared from Intermediate 4 and tert-butyl 2,3-dimethylpiperazine-1-carboxylate following the method used to prepare Intermediate 95. LCMS (ES+) 365.15 (M+H)$^+$, RT 1.98 minutes (method 1).

Intermediate 102 tert-Butyl (2R,5S)-4-(5-aminothiazolo[5,4-d]pyrimidin-7-yl)-2,5-dimethylpiperazine-1-carboxylate Prepared from Intermediate 4 and tert-butyl (2R,5S)-2,5-dimethylpiperazine-1-carboxylate following the method used to prepare Intermediate 95. LCMS (ES+) 365.25 (M+H)$^+$, RT 2.11 minutes (method 1).

Intermediate 103

7-(2,5-Diazabicyclo[2.2.1]heptan-2-yl)thiazolo[5,4-d]pyrimidin-5-amine

To a solution of Intermediate 95 (1 g, 2.86 mmol) in DCM (10 mL) was added TMSOTf (1.56 mL, 8.58 mmol) followed by 2,6-lutidine (0.8 mL, 7.1 mmol), and the reaction mixture was stirred at room temperature for 12 h. The reaction mixture was then concentrated, and the crude material obtained was purified by column chromatography (silica: 100-200 mesh, MeOH:DCM 5% to 7%), to afford the title compound (0.5 g, 70.4%). LCMS (ES+) 249.05 (M+H)$^+$, RT 0.52 minutes (method 1).

Intermediate 104

[1-(5-Aminothiazolo[5,4-d]pyrimidin-7-yl)piperazin-2-yl]methanol

Prepared from Intermediate 96 following the method used to prepare Intermediate 103. LCMS (ES+) 267 (M+H)$^+$, RT 0.71 minutes (method 1).

Intermediate 105

7-(3-Methylpiperazin-1-yl)thiazolo[5,4-d]pyrimidin-5-amine

Prepared from Intermediate 97 following the method used to prepare Intermediate 103. LCMS (ES+) 249.05 (M+H)$^+$, RT 0.52 minutes (method 1).

Intermediate 106

[(2R)-4-(5-Aminothiazolo[5,4-d]pyrimidin-7-yl)piperazin-2-yl]methanol

Prepared from Intermediate 98 following the method used to prepare Intermediate 103. LCMS (ES+) 267.05 (M+H)$^+$, RT 0.71 minutes (method 1).

Intermediate 107

[(2S)-4-(5-Aminothiazolo[5,4-d]pyrimidin-7-yl)piperazin-2-yl]methanol

Prepared from Intermediate 99 following the method used to prepare Intermediate 103. LCMS (ES+) 267.05 (M+H)$^+$, RT 0.69 minutes (method 1).

Intermediate 108

7-(2-Methylpiperazin-1-yl)thiazolo[5,4-d]pyrimidin-5-amine

Prepared from Intermediate 100 following the method used to prepare Intermediate 103. LCMS (ES+) 250.95 (M+H)$^+$, RT 0.53 minutes (method 1).

Intermediate 109

7-(2,3-Dimethylpiperazin-1-yl)thiazolo[5,4-d]pyrimidin-5-amine

Prepared from Intermediate 101 following the method used to prepare Intermediate 103. LCMS (ES+) 265.1 (M+H)$^+$, RT 0.65 minutes (method 1).

Intermediate 110

7-[(2S,5R)-2,5-Dimethylpiperazin-1-yl]thiazolo[5,4-d]pyrimidin-5-amine

Prepared from Intermediate 102 following the method used to make Intermediate 103. LCMS (ES+) 265.1 (M+H)$^+$, RT 0.69 minutes (method 1).

Examples 1 to 248

General Experimental Procedures

Procedure 1: Acid-Amine Coupling Reaction

To a solution of the appropriate carboxylic acid (0.762 mmol) in DMF (2 mL), maintained at 0° C., were added HATU (1.14 mmol) and DIPEA (2.28 mmol). After 5 minutes, Intermediate 3 or Intermediate 6 (as appropriate; 0.635 mmol) was added and the reaction mixture was stirred at room temperature for 12 h. The progress of the reaction was monitored by LCMS. Upon completion, the reaction mixture was diluted with water and extracted with ethyl acetate. The organic layer was washed with brine, then water, and dried over sodium sulphate. The organic layer was concentrated under vacuum and the resulting crude material was purified by column chromatography (silica gel: 100-200 mesh, MeOH:DCM 1:9) to afford the desired compound.

Procedure 2: Isocyanate-Amine Coupling Reaction

To a solution of Intermediate 3 (200 mg, 0.735 mmol) in DMF (2 mL) were added triethylamine (2.20 mmol) and the appropriate isocyanate (0.735 mmol). The reaction mixture was stirred at room temperature for 4 h. The progress of the reaction was monitored by LCMS. Upon completion, the reaction mixture was concentrated and the resulting material was purified by column chromatography (silica gel: 100-200 mesh, MeOH:DCM 1:9) to afford the desired compound.

Procedure 3: N-Alkylation Reaction

To a stirred solution of Intermediate 3 (50 mg, 0.18 mmol) in DMF (2 mL), maintained at 0° C., was added $Cs_2CO_3$ (0.73 mmol) followed by the appropriate alkyl halide (0.24 mmol). The reaction mixture was stirred at room temperature for 12 h. The progress of the reaction was monitored by LCMS. Upon completion, the reaction mixture was diluted with water and extracted with ethyl acetate. The organic layer was washed with water and brine. The organic layer was then dried over sodium sulphate and concentrated under vacuum. The resulting crude material was purified by column chromatography (silica gel: 100-200 mesh, MeOH:DCM 1:9) to afford the desired compound.

Procedure 4: Displacement Reaction

To a stirred solution of Intermediate 6 (0.1 g, 0.4 mmol) in EtOH was added Intermediate 20 or Intermediate 21 (as appropriate; 1 eq) followed by triethylamine (1 eq). The resulting mixture was stirred at room temperature for 30 minutes. The reaction mixture was then concentrated, and the resulting crude material was diluted with DCM. The organic layer was washed with water and brine. The organic layer was then concentrated and the resulting crude material was purified by column chromatography (silica: 100-200 mesh, MeOH:DCM 2-4%) to afford the desired compound.

Procedure 5: Urea Formation Using Amine and CDI

To a stirred solution of the appropriate amine (0.48 mmol) in DMF (1 mL) were added DIPEA (0.075 mL, 0.44 mmol) and CDI (0.077 g, 0.48 mmol). The reaction mixture was stirred at room temperature for 30 minutes. To this mixture was added a solution of Intermediate 3 or Intermediate 6 (as appropriate; 0.4 mmol) and DIPEA (0.1 mL, 0.48 mmol) in DMF (1 mL). The reaction mixture was stirred at room temperature for a further 12 h. The reaction mixture was then diluted with EtOAc, and the organic layer was washed with water and brine. The organic layer was dried over anhydrous sodium sulphate, then concentrated. The resulting crude material was purified by column chromatography (silica: 100-200 mesh, MeOH:DCM 5-7%) to afford the desired compound.

Procedure 6: Urea Formation Using Amine and Phenyl Chloroformate

To a solution of the appropriate amine (1.05 mmol) in THF (5 mL) at 0° C. was added pyridine (0.11 mL, 1.32 mmol), followed by phenyl chloroformate (0.14 mL, 1.11 mmol). The reaction mixture was stirred at 0° C. for 2 h. The reaction mixture was then diluted with EtOAc and washed successively with 2M HCl solution, then water, then saturated aqueous sodium bicarbonate solution. The organic layer was concentrated. To a solution of the resulting crude material (0.48 mmol) and Intermediate 6 (0.1 g, 0.4 mmol) in DMSO (2 mL) was added DIPEA (0.061 mL, 1.2 mmol) and the reaction mixture was heated at 60° C. for 3 h. The reaction mixture was then diluted with EtOAc, and the organic layer was washed with water. The organic layer was separated and concentrated, and the resulting crude material was purified by column chromatography (silica: 100-200 mesh, MeOH:DCM 3-7%) to afford the desired compound.

Procedure 7: Isocyanate-Amine Coupling: Alternative Reaction Conditions

To a solution of Intermediate 6 or Intermediate 80 (as appropriate; 0.6 mmol) in DCM (10 mL) was added DIPEA (0.2 mL), followed by the appropriate isocyanate (1 eq). The reaction mixture was stirred at room temperature for 48 h. After this time, the reaction mixture was partitioned between DCM and water. The organic layers were separated and dried, then the resulting crude material was purified by preparative HPLC to afford the desired compound.

Procedure 8: Urea Formation Using Amine and Triphosgene

To a solution of the appropriate amine (0.404 mmol) in DCM (2 mL) were added DIPEA (0.104 g, 0.807 mmol) and triphosgene (39 mg, 0.132 mmol). The mixture was stirred at room temperature for 30 minutes. A solution of Intermediate 3 (0.1 g, 0.367 mmol) in DCM (3 mL) and DIPEA (0.104 g, 0.807 mmol) was added. The mixture was stirred at room temperature for 2 h. The reaction mixture was diluted with water and extracted with EtOAc. The organic layer was washed with brine and then water, and dried over sodium sulphate. The organic layer was concentrated in vacuo, and the resulting crude material was purified by column chromatography (silica gel: 100-200 mesh, MeOH:DCM 1:9) to afford the desired compound.

Procedure 9: Carbamate Synthesis

To a solution of Intermediate 3 (0.2 g, 0.735 mmol) in DCM (10 mL) were added DIPEA (1.83 mmol) and the appropriate chloroformate (0.771 mmol). The reaction mixture was stirred at room temperature for 1 h. The reaction mixture was then diluted with water, and extracted with EtOAc. The organic layer was washed with brine, then water, and dried over sodium sulphate. The organic layer was concentrated under vacuum, and the resulting crude material was purified by column chromatography (silica gel: 100-200 mesh, MeOH:DCM 1:9) to afford the desired compound.

Procedure 10: Removal of BOC Protecting Group

The appropriate BOC-protected amine was stirred with 4N HCl in 1,4-dioxane until no starting material remained. The reaction mixture was then concentrated in vacuo and triturated with diethyl ether to yield the desired compound as the HCl salt.

Examples 1 to 44

The following compounds were synthesised from Intermediate 3 and commercial reagents in accordance with the specified procedure.

| Ex. | Name | Expt. Procedure | Method | RT | $[M + H]^+$ |
|---|---|---|---|---|---|
| 1 | 1-[4-(5-Aminothiazolo[5,4-d]pyrimidin-7-yl)piperazin-1-yl]-2-(4-methoxyphenoxy)-ethanone | 1 | 2 | 1.69 | 401.0 |
| 2 | 4-(5-Aminothiazolo[5,4-d]pyrimidin-7-yl)-piperazine-1-carboxylic acid p-tolylamide | 2 | 2 | 1.74 | 370.0 |

-continued

| Ex. | Name | Expt. Procedure | LCMS Data Method | RT | [M + H]+ |
|---|---|---|---|---|---|
| 3 | 4-(5-Aminothiazolo[5,4-d]pyrimidin-7-yl)-piperazine-1-carboxylic acid (3-methoxy-phenyl)amide | 2 | 2 | 1.65 | 386.0 |
| 4 | 4-(5-Aminothiazolo[5,4-d]pyrimidin-7-yl)-piperazine-1-carboxylic acid (3,4,5-trimethoxyphenyl)amide | 2 | 2 | 1.56 | 446.0 |
| 5 | 4-(5-Aminothiazolo[5,4-d]pyrimidin-7-yl)-piperazine-1-carboxylic acid (3,5-dimethyl-isoxazol-4-yl)amide | 2 | 2 | 1.20 | 375.0 |
| 6 | 4-(5-Aminothiazolo[5,4-d]pyrimidin-7-yl)-piperazine-1-carboxylic acid (2,5-dimethoxyphenyl)amide | 2 | 2 | 1.77 | 416.0 |
| 7 | 4-(5-Aminothiazolo[5,4-d]pyrimidin-7-yl)-piperazine-1-carboxylic acid (3,5-dimethoxyphenyl)amide | 2 | 2 | 1.72 | 416.0 |
| 8 | 1-[4-(5-Aminothiazolo[5,4-d]pyrimidin-7-yl)piperazin-1-yl]-2-(pyridin-4-yl)ethanone | 1 | 1 | 1.412 | 356.2 |
| 9 | 1-[4-(5-Aminothiazolo[5,4-d]pyrimidin-7-yl)piperazin-1-yl]-2-phenoxyethanone | 1 | 1 | 1.836 | 371.1 |
| 10 | 1-[4-(5-Aminothiazolo[5,4-d]pyrimidin-7-yl)piperazin-1-yl]-3-(1H-benzo[d]imidazol-2-yl)propan-1-one | 1 | 1 | 1.531 | 409.2 |
| 11 | 1-[4-(5-Aminothiazolo[5,4-d]pyrimidin-7-yl)piperazin-1-yl]-3-phenylpropan-1-one | 1 | 1 | 2.138 | 369.2 |
| 12 | [4-(5-Aminothiazolo[5,4-d]pyrimidin-7-yl)-piperazin-1-yl](phenyl)methanone | 1 | 1 | 1.906 | 341.1 |
| 13 | [4-(5-Aminothiazolo[5,4-d]pyrimidin-7-yl)-piperazin-1-yl](pyridin-3-yl)methanone | 1 | 1 | 1.400 | 342.1 |
| 14 | 7-[4-(Pyridin-3-ylmethyl)piperazin-1-yl]-thiazolo[5,4-d]pyrimidin-5-amine | 3 | 1 | 1.471 | 328.1 |
| 15 | 1-[4-(5-Aminothiazolo[5,4-d]pyrimidin-7-yl)piperazin-1-yl]-3-(4-fluorophenyl)-propan-1-one | 1 | 1 | 2.023 | 387.2 |
| 16 | 1-[4-(5-Aminothiazolo[5,4-d]pyrimidin-7-yl)piperazin-1-yl]-3-(4-methoxyphenyl)-propan-1-one | 1 | 1 | 1.933 | 399.2 |
| 17 | 1-[4-(5-Aminothiazolo[5,4-d]pyrimidin-7-yl)piperazin-1-yl]-3-(2-methoxyphenyl)-propan-1-one | 1 | 1 | 2.018 | 399.1 |
| 18 | 1-[4-(5-Aminothiazolo[5,4-d]pyrimidin-7-yl)piperazin-1-yl]-3-(p-tolyl)propan-1-one | 1 | 1 | 2.187 | 383.2 |
| 19 | 1-[4-(5-Aminothiazolo[5,4-d]pyrimidin-7-yl)piperazin-1-yl]-3-(furan-2-yl)propan-1-one | 1 | 1 | 1.950 | 359.1 |
| 20 | [4-(5-Aminothiazolo[5,4-d]pyrimidin-7-yl)-piperazin-1-yl](1-methyl-1H-imidazol-5-yl)methanone | 1 | 1 | 1.318 | 345.2 |
| 21 | 1-[4-(5-Aminothiazolo[5,4-d]pyrimidin-7-yl)piperazin-1-yl]-2-(morpholin-4-yl)-ethanone | 1 | 1 | 1.339 | 364.3 |
| 22 | [4-(5-Aminothiazolo[5,4-d]pyrimidin-7-yl)-piperazin-1-yl](imidazo[1,2-a]pyridin-2-yl)methanone | 1 | 1 | 1.715 | 381.2 |
| 23 | 1-[4-(5-Aminothiazolo[5,4-d]pyrimidin-7-yl)piperazin-1-yl]-3-(pyridin-3-yl)propan-1-one | 1 | 1 | 1.568 | 370.2 |
| 24 | [4-(5-Aminothiazolo[5,4-d]pyrimidin-7-yl)piperazin-1-yl](imidazo[1,2-a]pyridin-3-yl)methanone | 1 | 1 | 1.583 | 381.2 |
| 25 | 4-(5-Aminothiazolo[5,4-d]pyrimidin-7-yl)-N-(o-tolyl)piperazine-1-carboxamide | 2 | 1 | 1.72 | 369.4 |
| 26 | 4-(5-Aminothiazolo[5,4-d]pyrimidin-7-yl)-N-benzylpiperazine-1-carboxamide | 2 | 1 | 1.70 | 369.4 |
| 27 | 4-(5-Aminothiazolo[5,4-d]pyrimidin-7-yl)-N-(m-tolyl)piperazine-1-carboxamide | 2 | 1 | 1.87 | 369.4 |
| 28 | 4-(5-Aminothiazolo[5,4-d]pyrimidin-7-yl)-N-(1-phenylethyl)piperazine-1-carboxamide | 2 | 1 | 1.83 | 383.4 |
| 29 | 4-(5-Aminothiazolo[5,4-d]pyrimidin-7-yl)-N-[4-(difluoromethoxy)phenyl]piperazine-1-carboxamide | 2 | 1 | 2.365 | 422.2 |
| 30 | 4-(5-Aminothiazolo[5,4-d]pyrimidin-7-yl)-N-[4-(trifluoromethoxy)phenyl]piperazine-1-carboxamide | 2 | 1 | 2.566 | 440.3 |
| 31 | 4-(5-Aminothiazolo[5,4-d]pyrimidin-7-yl)-N-(4-methoxybenzyl)piperazine-1-carboxamide | 2 | 1 | 2.611 | 400.2 |

| Ex. | Name | Expt. Procedure | LCMS Method | RT | [M + H]+ |
|---|---|---|---|---|---|
| 32 | [4-(5-Aminothiazolo[5,4-d]pyrimidin-7-yl)-piperazin-1-yl](pyrazin-2-yl)methanone | 1 | 1 | 1.289 | 343.1 |
| 33 | 1-[4-(5-Aminothiazolo[5,4-d]pyrimidin-7-yl)piperazin-1-yl]-3-(o-tolyl)propan-1-one | 1 | 1 | 2.126 | 383.1 |
| 34 | [4-(5-Aminothiazolo[5,4-d]pyrimidin-7-yl)-piperazin-1-yl](quinolin-2-yl)methanone | 1 | 1 | 1.835 | 392.1 |
| 35 | [4-(5-Aminothiazolo[5,4-d]pyrimidin-7-yl)-piperazin-1-yl](quinoxalin-2-yl)methanone | 1 | 1 | 1.766 | 393.2 |
| 36 | 1-[4-(5-Aminothiazolo[5,4-d]pyrimidin-7-yl)piperazin-1-yl]-3-(3-methoxyphenyl)-propan-1-one | 1 | 1 | 1.999 | 399.1 |
| 37 | [4-(5-Aminothiazolo[5,4-d]pyrimidin-7-yl)-piperazin-1-yl](1-methyl-1H-imidazol-2-yl)methanone | 1 | 1 | 1.325 | 345.0 |
| 38 | 1-[4-(5-Aminothiazolo[5,4-d]pyrimidin-7-yl)piperazin-1-yl]-3-cyclopentylpropan-1-one | 1 | 1 | 2.410 | 361.2 |
| 39 | [4-(5-Aminothiazolo[5,4-d]pyrimidin-7-yl)-piperazin-1-yl](1H-benzo[d]imidazol-2-yl)-methanone | 1 | 1 | 1.765 | 381.2 |
| 40 | (S)-1-[4-(5-Aminothiazolo[5,4-d]pyrimidin-7-yl)piperazin-1-yl]-3-hydroxy-3-phenyl-propan-1-one | 1 | 1 | 1.602 | 385.5 |
| 41 | [4-(5-Aminothiazolo[5,4-d]pyrimidin-7-yl)-piperazin-1-yl](1H-pyrazol-3-yl)methanone | 1 | 1 | 1.388 | 331.1 |
| 42 | [4-(5-Aminothiazolo[5,4-d]pyrimidin-7-yl)-piperazin-1-yl](isoquinolin-3-yl)methanone | 1 | 1 | 1.784 | 392.2 |
| 43 | [4-(5-Aminothiazolo[5,4-d]pyrimidin-7-yl)-piperazin-1-yl](1H-indazol-3-yl)methanone | 1 | 1 | 1.768 | 381.4 |
| 44 | [4-(5-Aminothiazolo[5,4-d]pyrimidin-7-yl)-piperazin-1-yl](5-methyl-1H-pyrazol-3-yl)-methanone | 1 | 1 | 1.408 | 345.3 |

Examples 45 to 51

The following compounds were synthesised from Intermediate 3 and commercial reagents in accordance with the specified procedure.

Example 45

4-(5-Aminothiazolo[5,4-d]pyrimidin-7-yl)piperazine-1-carboxylic acid (2,3-dihydrobenzo[1,4]dioxin-6-yl)amide Procedure 2. $\delta_H$(DMSO-$d_6$) 8.71 (s, 1H), 8.38 (s, 1H), 7.06 (d, J=2.4 Hz, 1H), 6.88 (dd, J2.5, 8.8 Hz, 1H), 6.72 (d, J=8.7 Hz, 1H), 6.38 (s, 2H), 4.27-4.12 (m, 8H), 3.60-3.50 (m, 4H). LCMS (ES+) 414.0 (M+H)+, RT 1.58 minutes (method 2).

Example 46

4-(5-Aminothiazolo[5,4-d]pyrimidin-7-yl)piperazine-1-carboxylic acid (3,4-dimethoxyphenyl)amide Procedure 2. $\delta_H$(DMSO-$d_6$) 8.71 (s, 1H), 8.42 (s, 1H), 7.18 (d, J=2.4 Hz, 1H), 6.98 (dd, J2.4, 8.7 Hz, 1H), 6.86-6.81 (m, 1H), 6.38 (s, 2H), 4.30-4.12 (m, 4H), 3.72 (s, 3H), 3.70 (s, 3H), 3.60-3.53 (m, 4H). LCMS (ES+) 416.0 (M+H)+, RT 1.49 minutes (method 2).

Example 47

4-(5-Aminothiazolo[5,4-d]pyrimidin-7-yl)piperazine-1-carboxylic acid [4-(dimethylamino)phenyl]amide Procedure 2. $\delta_H$(DMSO-$d_6$) 8.71 (s, 1H), 8.27 (s, 1H), 7.25 (d, J=9.1 Hz, 2H), 6.67 (d, J 9.1 Hz, 2H), 6.38 (s, 2H), 4.27-4.18 (m, 4H), 3.60-3.53 (m, 4H), 2.83 (s, 6H). LCMS (ES+) 399.0 (M+H)+, RT 1.62 minutes (method 2).

Example 48

4-(5-Aminothiazolo[5,4-d]pyrimidin-7-yl)piperazine-1-carboxylic acid (2,4-dimethoxyphenyl)amide Procedure 2. $\delta_H$(DMSO-$d_6$) 8.71 (s, 1H), 7.65 (s, 1H), 7.35 (d, J=8.7 Hz, 1H), 6.59 (d, J=2.7 Hz, 1H), 6.46 (dd, J 2.7, 8.7 Hz, 1H), 6.38 (s, 2H), 4.27-4.18 (m, 4H), 3.78 (s, 3H), 3.74 (s, 3H), 3.58-3.50 (m, 4H). LCMS (ES+) 416.0 (M+H)+, RT 1.64 minutes (method 2).

Example 49

4-(5-Aminothiazolo[5,4-d]pyrimidin-7-yl)piperazine-1-carboxylic acid (4-methoxy-2-methylphenyl)amide Procedure 2. $\delta_H$(DMSO-$d_6$) 8.71 (s, 1H), 8.01 (s, 1H), 7.06 (d, J=8.6 Hz, 1H), 6.78 (d, J=2.9 Hz, 1H), 6.71 (dd, J 2.9, 8.6 Hz, 1H), 6.39 (s, 2H), 4.30-4.18 (m, 4H), 3.73 (s, 3H), 3.60-3.53 (m, 4H), 2.15 (s, 3H). LCMS (ES+) 400.0 (M+H)+, RT 1.67 minutes (method 2).

Example 50

4-(5-Aminothiazolo[5,4-d]pyrimidin-7-yl)piperazine-1-carboxylic acid (4-methoxyphenyl)amide Procedure 2. $\delta_H$(DMSO-$d_6$) 8.71 (s, 1H), 8.42 (s, 1H), 7.36 (d, J=9.0 Hz, 2H), 6.84 (d, J 9.1 Hz, 2H), 6.39 (s, 2H), 4.30-4.18 (m, 4H), 3.72 (s, 3H), 3.60-3.54 (m, 4H). LCMS (ES+) 386.0 (M+H)+, RT 1.57 minutes (method 2).

Example 51

4-(5-Aminothiazolo[5,4-d]pyrimidin-7-yl)-N-(2-methoxyphenyl)-piperazine-1-carboxamide Procedure 2. $\delta_H$ (DMSO-$d_6$) 8.71 (s, 1H), 7.73 (s, 1H), 7.67-7.65 (m, 1H), 7.05-7.00 (m, 2H), 6.90-6.86 (m, 1H), 6.38 (s, 2H), 4.25 (s, 4H), 3.82 (s, 3H), 3.59-3.56 (m, 4H). LCMS (ES+) 386.3 (M+H)+, RT 1.30 minutes (method 2).

Examples 52 to 86

The following compounds were synthesised from Intermediate 3 and commercial reagents (except for Example 81, which was derived from Example 80) in accordance with the specified procedure.

| Ex. | Name | Expt. Procedure | Method | RT | [M + H]+ |
|---|---|---|---|---|---|
| 52 | 1-[4-(5-Aminothiazolo[5,4-d]pyrimidin-7-yl)piperazin-1-yl]-2-(4-chlorophenoxy)-ethanone | 1 | 2 | 1.924 | 405.0 |
| 53 | 4-(5-Aminothiazolo[5,4-d]pyrimidin-7-yl)-N-(2,4-dimethylphenyl)piperazine-1-carboxamide | 2 | 2 | 1.903 | 384.0 |
| 54 | 4-(5-Aminothiazolo[5,4-d]pyrimidin-7-yl)-N-{4-[2-(morpholin-4-yl)ethoxy]phenyl}-piperazine-1-carboxamide | 8 | 2 | 1.605 | 485.8 |
| 55 | Isopropenyl 4-(5-aminothiazolo[5,4-d]-pyrimidin-7-yl)piperazine-1-carboxylate | 9 | 2 | 1.813 | 321.7 |
| 56 | 4-(5-Aminothiazolo[5,4-d]pyrimidin-7-yl)-N-(cyclopropylmethyl)piperazine-1-carboxamide | 5 | 2 | 1.478 | 334.8 |
| 57 | 4-(5-Aminothiazolo[5,4-d]pyrimidin-7-yl)-N-[4-(morpholin-4-yl)phenyl]piperazine-1-carboxamide | 5 | 2 | 1.564 | 441.7 |
| 58 | 4-(5-Aminothiazolo[5,4-d]pyrimidin-7-yl)-N-[4-(imidazol-1-yl)phenyl]piperazine-1-carboxamide | 5 | 2 | 1.40 | 422.6 |
| 59 | 4-(5-Aminothiazolo[5,4-d]pyrimidin-7-yl)-N-(1H-indazol-5-yl)piperazine-1-carboxamide | 5 | 2 | 1.34 | 396.7 |
| 60 | 4-(5-Aminothiazolo[5,4-d]pyrimidin-7-yl)-N-(quinoxalin-6-yl)piperazine-1-carboxamide | 5 | 2 | 1.33 | 408.6 |
| 61 | 4-(5-Aminothiazolo[5,4-d]pyrimidin-7-yl)-N-(2-phenoxyethyl)piperazine-1-carboxamide | 5 | 2 | 1.66 | 400.8 |
| 62 | 4-(5-Aminothiazolo[5,4-d]pyrimidin-7-yl)-N-(3-fluoro-4-methoxyphenyl)piperazine-1-carboxamide | 5 | 2 | 1.61 | 404.8 |
| 63 | 4-(5-Aminothiazolo[5,4-d]pyrimidin-7-yl)-N-(1-methylbenzimidazol-2-yl)piperazine-1-carboxamide | 5 | 2 | 1.82 | [M − H]− 408.0 |
| 64 | 4-(5-Aminothiazolo[5,4-d]pyrimidin-7-yl)-N-[4-(pyrazol-1-yl)phenyl]piperazine-1-carboxamide | 5 | 2 | 1.57 | 422.8 |
| 65 | 4-(5-Aminothiazolo[5,4-d]pyrimidin-7-yl)-N-(imidazo[1,2-a]pyridin-3-yl)piperazme-1-carboxamide | 5 | 2 | 1.16 | 396.7 |
| 66 | 4-(5-Aminothiazolo[5,4-d]pyrimidin-7-yl)-N-[2-(piperidin-1-ylmethyl)-3H-benzimidazol-5-yl]piperazine-1-carboxamide | 5 | 2 | 1.48 | 493.8 |
| 67 | 4-(5-Aminothiazolo[5,4-d]pyrimidin-7-yl)-N-[2-(morpholin-4-ylmethyl)-3H-benzimidazol-5-yl]piperazine-1-carboxamide | 5 | 2 | 1.22 | 495.8 |
| 68 | 4-(5-Aminothiazolo[5,4-d]pyrimidin-7-yl)-N-(indan-5-yl)piperazine-1-carboxamide | 5 | 2 | 1.93 | 396.7 |
| 69 | 4-(5-Aminothiazolo[5,4-d]pyrimidin-7-yl)-N-(4-methoxy-1,3-benzothiazol-2-yl)-piperazine-1-carboxamide | 5 | 2 | 1.65 | 443.6 |
| 70 | 4-(5-Aminothiazolo[5,4-d]pyrimidin-7-yl)-N-(3-methyl-1H-pyrazol-5-yl)piperazine-1-carboxamide | 5 | 2 | 1.13 | 360.8 |
| 71 | 4-(5-Aminothiazolo[5,4-d]pyrimidin-7-yl)-N-(1H-indazol-6-yl)piperazine-1-carboxamide | 5 | 2 | 1.33 | 396.7 |
| 72 | 4-(5-Aminothiazolo[5,4-d]pyrimidin-7-yl)-N-(1-methyl-2-oxopyrrolidin-3-yl)-piperazine-1-carboxamide | 5 | 2 | 0.97 | 377.8 |

-continued

| Ex. | Name | Expt. Procedure | LCMS Data Method | RT | [M + H]+ |
|---|---|---|---|---|---|
| 73 | 4-(5-Aminothiazolo[5,4-d]pyrimidin-7-yl)-N-(4-tert-butylthiazol-2-yl)piperazine-1-carboxamide | 5 | 2 | 2.04 | 419.6 |
| 74 | Ethyl 2-{[4-(5-aminothiazolo[5,4-d]pyrimidin-7-yl)piperazine-1-carbonyl]-amino}thiazole-5-carboxylate | 5 | 2 | 1.21 | 435.6 |
| 75 | Benzyl 2-{[4-(5-aminothiazolo[5,4-d]pyrimidin-7-yl)piperazine-1-carbonyl]-amino}acetate | 5 | 2 | 1.62 | 428.7 |
| 76 | tert-Butyl 2-{[4-(5-aminothiazolo[5,4-d]pyrimidin-7-yl)piperazine-1-carbonyl]-amino}acetate | 5 | 2 | 1.48 | 394.8 |
| 77 | 4-(5-Aminothiazolo[5,4-d]pyrimidin-7-yl)-N-(4-methylthiazol-2-yl)piperazine-1-carboxamide | 5 | 2 | 1.41 | 377.6 |
| 78 | 4-(5-Aminothiazolo[5,4-d]pyrimidin-7-yl)-N-(6-methoxypyridin-3-yl)piperazine-1-carboxamide | 5 | 2 | 1.34 | 387.7 |
| 79 | 4-(5-Aminothiazolo[5,4-d]pyrimidin-7-yl)-N-(pyridin-4-yl)piperazine-1-carboxamide | 5 | 2 | 1.18 | 357.7 |
| 80 | tert-Butyl 3-(4-{[4-(5-aminothiazolo[5,4-d]pyrimidin-7-yl)piperazine-1-carbonyl]-amino}-3-methylphenoxy)azetidine-1-carboxylate | 5 | 2 | 2.15 | 541.8 |
| 81 | 4-(5-Aminothiazolo[5,4-d]pyrimidin-7-yl)-N-[4-(azetidin-3-yloxy)-2-methylphenyl]-piperazine-1-carboxamide | 10 | 2 | 1.137 | 441.8 |
| 82 | 4-(5-Aminothiazolo[5,4-d]pyrimidin-7-yl)-N-(1-methylindolin-5-yl)piperazine-1-carboxamide | 2 | 2 | 1.72 | 411.0 |
| 83 | 4-(5-Aminothiazolo[5,4-d]pyrimidin-7-yl)-N-(2,3-dihydrobenzofuran-5-yl)piperazine-1-carboxamide | 2 | 2 | 1.64 | 398.0 |
| 84 | 4-(5-Aminothiazolo[5,4-d]pyrimidin-7-yl)-N-(1-methylindol-6-yl)piperazine-1-carboxamide | 2 | 2 | 1.79 | 409.0 |
| 85 | 4-(5-Aminothiazolo[5,4-d]pyrimidin-7-yl)-N-(3-methylfuran-2-yl)piperazine-1-carboxamide | 2 | 2 | 1.41 | 360.0 |
| 86 | 4-(5-Aminothiazolo[5,4-d]pyrimidin-7-yl)-N-(thien-3-yl)piperazine-1-carboxamide | 2 | 2 | 1.61 | 362.0 |

Examples 87 to 184

The following compounds were synthesised from Intermediate 6 in accordance with the specified procedure.

Examples 87-122, 125-138, 163, 166-174 and 182 utilised commercial reagents.

Examples 123, 124, 139-162, 164, 165, 175, 176, 179, 181 and 183 utilised Intermediates 21, 20, 23, 22, 24-26, 37, 35, 36, 38, 43-45, 55-63, 65, 68, 71, 72, 74, 89, 84 and 90-92 respectively.

Example 177 utilised an amine disclosed in WO 2008/042282.

Examples 178, 180 and 184 were derived from Examples 177, 179 and 183 respectively.

| Ex. | Name | Expt. Procedure | LCMS Data Method | RT | [M + H]+ |
|---|---|---|---|---|---|
| 87 | (S)-4-[4-(5-Aminothiazolo[5,4-d]pyrimidin-7-yl)-3-methylpiperazine-1-carboxamido]-phenyl benzoate | 6 | 1 | 2.35 | 490.1 |
| 88 | (S)-4-(5-Aminothiazolo[5,4-d]pyrimidin-7-yl)-N-[4-(cyanomethyl)phenyl]-3-methyl-piperazine-1-carboxamide | 6 | 1 | 1.73 | 409.2 |
| 89 | (S)-4-(5-Aminothiazolo[5,4-d]pyrimidin-7-yl)-3-methyl-N-(pyridin-2-yl)piperazine-1-carboxamide | 6 | 1 | 1.66 | 371.1 |

| Ex. | Name | Expt. Procedure | LCMS Data Method | RT | [M + H]+ |
|---|---|---|---|---|---|
| 90 | (S)-4-(5-Aminothiazolo[5,4-d]pyrimidin-7-yl)-3-methyl-N-(pyrimidin-2-yl)piperazine-1-carboxamide | 6 | 1 | 1.26 | 372.1 |
| 91 | (S)-4-(5-Aminothiazolo[5,4-d]pyrimidin-7-yl)-3-methyl-N-(pyridin-3-yl)piperazme-1-carboxamide | 6 | 1 | 1.43 | 371.0 |
| 92 | (S)-N-(4-Acetamidophenyl)-4-(5-aminothiazolo[5,4-d]pyrimidin-7-yl)-3-methyl-piperazine-1-carboxamide | 6 | 1 | 1.43 | 427.2 |
| 93 | (S)-4-(5-Aminothiazolo[5,4-d]pyrimidin-7-yl)-N-(4-ethylphenyl)-3-methylpiperazine-1-carboxamide | 6 | 1 | 2.18 | 398.2 |
| 94 | (S)-4-(5-Aminothiazolo[5,4-d]pyrimidin-7-yl)-N-(2,2-difluorobenzo[d][1,3]dioxol-5-yl)-3-methylpiperazine-1-carboxamide | 6 | 1 | 2.27 | 450.1 |
| 95 | (S)-4-(5-Aminothiazolo[5,4-d]pyrimidin-7-yl)-3-methyl-N-[2-(trifluoromethyl)-1H-benzo[d]imidazol-6-yl]piperazine-1-carboxamide | 6 | 1 | 1.48 | 478.2 |
| 96 | (S)-4-(5-Aminothiazolo[5,4-d]pyrimidin-7-yl)-N-(benzo[d]thiazol-6-yl)-3-methyl-piperazine-1-carboxamide | 6 | 1 | 1.76 | 427.2 |
| 97 | (S)-4-(5-Aminothiazolo[5,4-d]pyrimidin-7-yl)-3-methyl-N-(thiazol-2-yl)piperazine-1-carboxamide | 6 | 1 | 1.64 | 377.1 |
| 98 | (S)-4-(5-Aminothiazolo[5,4-d]pyrimidin-7-yl)-3-methyl-N-[2-(morpholin-4-yl)ethyl]-piperazine-1-carboxamide | 6 | 1 | 1.40 | 407.2 |
| 99 | (S)-4-(5-Aminothiazolo[5,4-d]pyrimidin-7-yl)-3-methyl-N-(4-nitrophenyl)piperazine-1-carboxamide | 6 | 1 | 2.02 | 415.2 |
| 100 | (S)-4-(5-Aminothiazolo[5,4-d]pyrimidin-7-yl)-N-(4-carbamoylphenyl)-3-methyl-piperazine-1-carboxamide | 6 | 1 | 1.43 | 413.2 |
| 101 | (S)-[4-(5-Aminothiazolo[5,4-d]pyrimidin-7-yl)-3-methylpiperazin-1-yl](imidazo[1,2-a]-pyridin-2-yl)methanone | 1 | 1 | 1.53 | 395.1 |
| 102 | (S)-[4-(5-Aminothiazolo[5,4-d]pyrimidin-7-yl)-3-methylpiperazin-1-yl](6-methoxy-pyridin-3-yl)methanone | 1 | 1 | 1.61 | 386.1 |
| 103 | (S)-[4-(5-Aminothiazolo[5,4-d]pyrimidin-7-yl)-3-methylpiperazin-1-yl](pyridin-3-yl)-methanone | 1 | 1 | 1.3 | 356.1 |
| 104 | (S)-[4-(5-Aminothiazolo[5,4-d]pyrimidin-7-yl)-3-methylpiperazin-1-yl](5-methyl-1H-pyrazol-3-yl)methanone | 1 | 1 | 1.40 | 359.1 |
| 105 | (S)-1-[4-(5-Aminothiazolo[5,4-d]pyrimidin-7-yl)-3-methylpiperazin-1-yl]-2-(pyridm-4-yl)ethanone | 1 | 1 | 1.35 | 370.1 |
| 106 | (S)-1-[4-(5-Aminothiazolo[5,4-d]pyrimidin-7-yl)-3-methylpiperazin-1-yl]-2-(pyridin-3-yl)ethanone | 1 | 1 | 1.46 | 370.1 |
| 107 | (S)-1-[4-(5-Aminothiazolo[5,4-d]pyrimidin-7-yl)-3-methylpiperazin-1-yl]-2-(4-(dimethylamino)phenyl)ethanone | 1 | 1 | 1.96 | 412.1 |
| 108 | (S)-4-(5-Aminothiazolo[5,4-d]pyrimidin-7-yl)-N-benzyl-3-methylpiperazine-1-carboxamide | 6 | 1 | 1.84 | 384.2 |
| 109 | (S)-4-(5-Aminothiazolo[5,4-d]pyrimidin-7-yl)-3-methyl-N-(4-methylbenzyl)-piperazine-1-carboxamide | 6 | 1 | 1.96 | 398.2 |
| 110 | (S)-4-(5-Aminothiazolo[5,4-d]pyrimidin-7-yl)-N-(benzo[d][1,3]dioxol-5-ylmethyl)-3-methylpiperazine-1-carboxamide | 6 | 1 | 1.77 | 428.2 |
| 111 | (S)-4-(5-Aminothiazolo[5,4-d]pyrimidin-7-yl)-N-[(2,3-dihydrobenzofuran-5-yl)-methyl]-3-methylpiperazine-1-carboxamide | 6 | 1 | 1.78 | 426.2 |
| 112 | (S)-N-[(1H-Indol-5-yl)methyl]-4-(5-aminothiazolo[5,4-d]pyrimidin-7-yl)-3-methyl-piperazine-1-carboxamide | 6 | 1 | 1.83 | 423.2 |
| 113 | (S)-4-(5-Aminothiazolo[5,4-d]pyrimidin-7-yl)-N-[4-(dimethylamino)benzyl]-3-methyl-piperazine-1-carboxamide | 6 | 1 | 1.82 | 427.2 |

-continued

| Ex. | Name | Expt. Procedure | LCMS Data Method | RT | [M + H]+ |
|---|---|---|---|---|---|
| 114 | (S)-4-(5-Aminothiazolo[5,4-d]pyrimidin-7-yl)-3-methyl-N-(thiazol-2-ylmethyl)-piperazine-1-carboxamide | 6 | 1 | 1.54 | 391.1 |
| 115 | (S)-4-(5-Aminothiazolo[5,4-d]pyrimidin-7-yl)-3-methyl-N-[(4-methylthiazol-2-yl)-methyl]piperazine-1-carboxamide | 6 | 1 | 1.59 | 405.2 |
| 116 | (S)-4-(5-Aminothiazolo[5,4-d]pyrimidin-7-yl)-N-(4-cyanobenzyl)-3-methylpiperazine-1-carboxamide | 6 | 1 | 1.68 | 409.2 |
| 117 | (S)-4-(5-Aminothiazolo[5,4-d]pyrimidin-7-yl)-N-(3,4-dimethoxybenzyl)-3-methyl-piperazine-1-carboxamide | 6 | 1 | 1.69 | 444.2 |
| 118 | (S)-4-(5-Aminothiazolo[5,4-d]pyrimidin-7-yl)-N-(imidazo[2,1-b]thiazol-5-ylmethyl)-3-methylpiperazine-1-carboxamide | 5 | 1 | 1.56 | 430.2 |
| 119 | (S)-1-[4-(5-Aminothiazolo[5,4-d]pyrimidin-7-yl)-3-methylpiperazin-1-yl]-2-phenoxy-ethanone | 1 | 1 | 1.88 | 385.1 |
| 120 | (S)-1-[4-(5-Aminothiazolo[5,4-d]pyrimidin-7-yl)-3-methylpiperazin-1-yl]-2-(4-methoxyphenoxy)ethanone | 1 | 1 | 1.86 | 415.2 |
| 121 | (S)-7-[2-Methyl-4-(pyridin-3-ylmethyl)-piperazin-1-yl]thiazolo[5,4-d]pyrimidin-5-amine | 3 | 1 | 1.79 | 342.1 |
| 122 | (S)-7-[2-Methyl-4-(pyridin-2-ylmethyl)-piperazin-1-yl]thiazolo[5,4-d]pyrimidin-5-amine | 3 | 1 | 1.82 | 342.1 |
| 123 | (S)-3-[4-(5-Aminothiazolo[5,4-d]pyrimidin-7-yl)-3-methylpiperazin-1-yl]-4-(phenyl-amino)cyclobut-3-ene-1,2-dione | 4 | 1 | 1.73 | 422.1 |
| 124 | (S)-3-[4-(5-Aminothiazolo[5,4-d]pyrimidin-7-yl)-3-methylpiperazin-1-yl]-4-(cyclo-propylamino)cyclobut-3-ene-1,2-dione | 4 | 1 | 1.40 | 386.2 |
| 125 | (S)-4-(5-Aminothiazolo[5,4-d]pyrimidin-7-yl)-N-[4-(difluoromethoxy)-2-methyl-phenyl]-3-methylpiperazine-1-carboxamide | 6 | 1 | 2.02 | 450.2 |
| 126 | (3S)-4-(5-Aminothiazolo[5,4-d]pyrimidin-7-yl)-3-methyl-N-{2-methyl-4-[(tetrahydro-furan-3-yl)methoxy]phenyl}piperazine-1-carboxamide | 6 | 1 | 1.90 | 484.3 |
| 127 | (S)-4-(5-Aminothiazolo[5,4-d]pyrimidin-7-yl)-3-methyl-N-{2-methyl-4-[2-(morpholin-4-yl)ethoxy]phenyl}piperazine-1-carboxamide | 6 | 1 | 1.81 | 513.3 |
| 128 | (S)-4-(5-Aminothiazolo[5,4-d]pyrimidin-7-yl)-N-[4-methoxy-2-(trifluoromethyl)-phenyl]-3-methylpiperazine-1-carboxamide | 6 | 1 | 2.01 | 468.2 |
| 129 | (S)-4-(5-Aminothiazolo[5,4-d]pyrimidin-7-yl)-N-(2-chloro-4-methoxyphenyl)-3-methylpiperazine-1-carboxamide | 6 | 1 | 1.99 | 434.1 |
| 130 | (S)-4-(5-Aminothiazolo[5,4-d]pyrimidin-7-yl)-N-(2-cyano-4-methoxyphenyl)-3-methylpiperazine-1-carboxamide | 6 | 1 | 1.69 | 425.2 |
| 131 | (S)-4-(5-Aminothiazolo[5,4-d]pyrimidin-7-yl)-N-(6-methoxy-2-methylpyridin-3-yl)-3-methylpiperazine-1-carboxamide | 6 | 1 | 1.62 | 415.2 |
| 132 | (S)-4-(5-Aminothiazolo[5,4-d]pyrimidin-7-yl)-N-(6-methoxy-4-methylpyridin-3-yl)-3-methylpiperazine-1-carboxamide | 6 | 1 | 1.65 | 415.2 |
| 133 | (S)-4-(5-Aminothiazolo[5,4-d]pyrimidin-7-yl)-N-(2-chloro-6-methoxypyridin-3-yl)-3-methylpiperazine-1-carboxamide | 6 | 1 | 1.84 | 435.1 |
| 134 | (S)-4-(5-Aminothiazolo[5,4-d]pyrimidin-7-yl)-N-(2,6-dimethoxypyridin-3-yl)-3-methylpiperazine-1-carboxamide | 6 | 1 | 1.92 | 431.2 |
| 135 | (S)-4-(5-Aminothiazolo[5,4-d]pyrimidin-7-yl)-N-(1,3-dimethyl-1H-pyrazol-4-yl)-3-methylpiperazine-1-carboxamide | 6 | 1 | 1.40 | 388.2 |
| 136 | (S)-4-(5-Aminothiazolo[5,4-d]pyrimidin-7-yl)-N-(1,5-dimethyl-1H-pyrazol-4-yl)-3-methylpiperazine-1-carboxamide | 6 | 1 | 1.41 | 388.3 |
| 137 | (S)-4-(5-Aminothiazolo[5,4-d]pyrimidin-7-yl)-3-methyl-N-[5-(4-methylpiperazin-1-yl)pyridin-2-yl]piperazine-1-carboxamide | 6 | 1 | 1.53 | 469.3 |

| Ex. | Name | Expt. Procedure | LCMS Data Method | RT | [M + H]+ |
|---|---|---|---|---|---|
| 138 | (S)-4-(5-Aminothiazolo[5,4-d]pyrimidin-7-yl)-3-methyl-N-[6-(4-methylpiperazin-1-yl)pyridin-3-yl]piperazine-1-carboxamide | 6 | 1 | 1.55 | 469.2 |
| 139 | (S)-4-(5-Aminothiazolo[5,4-d]pyrimidin-7-yl)-N-(5-methoxy-3-methylpyrazin-2-yl)-3-methylpiperazine-1-carboxamide | 6 | 1 | 1.53 | 416.2 |
| 140 | (S)-4-(5-Aminothiazolo[5,4-d]pyrimidin-7-yl)-N-(5-methoxypyrazin-2-yl)-3-methyl-piperazine-1-carboxamide | 6 | 1 | 1.61 | 402.0 |
| 141 | (S)-4-(5-Aminotiazolo[5,4-d]pyrimidin-7-yl)-N-(2-methoxy-4-methylpyrimidin-5-yl)-3-methylpiperazine-1-carboxamide | 6 | 1 | 1.46 | 416.2 |
| 142 | (S)-4-(5-Aminothiazolo[5,4-d]pyrimidin-7-yl)-N-(2-methoxypyrimidin-5-yl)-3-methyl-piperazine-1-carboxamide | 6 | 1 | 1.44 | 402.0 |
| 143 | (S)-4-(5-Aminothiazolo[5,4-d]pyrimidin-7-yl)-N-(6-methoxypyridazin-3-yl)-3-methyl-piperazine-1-carboxamide | 6 | 1 | 1.55 | 402.0 |
| 144 | (S)-4-(5-Aminothiazolo[5,4-d]pyrimidin-7-yl)-N-{4-[(dimethylamino)methyl]-2-methylphenyl}-3-methylpiperazine-1-carboxamide | 6 | 1 | 1..89 | 441.3 |
| 145 | (S)-4-(5-Aminothiazolo[5,4-d]pyrimidin-7-yl)-3-methyl-N-[2-methyl-4-(pyrrolidin-1-ylmethyl)phenyl]piperazine-1-carboxamide | 6 | 1 | 2.00 | 467.3 |
| 146 | (S)-4-(5-Aminothiazolo[5,4-d]pyrimidin-7-yl)-3-methyl-N-{2-methyl-4-[(4-methyl-piperazin-1-yl)methyl]phenyl}piperazine-1-carboxamide | 6 | 1 | 1.64 | 496.4 |
| 147 | (S)-4-(5-Aminothiazolo[5,4-d]pyrimidin-7-yl)-3-methyl-N-[2-methyl-4-(morpholin-4-ylmethyl)phenyl]piperazine-1-carboxamide | 6 | 1 | 1.67 | 483.3 |
| 148 | (S)-4-(5-Aminothiazolo[5,4-d]pyrimidin-7-yl)-3-methyl-N-[2-methyl-6-(pyrrolidin-1-ylmethyl)pyridin-3-yl]piperazine-1-carboxamide | 6 | 1 | 1.63 | 468.3 |
| 149 | (S)-4-(5-Aminothiazolo[5,4-d]pyrimidin-7-yl)-3-methyl-N-{2-methyl-6-[(4-methyl-piperazin-1-yl)methyl]pyridin-3-yl}-piperazine-1-carboxamide | 6 | 1 | 1.42 | 497.3 |
| 150 | (S)-4-(5-Aminothiazolo[5,4-d]pyrimidin-7-yl)-3-methyl-N-[2-methyl-6-(morpholin-4-ylmethyl)pyridin-3-yl]piperazine-1-carboxamide | 6 | 1 | 1.45 | 484.3 |
| 151 | (S)-4-(5-Aminothiazolo[5,4-d]pyrimidin-7-yl)-N-[6-(dimethylamino)-2-methylpyridin-3-yl]-3-methylpiperazine-1-carboxamide | 6 | 1 | 1.65 | 428.2 |
| 152 | (S)-4-(5-Aminothiazolo[5,4-d]pyrimidin-7-yl)-N-[6-(azetidin-1-yl)-2-methylpyridin-3-yl]-3-methylpiperazine-1-carboxamide | 6 | 1 | 1.67 | 440.3 |
| 153 | (S)-4-(5-Aminothiazolo[5,4-d]pyrimidin-7-yl)-3-methyl-N-[2-methyl-6-(pyrrolidin-1-yl)pyridin-3-yl]piperazine-1-carboxamide | 6 | 1 | 1.82 | 454.3 |
| 154 | (S)-4-(5-Aminothiazolo[5,4-d]pyrimidin-7-yl)-N-[6-(3-fluoroazetidin-1-yl)-2-methyl-pyridin-3-yl]-3-methylpiperazine-1-carboxamide | 6 | 1 | 1.63 | 458.3 |
| 155 | (S)-4-(5-Aminothiazolo[5,4-d]pyrimidin-7-yl)-N-[6-(3,3-difluoroazetidin-1-yl)-2-methylpyridin-3-yl]-3-methylpiperazine-1-carboxamide | 6 | 1 | 1.82 | 476.1 |
| 156 | (S)-4-(5-Aminothiazolo[5,4-d]pyrimidin-7-yl)-N-[6-(3,3-difluoropyrrolidin-1-yl)-2-methylpyridin-3-yl]-3-methylpiperazine-1-carboxamide | 6 | 1 | 1.97 | 490.3 |
| 157 | (S)-4-(5-Aminothiazolo[5,4-d]pyrimidin-7-yl)-N-[6-(3,3-difluoropiperidin-1-yl)-2-methylpyridin-3-yl]-3-methylpiperazine-1-carboxamide | 6 | 1 | 2.08 | 504.3 |
| 158 | (S)-4-(5-Aminothiazolo[5,4-d]pyrimidin-7-yl)-N-[6-(3-fluoropyrrolidin-1-yl)-2-methylpyridin-3-yl]-3-methylpiperazine-1-carboxamide | 6 | 1 | 1.78 | 472.2 |

-continued

| Ex. | Name | Expt. Procedure | LCMS Data Method | RT | [M + H]+ |
|---|---|---|---|---|---|
| 159 | (S)-4-(5-Aminothiazolo[5,4-d]pyrimidin-7-yl)-N-[4-(3-fluoropyrrolidin-1-yl)-2-methylphenyl]-3-methylpiperazine-1-carboxamide | 6 | 1 | 1.98 | 471.3 |
| 160 | (S)-4-(5-Aminothiazolo[5,4-d]pyrimidin-7-yl)-N-[6-(difluoromethoxy)-2-methyl-pyridin-3-yl]-3-methylpiperazine-1-carboxamide | 6 | 1 | 1.99 | 451.2 |
| 161 | (S)-4-(5-Aminothiazolo[5,4-d]pyrimidin-7-yl)-3-methyl-N-[2-methyl-6-(tetrahydro-furan-3-yloxy)pyridin-3-yl]piperazine-1-carboxamide | 6 | 1 | 1.62 | 471.3 |
| 162 | (S)-4-(5-Aminothiazolo[5,4-d]pyrimidin-7-yl)-N-[6-methoxy-2-(trifluoromethyl)-pyridin-3-yl]-3-methylpiperazine-1-carboxamide | 6 | 1 | 2.04 | 469.4 |
| 163 | (S)-4-(5-Aminothiazolo[5,4-d]pyrimidin-7-yl)-N-(2,6-dimethylpyridin-3-yl)-3-methyl-piperazine-1-carboxamide | 6 | 1 | 1.47 | 399.3 |
| 164 | (S)-4-(5-Aminothiazolo[5,4-d]pyrimidin-7-yl)-3-methyl-N-[6-methyl-2-(trifluoro-methyl)pyridin-3-yl]piperazine-1-carboxamide | 6 | 1 | 1.79 | 453.3 |
| 165 | (S)-4-(5-Aminothiazolo[5,4-d]pyrimidin-7-yl)-N-[2-(dimethylamino)-6-methylpyridin-3-yl]-3-methylpiperazine-1-carboxamide | 6 | 1 | 1.81 | 428.3 |
| 166 | (S)-4-(5-Aminothiazolo[5,4-d]pyrimidin-7-yl)-3-methyl-N-phenylpiperazine-1-carboxamide | 6 | 1 | 1.82 | 370.1 |
| 167 | (S)-4-(5-Aminothiazolo[5,4-d]pyrimidin-7-yl)-3-methyl-N-(m-tolyl)piperazine-1-carboxamide | 6 | 1 | 1.99 | 384.2 |
| 168 | (S)-4-(5-Aminothiazolo[5,4-d]pyrimidin-7-yl)-N-(3-methoxyphenyl)-3-methyl-piperazine-1-carboxamide | 6 | 1 | 1.87 | 400.2 |
| 169 | (S)-4-(5-Aminothiazolo[5,4-d]pyrimidin-7-yl)-N-(2-methoxyphenyl)-3-methyl-piperazine-1-carboxamide | 6 | 1 | 1.93 | 400.2 |
| 170 | (S)-4-(5-Aminothiazolo[5,4-d]pyrimidin-7-yl)-N-(2-chloro-4-methylphenyl)-3-methyl-piperazine-1-carboxamide | 6 | 1 | 2.17 | 418.1 |
| 171 | (S)-4-(5-Aminothiazolo[5,4-d]pyrimidin-7-yl)-3-methyl-N-(p-tolyl)piperazine-1-carboxamide | 6 | 1 | 2.00 | 384.1 |
| 172 | (S)-4-(5-Aminothiazolo[5,4-d]pyrimidin-7-yl)-3-methyl-N-[4-methyl-2-(trifluoro-methyl)phenyl]piperazine-1-carboxamide | 6 | 1 | 2.16 | 452.2 |
| 173 | (S)-4-(5-Aminothiazolo[5,4-d]pyrimidin-7-yl)-N-[2,4-bis(trifluoromethyl)phenyl]-3-methylpiperazine-1-carboxamide | 6 | 1 | 2.55 | 506.2 |
| 174 | (S)-4-(5-Aminothiazolo[5,4-d]pyrimidin-7-yl)-N-(6-chloropyridin-3-yl)-3-methyl-piperazine-1-carboxamide | 5 | 2 | 1.59 | 405.6 |
| 175 | (S)-4-(5-Aminothiazolo[5,4-d]pyrimidin-7-yl)-3-methyl-N-[4-methyl-6-(4-methyl-piperazin-1-yl)pyridin-3-yl]piperazine-1-carboxamide | 5 | 2 | 1.47 | 483.8 |
| 176 | (S)-4-(5-Aminothiazolo[5,4-d]pyrimidin-7-yl)-3-methyl-N-[2-methyl-4-(oxetan-3-yl-oxy)phenyl]piperazine-1-carboxamide | 5 | 2 | 1.59 | 456.8 |
| 177 | tert-Butyl 3-(4-{[(3S)-4-(5-aminothiazolo-[5,4-d]pyrimidin-7-yl)-3-methylpiperazine-1-carbonyl]amino}-3-methylphenoxy)-azetidine-1-carboxylate | 5 | 2 | 2.25 | 555.8 |
| 178 | (S)-4-(5-Aminothiazolo[5,4-d]pyrimidin-7-yl)-N-[4-(azetidin-3-yloxy)-2-methyl-phenyl]-3-methylpiperazine-1-carboxamide | 10 | 2 | 1.31 | 455.8 |
| 179 | tert-Butyl 4-(5-{[(3S)-4-(5-aminothiazolo-[5,4-d]pyrimidin-7-yl)-3-methylpiperazine-1-carbonyl]amino}-4-methylpyridin-2-yl)-piperazine-1-carboxylate | 5 | 2 | 1.98 | 569.8 |
| 180 | (S)-4-(5-Aminothiazolo[5,4-d]pyrimidin-7-yl)-3-methyl-N-[4-methyl-6-(piperazin-1-yl)pyridin-3-yl]piperazine-1-carboxamide | 10 | 2 | 1.32 | 469.8 |

-continued

| Ex. | Name | Expt. Procedure | LCMS Data Method | RT | [M + H]+ |
|---|---|---|---|---|---|
| 181 | tert-Butyl 3-[(5-{[(3S)-4-(5-aminothiazolo-[5,4-d]pyrimidin-7-yl)-3-methylpiperazine-1-carbonyl]amino}-4-methylpyridin-2-yl)-oxy]azetidine-1-carboxylate | 5 | 2 | 2.11 | 556.8 |
| 182 | (S)-4-(5-Aminothiazolo[5,4-d]pyrimidin-7-yl)-N-(indan-5-yl)-3-methylpiperazine-1-carboxamide | 5 | 2 | 2.05 | 410.8 |
| 183 | tert-Butyl 3-[(5-{[(3S)-4-(5-aminothiazolo-[5,4-d]pyrimidin-7-yl)-3-methylpiperazine-1-carbonyl]amino}-4-methylpyridin-2-yl)-oxy]pyrrolidine-1-carboxylate | 5 | 2 | 2.13 | 470.8 |
| 184 | (S)-4-(5-Aminothiazolo[5,4-d]pyrimidin-7-yl)-3-methyl-N-[4-methyl-6-(pyrrolidin-3-yloxy)pyridin-3-yl]piperazine-1-carboxamide | 10 | 2 | 1.38 | 470.6 |

Examples 185 to 188

The following compounds were synthesised from Intermediate 6 and commercial reagents in accordance with the specified procedure.

Example 185

(3S)-4-(5-Aminothiazolo[5,4-d]pyrimidin-7-yl)-N-(4-methoxy-2-methylphenyl)-3-methylpiperazine-1-carboxamide Procedure 7. $\delta_H$ (DMSO-d$_6$) 8.69 (s, 1H), 7.97 (s, 1H), 7.04 (d, J=8.6 Hz, 1H), 6.77 (d, J=2.7 Hz, 1H), 6.71 (dd, J 2.9, 8.6 Hz, 1H), 6.35 (s, 2H), 5.50 (br s, 1H), 5.20 (br s, 1H), 4.12 (d, J=12.8 Hz, 1H), 3.98 (d, J=13.7 Hz, 1H), 3.71 (s, 3H), 3.20-3.50 (m, 3H), 3.12-2.90 (m, 1H), 2.14 (s, 3H), 1.22 (d, J=6.6 Hz, 3H). LCMS (ES+) 414.8 (M+H)+, RT 1.609 minutes (method 2).

Example 186

(3S)-4-(5-Aminothiazolo[5,4-d]pyrimidin-7-yl)-N-[4-(difluoromethoxy)-phenyl]-3-methylpiperazine-1-carboxamide Procedure 7. $\delta_H$ (DMSO-d$_6$) 8.70 (s, 1H), 8.61 (s, 1H), 7.51 (d, J=9 Hz, 2H), 7.09 (t, J=79.6 Hz, 1H), 7.08 (d, J=14 Hz, 2H), 6.36 (s, 2H), 5.60 (br s, 1H), 5.15 (br s, 1H), 4.15 (d, J=13.5 Hz, 1H), 4.01 (d, J=13.1 Hz, 1H), 3.49-3.22 (m, 2H), 3.22-3.01 (m, 1H), 1.22 (d, J=6.6 Hz, 3H). LCMS (ES+) 436.8 (M+H)+, RT 1.869 minutes (method 2).

Example 187

(3S)-4-(5-Aminothiazolo[5,4-d]pyrimidin-7-yl)-N-(4-methoxyphenyl)-3-methylpiperazine-1-carboxamide Procedure 7. $\delta_H$ (DMSO-d$_6$) 8.70 (s, 1H), 8.38 (s, 1H), 7.35 (d, J=9 Hz, 2H), 6.83 (d, J=9 Hz, 2H), 6.36 (s, 2H), 5.57 (br s, 1H), 5.22 (br s, 1H), 4.12 (d, J=12.9 Hz, 1H), 3.98 (d, J=13.3 Hz, 1H), 3.71 (s, 3H), 3.61-3.29 (m, 3H), 1.23 (d, J=6.6 Hz, 3H). LCMS (ES+) 400.8 (M+H)+, RT 1.594 minutes (method 2).

Example 188

(3S)-4-(5-Aminothiazolo[5,4-d]pyrimidin-7-yl)-N-(2,3-dihydrobenzofuran-5-yl)-3-methylpiperazine-1-carboxamide Procedure 7. $\delta_H$ (DMSO-d$_6$) 8.78 (s, 1H), 8.32 (s, 1H), 7.32 (s, 1H), 7.06 (d, J=9 Hz, 1H), 6.80 (br s, 2H), 6.64 (d, J=8.5 Hz, 1H), 5.57 (br s, 1H), 5.22 (br s, 1H), 4.50 (t, J=8.7 Hz, 2H), 4.12 (d, J=13.3 Hz, 1H), 3.99 (d, J=13.3 Hz, 1H), 3.52-3.39 (m, 1H), 3.27 (dd, J 3.8, 13.5 Hz, 1H), 3.17-3.01 (m, 3H), 1.25 (d, J=6.6 Hz, 3H). LCMS (ES+) 412.8 (M+H)+, RT 1.581 minutes (method 2).

Examples 189 & 190

The following compounds were synthesised from Intermediate 103 and commercial reagents in accordance with the specified procedure.

| Ex. | Name | Expt. Procedure | LCMS Data Method | RT | [M + H]+ |
|---|---|---|---|---|---|
| 189 | 1-[5-(5-Aminothiazolo[5,4-d]pyrimidin-7-yl)-2,5-diazabicyclo[2.2.1]heptan-2-yl]-2-(4-methoxyphenoxy)ethanone | 1 | 1 | 1.82 | 413.3 |
| 190 | 5-(5-Aminothiazolo[5,4-d]pyrimidin-7-yl)-N-(4-methoxyphenyl)-2,5-diazabicyclo[2.2.1]heptane-2-carboxamide | 2 | 1 | 1.75 | 398.3 |

Examples 191 to 196

The following compounds were synthesised from Intermediate 104 and commercial reagents in accordance with the specified procedure.

|     |      | Expt. | | LCMS Data | |
| --- | --- | --- | --- | --- | --- |
| Ex. | Name | Procedure | Method | RT | [M + H]⁺ |
| 191 | 1-[4-(5-Aminothiazolo[5,4-d]pyrimidin-7-yl)-3-(hydroxymethyl)piperazin-1-yl]-2-(4-methoxyphenoxy)ethanone | 1 | 1 | 1.97 | 431.3 |
| 192 | 1-[4-(5-Aminothiazolo[5,4-d]pyrimidin-7-yl)-3-(hydroxymethyl)piperazin-1-yl]-2-(3-methoxyphenoxy)ethanone | 1 | 1 | 2.00 | 431.3 |
| 193 | 1-[4-(5-Aminothiazolo[5,4-d]pyrimidin-7-yl)-3-(hydroxymethyl)piperazin-1-yl]-3-(4-methoxyphenyl)propan-1-one | 1 | 1 | 2.00 | 429.3 |
| 194 | 4-(5-Aminothiazolo[5,4-d]pyrimidin-7-yl)-3-(hydroxymethyl)-N-(4-methoxyphenyl)-piperazine-1-carboxamide | 2 | 1 | 1.69 | 416.1 |
| 195 | 4-(5-Aminothiazolo[5,4-d]pyrimidin-7-yl)-3-(hydroxymethyl)-N-(3-methoxyphenyl)-piperazine-1-carboxamide | 2 | 1 | 2.10 | 416.2 |
| 196 | 4-(5-Aminothiazolo[5,4-d]pyrimidin-7-yl)-3-(hydroxymethyl)-N-(p-tolyl)piperazine-1-carboxamide | 2 | 1 | 1.72 | 400.1 |

Examples 197 to 201

The following compounds were synthesised from Intermediate 105 and commercial reagents in accordance with the specified procedure.

|     |      | Expt. | | LCMS Data | |
| --- | --- | --- | --- | --- | --- |
| Ex. | Name | Procedure | Method | RT | [M + H]⁺ |
| 197 | 1-[4-(5-Aminothiazolo[5,4-d]pyrimidin-7-yl)-2-methylpiperazin-1-yl]-2-(4-methoxyphenoxy)ethanone | 1 | 1 | 1.96 | 415.3 |
| 198 | 1-[4-(5-Aminothiazolo[5,4-d]pyrimidin-7-yl)-2-methylpiperazin-1-yl]-2-(3-methoxyphenoxy)ethanone | 1 | 1 | 2.02 | 415.3 |
| 199 | 4-(5-Aminothiazolo[5,4-d]pyrimidin-7-yl)-N-(4-methoxyphenyl)-2-methylpiperazine-1-carboxamide | 2 | 1 | 1.94 | 399.47 |
| 200 | 4-(5-Aminothiazolo[5,4-d]pyrimidin-7-yl)-N-(3-methoxyphenyl)-2-methylpiperazine-1-carboxamide | 2 | 1 | 1.87 | 400.2 |
| 201 | 4-(5-Aminothiazolo[5,4-d]pyrimidin-7-yl)-2-methyl-N-(p-tolyl)piperazine-1-carboxamide | 2 | 1 | 2.11 | 384.2 |

Examples 202 to 206

The following compounds were synthesised from Intermediate 106 and commercial reagents in accordance with the specified procedure.

|     |      | Expt. | | LCMS Data | |
| --- | --- | --- | --- | --- | --- |
| Ex. | Name | Procedure | Method | RT | [M + H]⁺ |
| 202 | (R)-1-[4-(5-Aminothiazolo[5,4-d]-pyrimidin-7-yl)-2-(hydroxymethyl)-piperazin-1-yl]-2-(4-methoxyphenoxy)-ethanone | 1 | 1 | 1.88 | 431.3 |

|  |  | Expt. | LCMS Data | | |
|---|---|---|---|---|---|
| Ex. | Name | Procedure | Method | RT | [M + H]+ |
| 203 | (R)-1-[4-(5-Aminothiazolo[5,4-d]-pyrimidin-7-yl)-2-(hydroxymethyl)-piperazin-1-yl]-2-(3-methoxyphenoxy)-ethanone | 1 | 1 | 1.95 | 431.3 |
| 204 | (R)-4-(5-Aminothiazolo[5,4-d]pyrimidin-7-yl)-2-(hydroxymethyl)-N-(4-methoxy-phenyl)piperazine-1-carboxamide | 2 | 1 | 1.77 | 416.2 |
| 205 | (R)-4-(5-Aminothiazolo[5,4-d]pyrimidin-7-yl)-2-(hydroxymethyl)-N-(3-methoxy-phenyl)piperazine-1-carboxamide | 2 | 1 | 1.83 | 416.3 |
| 206 | (R)-4-(5-Aminothiazolo[5,4-d]pyrimidin-7-yl)-2-(hydroxymethyl)-N-(p-tolyl)-piperazine-1-carboxamide | 2 | 1 | 2.04 | 400.3 |

Examples 207 to 212

The following compounds were synthesised from Intermediate 107 and commercial reagents in accordance with the specified procedure.

|  |  | Expt. | LCMS Data | | |
|---|---|---|---|---|---|
| Ex. | Name | Procedure | Method | RT | [M + H]+ |
| 207 | (S)-1-[4-(5-Aminothiazolo[5,4-d]pyrimidin-7-yl)-2-(hydroxymethyl)piperazin-1-yl]-2-(4-methoxyphenoxy)ethanone | 1 | 1 | 1.83 | 431.2 |
| 208 | (S)-1-[4-(5-Aminothiazolo[5,4-d]pyrimidin-7-yl)-2-(hydroxymethyl)piperazin-1-yl]-2-(3-methoxyphenoxy)ethanone | 1 | 1 | 1.89 | 431.2 |
| 209 | (S)-1-[4-(5-Aminothiazolo[5,4-d]pyrimidin-7-yl)-2-(hydroxymethyl)piperazin-1-yl]-3-(4-methoxyphenyl)propan-1-one | 1 | 1 | 1.94 | 451.2 (M + 23 adduct) |
| 210 | (S)-4-(5-Aminothiazolo[5,4-d]pyrimidin-7-yl)-2-(hydroxymethyl)-N-(4-methoxy-phenyl)piperazine-1-carboxamide | 2 | 1 | 1.73 | 416.4 |
| 211 | (S)-4-(5-Aminothiazolo[5,4-d]pyrimidin-7-yl)-2-(hydroxymethyl)-N-(3-methoxy-phenyl)piperazine-1-carboxamide | 2 | 1 | 1.81 | 416.2 |
| 212 | (S)-4-(5-Aminothiazolo[5,4-d]pyrimidin-7-yl)-2-(hydroxymethyl)-N-(p-tolyl)-piperazine-1-carboxamide | 2 | 1 | 2.04 | 400.2 |

Examples 213 to 218

The following compounds were synthesised from Intermediate 108 and commercial reagents in accordance with the specified procedure.

|  |  | Expt. | LCMS Data | | |
|---|---|---|---|---|---|
| Ex. | Name | Procedure | Method | RT | [M + H]+ |
| 213 | 1-[4-(5-Aminothiazolo[5,4-d]pyrimidin-7-yl)-3-methylpiperazin-1-yl]-2-(4-methoxy-phenoxy) ethanone | 1 | 1 | 1.94 | 415.2 |
| 214 | 1-[4-(5-Aminothiazolo[5,4-d]pyrimidin-7-yl)-3-methylpiperazin-1-yl]-2-(3-methoxy-phenoxy)ethanone | 1 | 1 | 2.15 | 415.2 |
| 215 | 4-(5-Aminothiazolo[5,4-d]pyrimidin-7-yl)-N-(4-methoxyphenyl)-3-methylpiperazine-1-carboxamide | 2 | 1 | 1.97 | 400.1 |
| 216 | 4-(5-Aminothiazolo[5,4-d]pyrimidin-7-yl)-N-(3-methoxyphenyl)-3-methylpiperazine-1-carboxamide | 2 | 1 | 1.88 | 400.2 |
| 217 | 4-(5-Aminothiazolo[5,4-d]pyrimidin-7-yl)-3-methyl-N-(p-tolyl)piperazine-1-carboxamide | 2 | 1 | 2.17 | 384.1 |

| Ex. | Name | Expt. Procedure | LCMS Data Method | RT | [M + H]⁺ |
|---|---|---|---|---|---|
| 218 | 4-(5-Aminothiazolo[5,4-d]pyrimidin-7-yl)-N-(4-methoxy-2-methylphenyl)-3-methyl-piperazine-1-carboxamide | 2 | 1 | 1.82 | 414.1 |

Examples 219 to 223

The following compounds were synthesised from Intermediate 109 and commercial reagents in accordance with the specified procedure.

| Ex. | Name | Expt. Procedure | LCMS Data Method | RT | [M + H]⁺ |
|---|---|---|---|---|---|
| 219 | 1-[4-(5-Aminothiazolo[5,4-d]pyrimidin-7-yl)-2,3-dimethylpiperazin-1-yl]-2-(4-methoxyphenoxy)ethanone | 1 | 1 | 2.06 | 429.3 |
| 220 | 1-[4-(5-Aminothiazolo[5,4-d]pyrimidin-7-yl)-2,3-dimethylpiperazin-1-yl]-2-(3-methoxyphenoxy)ethanone | 1 | 1 | 2.10 | 429.3 |
| 221 | 4-(5-Aminothiazolo[5,4-d]pyrimidin-7-yl)-N-(4-methoxyphenyl)-2,3-dimethyl-piperazine-1-carboxamide | 2 | 1 | 1.94 | 414.2 |
| 222 | 4-(5-Aminothiazolo[5,4-d]pyrimidin-7-yl)-N-(3-methoxyphenyl)-2,3-dimethyl-piperazine-1-carboxamide | 2 | 1 | 2.02 | 414.3 |
| 223 | 4-(5-Aminothiazolo[5,4-d]pyrimidin-7-yl)-2,3-dimethyl-N-(p-tolyl)piperazine-1-carboxamide | 2 | 1 | 2.15 | 398.3 |

Examples 224 to 228

The following compounds were synthesised from Intermediate 110 and commercial reagents in accordance with the specified procedure.

| Ex. | Name | Expt. Procedure | LCMS Data Method | RT | [M + H]⁺ |
|---|---|---|---|---|---|
| 224 | 1-[(2R,5S)-4-(5-Aminothiazolo[5,4-d]-pyrimidin-7-yl)-2,5-dimethylpiperazin-1-yl]-2-(4-methoxyphenoxy)ethanone | 1 | 1 | 2.10 | 429.3 |
| 225 | 1-[(2R,5S)-4-(5-Aminothiazolo[5,4-d]-pyrimidin-7-yl)-2,5-dimethylpiperazin-1-yl]-2-(3-methoxyphenoxy)ethanone | 1 | 1 | 2.11 | 429.3 |
| 226 | (2R,5S)-4-(5-Aminothiazolo[5,4-d]-pyrimidin-7-yl)-N-(4-methoxyphenyl)-2,5-dimethylpiperazine-1-carboxamide | 2 | 1 | 1.95 | 414.2 |
| 227 | (2R,5S)-4-(5-Aminothiazolo[5,4-d]-pyrimidin-7-yl)-N-(3-methoxyphenyl)-2,5-dimethylpiperazine-1-carboxamide | 2 | 1 | 2.02 | 414.3 |
| 228 | (2R,5S)-4-(5-Aminothiazolo[5,4-d]-pyrimidin-7-yl)-2,5-dimethyl-N-(p-tolyl)-piperazine-1-carboxamide | 2 | 1 | 2.12 | 398.3 |

Example 229

(3S)-4-(5-Aminothiazolo[5,4-d]pyrimidin-7-yl)-3-ethyl-N-(4-methoxyphenyl)piperazine-1-carboxamide Intermediate 7 (0.2 g, 0.55 mmol) was dissolved/suspended in 4N HCl in 1,4-dioxane (5 mL), and methanol was added to aid solubility. The reaction mixture was stirred for 2 h, then concentrated in vacuo. The residue was dissolved in DMF (5 mL), then 4-methoxyphenyl isocyanate (0.083 g, 0.55 mmol) and DIPEA (0.14 g, 1.1 mmol) were added. The reaction mixture was stirred for a further 2 h at room temperature, then concentrated in vacuo. The residue was partitioned between EtOAc and water, then the organic layers were dried over sodium sulfate and concentrated in vacuo onto silica. Purification by column chromatography on silica gel with 100% EtOAc was followed by preparative HPLC, to yield the title compound (0.063 g, 27.7%) as a white solid. $\delta_H$ (DMSO-$d_6$) 8.69 (s, 1H), 8.39 (s, 1H), 7.34 (d, J=9 Hz, 2H), 6.83 (d, J=9 Hz, 2H), 6.36 (s, 2H), 5.30 (br s, 2H), 4.12 (d, J=13.2 Hz, 2H), 3.70 (s, 3H), 3.52-3.01 (m, 3H), 1.71-1.59 (m, 2H), 0.82 (t, J=13 Hz, 3H). LCMS (ES+) 414.5 (M+H)⁺, RT 1.77 minutes (method 2).

Example 230

(3S)-4-(5-Aminothiazolo[5,4-d]pyrimidin-7-yl)-3-isopropyl-N-(4-methoxyphenyl)-piperazine-1-carboxamide Prepared from Intermediate 8 (0.26 mmol) using Procedure 2. $\delta_H$ (DMSO-$d_6$) 8.69 (s, 1H), 8.40 (s, 1H), 7.33 (d, J=9 Hz, 2H), 6.83 (d, J=9 Hz, 2H), 6.36 (s, 2H), 5.75 (br s, 1H), 4.93 (br s, 1H), 4.33 (d, J=13.3 Hz, 1H), 4.16 (br s, 1H), 3.70 (s, 3H), 2.22-2.09 (m, 1H), 1.01 (d, 3H), 0.82 (t, J=6.6 Hz, 3H), 0.7 (br s, 3H). LCMS (ES+) 428.5 (M+H)$^+$, RT 1.92 minutes (method 2).

Example 231

(3S)-4-(5-Aminothiazolo[5,4-d]pyrimidin-7-yl)-3-cyclopropyl-N-(4-methoxyphenyl)-piperazine-1-carboxamide Intermediate 9 (0.18 g, 0.48 mmol) was stirred in TFA (2 mL, 25.8 mmol) for 4 h, then concentrated in vacuo and triturated with diethyl ether. The recovered solid was dissolved in DMF (5 mL) and DIPEA (0.13 g, 1.0 mmol), then 4-methoxyphenyl isocyanate (0.46 mmol) was added. The reaction was stirred for 48 h, then concentrated in vacuo. The residue was slurried in water. Collection by filtration provided the title compound (0.099 g, 50%) as a white solid. $\delta_H$ (DMSO-$d_6$) 8.75 (s, 1H), 8.46 (s, 1H), 7.34 (d, J=9 Hz, 2H), 6.83 (d, J=9 Hz, 2H), 6.81 (br s, 2H), 5.21 (br s, 2H), 4.23 (d, J=12.6 Hz, 2H), 3.70 (s, 3H), 3.61-2.98 (m, 3H), 1.49-1.21 (m, 1H), 0.61-0.51 (m, 1H), 0.49-0.28 (m, 3H). LCMS (ES+) 426.8 (M+H)$^+$, RT 1.81 minutes (method 2).

Example 232

(3S)-4-(5-Aminothiazolo[5,4-d]pyrimidin-7-yl)-3-isobutyl-N-(4-methoxyphenyl)-piperazine-1-carboxamide Intermediate 10 (0.2 g, 0.5 mmol) was dissolved/suspended in 4N HCl in 1,4-dioxane (5 mL) and stirred for 2 h. After this time, the reaction mixture was concentrated in vacuo and redissolved in DMF (5 mL) with DIPEA (2 eq) and 4-methoxyphenyl isocyanate (0.08 g, 0.55 mmol). The reaction mixture was stirred for 5 h, then concentrated in vacuo and partitioned between water and EtOAc. The organic layers were dried over sodium sulfate and concentrated onto silica. The resulting crude material was purified by column chromatography on silica gel with 100% EtOAc, then by preparative HPLC, to give the title compound (0.123 g, 50%) as white solid. $\delta_H$ (DMSO-$d_6$) 8.69 (s, 1H), 8.37 (s, 1H), 7.34 (d, J=9 Hz, 2H), 6.83 (d, J=9 Hz, 2H), 6.34 (s, 2H), 5.21 (br s, 2H), 4.21-4.01 (m, 2H), 3.70 (s, 3H), 3.31-2.89 (m, 3H), 1.61-1.42 (m, 3H), 0.95-0.75 (m, 6H). LCMS (ES+) 426.8 (M+H)$^+$, RT 1.81 minutes (method 2).

Example 233

4-(5-Aminothiazolo[5,4-d]pyrimidin-7-yl)-3-(2-hydroxyethyl)-N-(4-methoxyphenyl)-piperazine-1-carboxamide Prepared from Intermediate 11 using Procedure 2. $\delta_H$ (DMSO-$d_6$) 8.70 (s, 1H), 8.41 (s, 1H), 7.34 (d, J=9 Hz, 2H), 6.83 (d, J=9 Hz, 2H), 6.36 (s, 2H), 5.44 (br s, 2H), 4.56 (t, J=5.3 Hz, 1H), 4.17-4.05 (m, 2H), 3.70 (s, 3H), 3.51-3.31 (m, 3H), 3.19-3.11 (m, 1H), 3.07-2.91 (m, 1H), 1.91-1.72 (m, 2H). LCMS (ES+) 430.7 (M+H)$^+$, RT 1.16 minutes (method 2).

Example 234

9-(5-Aminothiazolo[5,4-d]pyrimidin-7-yl)-N-(4-methoxyphenyl)-6,9-diazaspiro[3.5]-nonane-6-carboxamide Prepared from Intermediate 15 using Procedure 2. $\delta_H$ (DMSO-$d_6$) 8.72 (s, 1H), 8.34 (s, 1H), 7.35-7.32 (m, 2H), 6.85-6.81 (m, 2H), 6.38 (s, 2H), 4.27 (s, 2H), 3.80 (s, 2H), 3.71 (s, 3H), 3.33 (m, 2H), 2.34-2.19 (m, 4H), 1.84-1.75 (m, 2H). LCMS (ES+) 426.3 (M+H)$^+$, RT 1.34 minutes (method 2).

Example 235

(3S,5R)-4-(5-Aminothiazolo[5,4-d]pyrimidin-7-yl)-N-(4-methoxyphenyl)-3,5-dimethylpiperazine-1-carboxamide Prepared from Intermediate 18 using Procedure 2. $\delta_H$ (DMSO-$d_6$) 8.69 (s, 1H), 8.41 (s, 1H), 7.39-7.33 (m, 2H), 6.87-6.82 (m, 2H), 6.35 (s, 2H), 5.48 (br s, 2H), 4.15 (d, J 13.3 Hz, 2H), 3.71 (s, 3H), 3.15 (dd, J 13.2, 4.2 Hz, 2H), 1.28 (d, J=6.8 Hz, 6H). LCMS (ES+) 414.8 (M+H)$^+$, RT 1.49 minutes (method 2).

Example 236

(3R)-4-(5-Aminothiazolo[5,4-d]pyrimidin-7-yl)-N-(4-methoxy-2-methylphenyl)-3-methylpiperazine-1-carboxamide Prepared from Intermediate 19 using Procedure 2. $\delta_H$ (DMSO-$d_6$) 8.70 (s, 1H), 7.97 (s, 1H), 7.04 (d, J=8.6 Hz, 1H), 6.77 (d, J=2.8 Hz, 1H), 6.70 (dd, J 2.9, 8.7 Hz, 1H), 6.35 (s, 2H), 5.50 (br s, 1H), 5.15 (br s, 1H), 4.13 (d, J=12.8 Hz, 1H), 3.98 (d, J=13.1 Hz, 1H), 3.71 (s, 3H), 3.20-3.50 (m, 2H), 3.12-3.01 (m, 1H), 2.14 (s, 3H), 1.22 (d, J=6.6 Hz, 3H). LCMS (ES+) 414.8 (M+H)$^+$, RT 1.63 minutes (method 2).

Example 237

(3R)-4-(5-Aminothiazolo[5,4-d]pyrimidin-7-yl)-N-(2,4-dimethylphenyl)-3-methylpiperazine-1-carboxamide Prepared from Intermediate 19 using Procedure 2. $\delta_H$ (DMSO-$d_6$) 8.70 (s, 1H), 7.99 (s, 1H), 7.04 (d, J=7.9 Hz, 1H), 7.00 (s, 1H), 6.94 (d, J=7.9 Hz, 1H), 6.36 (s, 2H), 5.59 (br s, 1H), 5.13 (br s, 1H), 4.12 (d, J=12.7 Hz, 1H), 3.99 (d, J=13.5 Hz, 1H), 3.50-3.20 (m, 2H), 3.15-3.01 (m, 1H), 2.25 (s, 3H), 2.14 (s, 3H), 1.26 (d, J=6.7 Hz, 3H). LCMS (ES+) 398.8 (M+H)$^+$, RT 1.82 minutes (method 2).

Example 238

Methyl 2-{1-(5-aminothiazolo[5,4-d]pyrimidin-7-yl)-4-[(2-methoxyphenyl)carbamoyl]-piperazin-2-yl}acetate Prepared from Intermediate 76 using Procedure 2. $\delta_H$ (DMSO-$d_6$) 8.71 (s, 1H), 7.73 (s, 1H), 7.65-7.63 (m, 1H), 7.05-7.00 (m, 2H), 6.90-6.86 (m, 1H), 6.38 (s, 2H), 5.85 (br s, 1H), 5.22 (br s, 1H), 4.13-4.06 (m, 2H), 3.82 (s, 3H), 3.48 (s, 3H), 3.31-3.28 (m, 2H), 3.14-3.07 (m, 1H), 2.84 (dd, J 15.7, 8.3 Hz, 1H), 2.69 (dd, J 15.7, 6.1 Hz, 1H). LCMS (ES+) 458.0 (M+H)+, RT 1.60 minutes (method 2).

Example 239

2-{1-(5-Aminothiazolo[5,4-d]pyrimidin-7-yl)-4-[(2-methoxyphenyl)carbamoyl]-piperazin-2-yl}acetic acid Prepared from Intermediate 76 using Procedure 2. $\delta_H$ (DMSO-$d_6$) 12.10 (s, 1H), 8.70 (s, 1H), 7.72 (s, 1H), 7.66 (d, J=7.6 Hz, 1H), 7.04-6.99 (m, 2H), 6.90-6.86 (m, 1H), 6.37 (s, 2H), 5.79 (br s, 1H), 5.32 (br s, 1H), 4.17-4.14 (m, 1H), 4.09-4.06 (m, 1H), 3.82 (s, 3H), 3.47 (m, 1H), 3.32-3.28 (m, 1H), 3.13-3.06 (m, 1H), 2.81 (dd, J 16.1, 9.3 Hz, 1H), 2.55-2.51 (m, 1H). LCMS (ES+) 444.0 (M+H)+, RT 1.36 minutes (method 2).

Example 240

Methyl 2-{1-(5-Aminothiazolo[5,4-d]pyrimidin-7-yl)-4-[(4-methoxyphenyl)carbamoyl]-piperazin-2-yl}acetate Intermediate 75 (0.2 g, 0.49 mmol) was stirred with 4N HCl in 1,4-dioxane (5 mL) for 2 h. The reaction mixture was concentrated in vacuo and dissolved in DMF (5 mL), then DIPEA (0.98 mmol) and 4-methoxyphenyl isocyanate (0.074 g, 0.49 mmol) were added. The reaction mixture was stirred at room temperature for three days, then concentrated in vacuo and partitioned between EtOAc and water. The organic layers were dried over sodium sulfate and concentrated onto silica. The residue was purified by column chromatography on silica gel, with a gradient of 1% increasing to 20% MeOH in EtOAc, to yield the title compound (0.013 g, 5.8%) as a white solid. $\delta_H$ (DMSO-$d_6$) 8.70 (s, 1H), 8.42 (s, 1H), 7.66 (d, J=9.1 Hz, 2H), 6.83 (d, J=9.1 Hz, 2H), 6.39 (s, 2H), 5.75 (br s, 1H), 5.22 (br s, 1H), 4.17-4.14 (m, 2H), 3.70 (s, 3H), 3.44 (s, 3H), 3.35-2.99 (m, 3H), 2.81-2.60 (m, 2H). LCMS (ES+) 458 (M+H)+, RT 1.64 minutes (method 2).

Example 241

3-(2-Amino-2-oxoethyl)-4-(5-aminothiazolo[5,4-d]pyrimidin-7-yl)-N-(2-methoxyphenyl)-piperazine-1-carboxamide EDC (0.024 g, 0.12 mmol) was added to a solution of Example 239 (0.05 g, 0.11 mmol), ammonium chloride (0.03 g, 0.56 mmol), HOBT (0.019 g, 0.12 mmol) and DIPEA (0.20 mL, 1.13 mmol) in DMF (3 mL). The reaction mixture was stirred for 20 h and then concentrated in vacuo. The residue was partitioned between EtOAc (10 mL) and water (10 mL), then separated. The organic phase was washed with brine (10 mL), dried over MgSO$_4$ and evaporated. The residue was purified by column chromatography on silica gel, with a gradient of 2% increasing to 10% MeOH in EtOAc over 20 column volumes. After purification by preparative HPLC, and freeze-drying from acetonitrile/water, the title compound (0.005 g, 10%) was obtained as a white powder. $\delta_H$ (DMSO-$d_6$) 8.68 (s, 1H), 7.85 (s, 1H), 7.70-7.68 (m, 1H), 7.37 (s, 1H), 7.03-6.98 (m, 2H), 6.91 (s, 1H), 6.90-6.85 (m, 1H), 6.38 (s, 2H), 5.60 (br s, 2H), 4.20 (d, J=12.7 Hz, 1H), 4.12 (d, J=12.7 Hz, 1H), 3.81 (s, 3H), 3.30-3.25 (m, 1H), 3.05-2.98 (m, 1H), 2.67 (dd, J 14.4, 9.5 Hz, 1H), 2.50 (m, 1H), 2.40 (dd, J 14.4, 4.4 Hz, 1H). LCMS (ES+) 443.0 (M+H)+, RT 1.56 minutes (method 2).

Example 242

4-(5-Aminothiazolo[5,4-d]pyrimidin-7-yl)-3-[2-(dimethylamino)-2-oxoethyl]-N-(2-methoxyphenyl) piperazine-1-carboxamide Prepared from dimethylamine hydrochloride following the method used to prepare Example 241. $\delta_H$ (DMSO-$d_6$) 8.71 (s, 1H), 7.86 (s, 1H), 7.71 (d, J=7.8 Hz, 1H), 7.03-6.97 (m, 2H), 6.91-6.84 (m, 1H), 6.34 (s, 2H), 5.61 (br s, 2H), 4.16-4.10 (m, 1H), 3.82 (s, 3H), 3.34 (m, 2H), 3.30-3.25 (m, 1H), 3.07-3.03 (m, 1H), 2.99 (s, 3H), 2.90 (dd, J 15.1, 10.2 Hz, 1H), 2.77 (s, 3H), 2.57-2.52 (m, 1H). LCMS (ES+) 471.2 (M+H)+, RT 1.75 minutes (method 2).

Example 243

(1S,5R)-3-(5-Aminothiazolo[5,4-d]pyrimidin-7-yl)-N-(4-methoxyphenyl)-3,8-diazabicyclo[3.2.1]octane-8-carboxamide To a solution of Intermediate 4 (0.5 g, 2.68 mmol) in 1,4-dioxane (10 mL) were added tert-butyl (1S,5R)-3,8-diazabicyclo[3.2.1]octane-8-carboxylate (2.14 mmol) and DIPEA (0.86 mL). The reaction mixture was heated at 100° C. for 8 h. The reaction mixture was filtered hot, and the solid was discarded. The filtrate was concentrated in vacuo, and partitioned between DCM and water. The organic layers were dried and further concentrated in vacuo. The resulting material was taken up in DCM (2 mL) and TFA (2 mL) and stirred at room temperature overnight. The reaction mixture was concentrated in vacuo and triturated with ether. The resulting solid was dissolved in DMF (5 mL), then DIPEA (0.198 g) and 4-methoxyphenyl isocyanate (0.091 g) were added. The reaction mixture was stirred at room temperature for 48 h, then partitioned between EtOAc and water. The organic layers were dried over sodium sulfate and concentrated in vacuo. The residue was purified by column chromatography on silica gel, with a gradient of 1% increasing to 20% MeOH in EtOAc, to give the title compound (0.017 g, 2%) as a white powder. $\delta_H$ (DMSO-$d_6$) 8.68 (s, 1H), 8.53 (s, 1H), 7.38 (d, J=9.1 Hz, 2H), 6.83 (d, J=9.1 Hz, 2H), 6.37 (s, 2H), 5.15 (br s, 2H), 4.50 (br s, 2H), 3.70 (s, 3H), 3.34-3.15 (m, 2H), 1.88-1.79 (m, 2H), 1.69-1.59 (m, 2H). LCMS (ES+) 412.8 (M+H)+, RT 1.676 minutes (method 2).

Example 244

(3S)-4-(5-Aminothiazolo[5,4-d]pyrimidin-7-yl)-3-(hydroxymethyl)-N-(4-methoxy-phenyl)piperazine-1-carboxamide Prepared from Intermediate 79 using Procedure 2. $\delta_H$ (DMSO-$d_6$) 8.70 (s, 1H), 8.36 (s, 1H), 7.37-7.33 (m, 2H), 6.86-6.82 (m, 2H), 6.34 (s, 2H), 5.51 (br m, 2H), 4.87 (t, J=5.1 Hz, 1H), 4.16 (d, J=13.1 Hz, 1H), 4.06 (d, J=12.2 Hz, 1H), 3.72 (s, 3H), 3.69-3.54 (m, 2H), 3.36 (br m, 1H), 3.23 (dd, J 13.6, 4.0 Hz, 1H), 3.12-3.05 (m, 1H). LCMS (ES+) 416.6 (M+H)+, RT 1.19 minutes (method 2).

Example 245

(3S)-4-(5-Aminothiazolo[5,4-d]pyrimidin-7-yl)-3-(hydroxymethyl)-N-(4-methoxy-2-methylphenyl)piperazine-1-carboxamide Prepared from Intermediate 79 using Procedure 6. $\delta_H$ (DMSO-d$_6$) 8.69 (s, 1H), 7.94 (s, 1H), 7.05 (d, J=8.6 Hz, 2H), 6.78-6.66 (m, 1H), 6.35 (s, 2H), 5.45 (br s, 1H), 4.85 (t, J=5.1 Hz, 1H), 4.12-4.01 (m, 3H), 3.71 (s, 3H), 3.69-3.52 (m, 2H), 3.31-2.92 (m, 3H), 2.11 (s, 3H). LCMS (ES+) 430.8 (M+H)$^+$, RT 1.424 minutes (method 2).

Example 246

(3R)-4-(5-Aminothiazolo[5,4-d]pyrimidin-7-yl)-3-(hydroxymethyl)-N-(4-methoxy-phenyl)piperazine-1-carboxamide Prepared from Intermediate 80 using Procedure 7. $\delta_H$ (DMSO-d$_6$) 8.69 (s, 1H), 8.35 (s, 1H), 7.34 (d, J=9.1 Hz, 2H), 6.82 (d, J=9.1 Hz, 2H), 6.34 (s, 2H), 5.51 (br m, 2H), 4.87 (br s, 1H), 4.16 (d, J=13.1 Hz, 1H), 4.06 (d, J=12.2 Hz, 1H), 3.72 (s, 3H), 3.69-3.54 (m, 2H), 3.32-2.99 (m, 3H). LCMS (ES+) 416.6 (M+H)$^+$, RT 1.86 minutes (method 2).

Example 247

8-(5-Aminothiazolo[5,4-d]pyrimidin-7-yl)-N-(4-methoxyphenyl)-3,8-diazabicyclo[3.2.1]-octane-3-carboxamide A mixture of Intermediate 82 (0.61 g, 2.04 mmol) and Intermediate 4 (0.39 g, 2.10 mmol) was suspended in 1,4-dioxane (20 mL) and treated with DIPEA (0.9 mL, 5 mmol). The reaction mixture was heated at 100° C. and stirred for 4 days, then cooled to room temperature and concentrated in vacuo. The reaction mixture was diluted with DCM (20 mL) and water (20 mL) and filtered to remove some brown insoluble material. The layers were separated and the organic layer was washed with brine (2×20 mL), then passed through a phase separator cartridge and evaporated. The resulting crude material was purified by flash chromatography on silica, with a gradient of 1% increasing to 5% MeOH in DCM over 20 column volumes, and then further purified by preparative HPLC. The title compound (0.054 g, 6%) was obtained as a white powder after freeze-drying from acetonitrile/water. $\delta_H$ (DMSO-d$_6$) 8.71 (s, 1H), 8.23 (s, 1H), 7.35-7.30 (m, 2H), 6.84-6.79 (m, 2H), 6.40 (s, 2H), 5.80 (br s, 1H), 5.06 (br s, 1H), 3.93-3.89 (m, 2H), 3.69 (s, 3H), 3.11-3.07 (m, 2H), 1.95 (m, 2H), 1.83 (m, 2H). LCMS (ES+) 413.7 (M+H)$^+$, RT 1.63 minutes (method 2).

Example 248

(3R)-4-(5-Aminothiazolo[5,4-d]pyrimidin-7-yl)-3-cyano-N-[4-(difluoromethoxy)phenyl]-piperazine-1-carboxamide Intermediate 94 (0.052 g, 0.175 mmol) was taken up in DMF (1 mL). DIPEA (0.025 g, 0.192 mmol) and 4-(difluoromethoxy)phenyl isocyanate (0.036 g, 0.192 mmol) were added. The mixture was stirred at room temperature overnight. The reaction mixture was filtered, then purified directly by reverse-phase preparative HPLC, to give the title compound (0.006 g, 8%) as an off-white solid. LCMS (ES+) 447.6 (M+H)$^+$, RT 1.84 minutes (method 2).

The invention claimed is:

1. A compound of formula (IA) or an N-oxide thereof, or a pharmaceutically acceptable salt or solvate thereof:

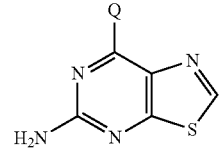

(IA)

wherein
Q represents a group of formula (Qa), (Qb), (Qc), (Qd) or (Qe):

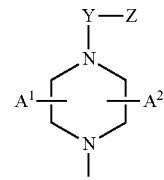

(Qa)

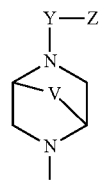

(Qb)

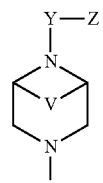

(Qc)

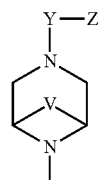

(Qd)

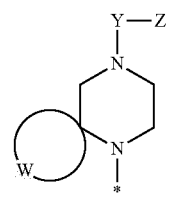

(Qe)

in which the asterisk (*) represents the point of attachment to the remainder of the molecule;
V represents —CH$_2$—, —C(CH$_3$)$_2$—, —CH$_2$CH$_2$— or —CH$_2$CH$_2$CH$_2$—;
W represents the residue of a C$_{3-7}$ cycloalkyl group;
Y represents a covalent bond, or a linker group selected from —C(O)—, —S(O)—, —S(O)$_2$—, —C(O)O—, —C(O)N(R$^2$)— and —S(O)$_2$N(R$^2$)—, or a linker group of formula (Ya):

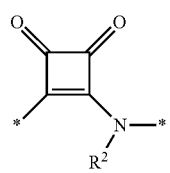
(Ya)

in which the asterisk (*) represents the point of attachment to the remainder of the molecule;

Z represents hydrogen; or $C_{1-6}$ alkyl, $C_{2-6}$ alkenyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents;

$A^1$ represents hydrogen, cyano or trifluoromethyl; or $A^1$ represents $C_{1-6}$ alkyl, optionally substituted by one or more substituents independently selected from —$OR^a$, —$NR^bR^c$, —$CO_2R^d$ and —$CONR^bR^c$; or $A^1$ represents $C_{3-7}$ cycloalkyl;

$A^2$ represents hydrogen or $C_{1-6}$ alkyl;

$R^2$ represents hydrogen; or $C_{1-6}$ alkyl, optionally substituted by one or more substituents independently selected from —$OR^a$ and —$NR^bR^c$;

$R^a$ represents hydrogen; or $R^a$ represents $C_{1-6}$ alkyl, aryl, aryl($C_{1-6}$)alkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents; and $R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents.

2. A compound as claimed in claim 1 wherein Q represents a group of formula (Qa-1), (Qa-2) or (Qa-3):

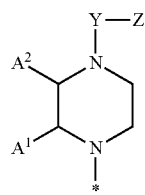
(Qa-1)

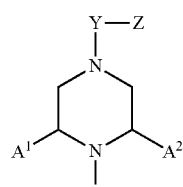
(Qa-2)

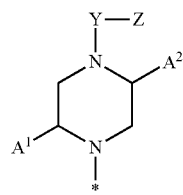
(Qa-3)

in which the asterisk (*) represents the point of attachment to the remainder of the molecule.

3. A compound as claimed in claim 1 represented by formula (IIA), or a pharmaceutically acceptable salt or solvate thereof:

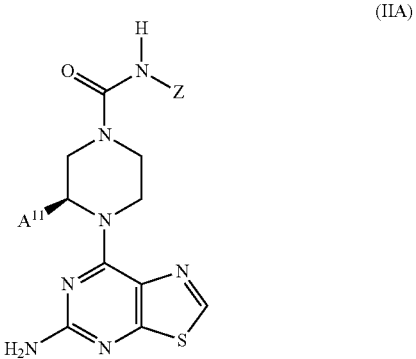
(IIA)

wherein
$A^{11}$ represents hydrogen, cyano, $C_{1-6}$ alkyl, —$CH_2OR^a$, —$CH_2CH_2OR^a$, —$CH_2CO_2R^d$, —$CH_2CONR^bR^c$ or $C_{3-7}$ cycloalkyl.

4. A compound as claimed in claim 1 represented by formula (IIB), or a pharmaceutically acceptable salt or solvate thereof:

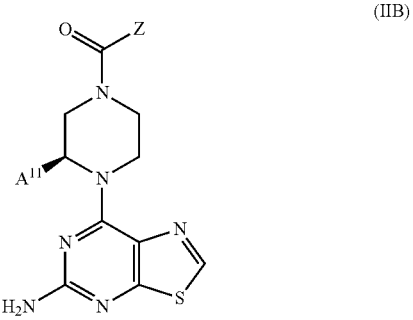
(IIB)

wherein Z is as defined in claim 1; and
$A^{11}$ is hydrogen, cyano, $C_{1-6}$ alkyl, —$CH_2OR^a$, —$CH_2CH_2OR^a$, —$CH_2CO_2R^d$, —$CH_2CONR^bR^c$ or $C_{3-7}$ cycloalkyl.

5. A compound as claimed in claim 1 represented by formula (IIC), or a pharmaceutically acceptable salt or solvate thereof:

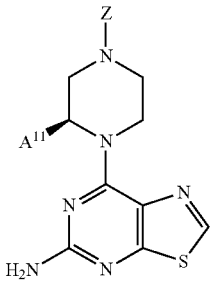

(IIC)

wherein $A^{11}$ is hydrogen, cyano, $C_{1-6}$ alkyl, —$CH_2OR^a$, —$CH_2CH_2OR^a$, —$CH_2CO_2R^d$, —$CH_2CONR^bR^c$ or $C_{3-7}$ cycloalkyl.

6. A compound as claimed in claim 3 wherein $A^{11}$ represents hydrogen, methyl or hydroxymethyl.

7. A compound as claimed in claim 1 wherein Z represents $C_{1-6}$ alkyl, $C_{2-6}$ alkenyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or two substituents independently selected from halogen, cyano, nitro, $C_{1-6}$ alkyl, trifluoro-methyl, cyano($C_{1-6}$)alkyl, ($C_{3-7}$)heterocycloalkyl, halo($C_{3-7}$)heterocycloalkyl, ($C_{1-6}$)alkyl-($C_{3-7}$)heterocycloalkyl, ($C_{2-6}$)alkoxycarbonyl($C_{3-7}$)heterocycloalkyl, dihalo($C_{3-7}$)-heterocycloalkyl, ($C_{3-7}$)heterocycloalkyl($C_{1-6}$)alkyl, ($C_{1-6}$)alkyl($C_{3-7}$)heterocycloalkyl-($C_{1-6}$)alkyl, heteroaryl, hydroxy, oxo, $C_{1-6}$ alkoxy, difluoromethoxy, trifluoromethoxy, ($C_{3-7}$)heterocycloalkoxy, ($C_{2-6}$)alkoxycarbonyl($C_{3-7}$)heterocycloalkoxy, ($C_{3-7}$)-heterocycloalkyl($C_{1-6}$)alkoxy, aryloxy, haloaryloxy, ($C_{1-6}$)alkoxyaryloxy, $C_{1-3}$ alkylenedioxy, dihalo($C_{1-3}$)alkylenedioxy, arylcarbonyloxy, di($C_{1-6}$)alkylamino, di($C_{1-6}$)-alkylamino($C_{1-6}$)alkyl, $C_{2-6}$ alkylcarbonylamino, $C_{2-6}$ alkoxycarbonyl, aryloxycarbonyl and aminocarbonyl.

8. A compound as claimed in claim 7 wherein Z represents methoxyphenyl, (methoxy)(methyl)phenyl or (difluoroazetidinyl)(methyl)pyridinyl.

9. A pharmaceutical composition comprising a compound of formula (IA) as defined in claim 1 or an N-oxide thereof, or a pharmaceutically acceptable salt or solvate thereof, in association with a pharmaceutically acceptable carrier.

10. A method for the treatment and/or prevention of organ or cell transplant rejection, which comprises administering to a patient in need of such treatment an effective amount of a compound of formula (IA) as defined in claim 1 or an N-oxide thereof, or a pharmaceutically acceptable salt or solvate thereof.

* * * * *